US012678288B2

(12) United States Patent
Lee et al.

(10) Patent No.: US 12,678,288 B2
(45) **Date of Patent: *Jul. 14, 2026**

(54) SYSTEM AND METHOD FOR JOINING BONEY STRUCTURES

(71) Applicant: Randall F. Lee, Southlake, TX (US)

(72) Inventors: Randall F. Lee, Southlake, TX (US);
Daniel S. Savage, Brecksville, OH
(US); Alan W. Rorke, Bristol (GB)

(73) Assignee: Randall F. Lee, Southlake, TX (US)

( * ) Notice: Subject to any disclaimer, the term of this
patent is extended or adjusted under 35
U.S.C. 154(b) by 456 days.

This patent is subject to a terminal dis-
claimer.

(21) Appl. No.: 18/123,739

(22) Filed: Mar. 20, 2023

(65) Prior Publication Data

US 2023/0225869 A1      Jul. 20, 2023

Related U.S. Application Data

(63) Continuation      of      application      No.
PCT/US2021/051250, filed on Sep. 21, 2021, and a
(Continued)

(51) Int. Cl.
*A61F 2/30*          (2006.01)
*A61B 17/80*          (2006.01)
(Continued)

(52) U.S. Cl.
CPC ...... *A61F 2/30749* (2013.01); *A61B 17/8004*
(2013.01); *A61B 17/844* (2013.01); *A61F*
*2/4603* (2013.01); *A61B 2017/564* (2013.01);
*A61B 2017/681* (2013.01); *A61B 17/846*
(2013.01); *A61F 2002/30622* (2013.01); *A61F*
*2/4202* (2013.01); *A61F 2/4455* (2013.01)

(58) Field of Classification Search
CPC .............. A61B 17/8004; A61B 17/844; A61F
2/30749; A61F 2/4603
See application file for complete search history.

(56) References Cited

U.S. PATENT DOCUMENTS 3,506,982 A      4/1970  Steffee
3,552,389 A      1/1971  Martin et al.
(Continued)

FOREIGN PATENT DOCUMENTS

AU          2013224006 B          2/2017
CA              2635537 C          5/2014
(Continued)

OTHER PUBLICATIONS

Final Office Action, mailed Aug. 5, 2025, by the USTPO, re U.S.
Appl. No. 18/485,363.
(Continued)

*Primary Examiner* — Sameh R Boles
(74) *Attorney, Agent, or Firm* — Law Office of Bill
Naifeh

(57)          ABSTRACT

Disclosed are system and methods that use at least one
non-threaded anchor and an implant with at least one
aperture to join boney structures, where the interaction of the
head of the anchor with the implant aperture causes the
anchor to move transversely with respect to an initial
trajectory. This movement causes compression or distraction
of the boney structures which are coupled to the anchors.

8 Claims, 43 Drawing Sheets

Related U.S. Application Data continuation of application No. 17/372,327, filed on Jul. 9, 2021, now Pat. No. 11,839,547, and a continuation of application No. 17/248,943, filed on Feb. 13, 2021, now Pat. No. 11,058,542, and a continuation of application No. 17/175,649, filed on Feb. 13, 2021, now Pat. No. 11,160,589.

(60) Provisional application No. 63/130,323, filed on Dec. 23, 2020, provisional application No. 63/113,886, filed on Nov. 15, 2020, provisional application No. 63/081,187, filed on Sep. 21, 2020.

(51) Int. Cl.

| | |
|---|---|
| *A61B 17/84* | (2006.01) |
| *A61F 2/46* | (2006.01) |
| *A61B 17/56* | (2006.01) |
| *A61B 17/68* | (2006.01) |
| *A61F 2/42* | (2006.01) |
| *A61F 2/44* | (2006.01) |

(56) References Cited

U.S. PATENT DOCUMENTS

| | | |
|---|---|---|
| 4,484,570 A | 11/1984 | Sutter et al. |
| 4,790,303 A | 12/1988 | Steffee |
| 6,984,234 B2 | 1/2006 | Bray |
| 7,488,320 B2 | 2/2009 | Middleton |
| 7,572,280 B2 | 8/2009 | Dickinson et al. |
| 8,267,997 B2 | 9/2012 | Colleran |
| 8,268,000 B2 | 9/2012 | Waugh et al. |
| 8,328,872 B2 | 12/2012 | Duffield et al. |
| 8,361,155 B2 | 1/2013 | Lambrecht et al. |
| 8,540,769 B2 | 9/2013 | Janowski et al. |
| 8,641,766 B2 | 2/2014 | Donner et al. |
| 8,764,831 B2 | 7/2014 | Lechmann et al. |
| 8,882,775 B2 | 11/2014 | Laposta et al. |
| 8,968,405 B2 | 3/2015 | Kirwan et al. |
| 8,979,930 B2 | 3/2015 | Glazer |
| 9,351,847 B2 | 5/2016 | Reed et al. |
| 9,408,715 B2 | 8/2016 | Donner et al. |
| 9,526,620 B2 | 12/2016 | Slivka et al. |
| 9,566,165 B2 | 2/2017 | Lee et al. |
| 9,937,055 B1 | 4/2018 | Bernhardt et al. |
| 10,022,161 B2 | 7/2018 | Blain et al. |
| 10,098,755 B2 | 10/2018 | Kaufmann et al. |
| 10,195,051 B2 | 2/2019 | Bergey et al. |
| 10,245,156 B2 | 4/2019 | Chataigner et al. |
| 10,258,479 B2 | 4/2019 | Stewart et al. |
| 10,376,377 B2 | 8/2019 | Seifert et al. |
| 10,433,975 B2 | 10/2019 | Ashleigh et al. |
| 10,478,310 B2 | 11/2019 | Ameil et al. |
| 10,485,591 B2 | 11/2019 | Lequette et al. |
| 10,631,999 B2 | 4/2020 | Gilbride et al. |
| 10,758,370 B2 | 9/2020 | Gilbride et al. |
| 11,058,542 B1 | 7/2021 | Lee et al. |
| 11,160,589 B1 | 11/2021 | Lee et al. |
| 11,839,547 B2 | 12/2023 | Lee et al. |
| 11,872,141 B2 | 1/2024 | Lee et al. |
| 2005/0182408 A1 | 8/2005 | Pfefferle et al. |
| 2006/0195094 A1 | 8/2006 | McGraw et al. |
| 2009/0210062 A1 | 8/2009 | Thalgott et al. |
| 2009/0254126 A1 | 10/2009 | Orbay et al. |
| 2011/0098747 A1 | 4/2011 | Donner et al. |
| 2012/0078371 A1 | 3/2012 | Gamache et al. |
| 2012/0078373 A1 | 3/2012 | Gamache et al. |
| 2013/0079879 A1 | 3/2013 | Suh |
| 2013/0150968 A1 | 6/2013 | Dinville et al. |
| 2013/0166029 A1 | 6/2013 | Dinville et al. |
| 2013/0245767 A1 | 9/2013 | Lee et al. |
| 2014/0180417 A1 | 6/2014 | Bergey |
| 2015/0127109 A1 | 5/2015 | Brett et al. |
| 2016/0074172 A1 | 3/2016 | Lee et al. |
| 2016/0106550 A1 | 4/2016 | Slivka et al. |
| 2016/0151171 A1 | 6/2016 | Mozeleski et al. |
| 2016/0338853 A1 | 11/2016 | Donner et al. |
| 2017/0007305 A1 | 1/2017 | Hollis et al. |
| 2017/0071750 A1 | 3/2017 | Urban et al. |
| 2017/0246007 A1 | 8/2017 | Chataigner et al. |
| 2018/0177606 A1 | 6/2018 | Reed et al. |
| 2018/0214280 A1 | 8/2018 | Seifert et al. |
| 2018/0325694 A1 | 11/2018 | Petersheim et al. |
| 2019/0000637 A1 | 1/2019 | Gilbride et al. |
| 2019/0000638 A1 | 1/2019 | Gilbride et al. |
| 2019/0105174 A1* | 4/2019 | Kaufmann .............. A61F 2/447 |
| 2019/0183658 A1 | 6/2019 | Lambrecht et al. |
| 2019/0328540 A1 | 10/2019 | Seifert et al. |
| 2022/0087820 A1 | 3/2022 | Lee et al. |
| 2022/0087821 A1 | 3/2022 | Lee et al. |
| 2023/0225775 A1 | 7/2023 | Lee et al. |

FOREIGN PATENT DOCUMENTS

| | | |
|---|---|---|
| CN | 108969163 A | 12/2018 |
| EP | 1968464 B1 | 2/2012 |
| EP | 2419030 B1 | 1/2017 |
| EP | 2701638 B1 | 5/2017 |
| EP | 3207900 B1 | 7/2018 |
| EP | 3470022 A1 | 4/2019 |
| FR | 2954692 A1 | 7/2011 |
| FR | 3005569 A1 | 11/2014 |
| FR | 3016793 A1 | 7/2015 |
| JP | 2017507000 A | 3/2017 |
| JP | 2018187417 A | 11/2018 |
| KR | 101555317 B | 10/2015 |
| KR | 101636010 B | 7/2016 |
| KR | 20160145538 A | 12/2016 |
| NO | 2011129973 A1 | 10/2011 |
| RU | 2631208 C2 | 9/2017 |
| WO | 2010121028 A2 | 10/2010 |
| WO | 2013062716 A1 | 5/2013 |
| WO | 2016100158 A1 | 6/2016 |
| WO | 2017029301 A1 | 2/2017 |
| WO | 2017087020 A1 | 5/2017 |
| WO | 2017186966 A1 | 11/2017 |
| WO | 2018140352 A1 | 8/2018 |
| WO | 2022061278 A1 | 3/2022 |
| WO | 2022061302 A1 | 3/2022 |

OTHER PUBLICATIONS

Final Office Action, mailed Jun. 25, 2025, by the USPTO, in U.S. Appl. No. 17/513,993.
Office Action, mailed Jun. 2, 2023, by the USPTO, re U.S. Appl. No. 17/372,327.
Office Action, dated Mar. 5, 2025, by the USPTO, re U.S. Appl. No. 17/513,993.
International Search Report, by the ISA/US, mailed Jan. 25, 2022, regarding PCT/US2021/051250.
International Search Report, by the ISA/US, mailed Jan. 24, 2022, regarding PCT/US2021/051348.
Office Action, mailed Apr. 19, 2021, by the USPTO, regarding U.S. Appl. No. 17/175,649.
Written Opinion, by the ISA/US, mailed Jan. 25, 2022, regarding PCT/US2021/051250.
Written Opinion, by the ISA/US, mailed Jan. 24, 2022, regarding PCT/US2021/051348.
Notice of Allowance, mailed Sep. 13, 2023, by the USPTO, re U.S. Appl. No. 17/372,327.
Notice of Allowance, mailed Jul. 1, 2021, by the USPTO, re Application No. 17/175,649.
Notice of Allowance, mailed Apr. 28, 2021, by the USPTO, re U.S. Appl. No. 17/248,943
Office Action-Restriction Requirement, mailed Apr. 6, 2021, by the USPTO, re U.S. Appl. No. 17/248,943.
Office Action-Restriction Requirement, mailed Mar. 30, 2021, by the USPTO, re U.S. Appl. No. 17/175,649.
Office Action, dated Oct. 20, 2025, by the USPTO, re U.S. Appl. No. 17/513,993.

(56) References Cited

OTHER PUBLICATIONS

Office Action-Restriction, dated Sep. 8, 2025, by the USPTO, in U.S. Appl. No. 18/123,765.

Notice of Allowance, dated Dec. 16, 2025, by the USPTO, in U.S. Appl. No. 18/485,363.

Notice of Allowance, mailed Feb. 2, 2026, by the USPTO, in U.S. Appl. No. 18/123,765.

Office Action, dated Jun. 1, 2026, by the USPTO, in U.S. Appl. No. 17/513,993.

* cited by examiner

444a

442

402

444a

442

444b

402

1200

1210

1216a

1204

800

200a

1200

1210

1216a

1204

800

200a

SYSTEM AND METHOD FOR JOINING BONEY STRUCTURES

CROSS REFERENCE TO RELATED APPLICATIONS

This application is a continuation of PCT International Application No. PCT/US2021/051250, filed Sep. 21, 2021, entitled SYSTEM AND METHOD FOR JOINING BONEY STRUCTURES, which claims priority to U.S. patent application Ser. No. 17/372,327, filed on Jul. 9, 2021, entitled SYSTEM AND METHOD FOR JOINING BONEY STRUCTURES, U.S. patent application Ser. No. 17/248, 943, filed on Feb. 13, 2021, now U.S. Pat. No. 11,058,542, entitled SYSTEM AND METHOD FOR JOINING BONEY STRUCTURES, and U.S. patent application Ser. No. 17/175,649, filed on Feb. 13, 2021, now U.S. Pat. No. 11,160,589, entitled SYSTEM AND METHOD FOR JOIN-ING BONEY STRUCTURES; and claims the benefit of the filing dates of the following U.S. provisional patent appli-cations: U.S. Provisional Application No. 63/130,323, filed on Dec. 23, 2020, entitled SYSTEM AND METHOD FOR JOINING BONEY STRUCTURES, U.S. Provisional Appli-cation No. 63/113,886, filed on Nov. 15, 2020, entitled SYSTEM AND METHOD FOR JOINING BONEY STRUCTURES, and U.S. Provisional Application No. 63/081,187, filed on Sep. 21, 2020, entitled SYSTEM AND METHOD FOR JOINING BONEY STRUCTURES. The disclosures of all of the above patent applications are hereby incorporated by reference for all purposes. This application also incorporates by reference for all purposes a commonly owned patent application entitled SYSTEM AND METHOD FOR JOINING BONEY STRUCTURES, PCT International Application No. PCT/US2021/051348, filed Sep. 21, 2021, entitled SYSTEM AND METHOD FOR JOINING BONEY STRUCTURES.

TECHNICAL FIELD

The disclosed invention relates in general to orthopedic and dental surgically implanted devices, and in particular to implantable devices which use a plurality of non-threaded anchors with an implant or plate to compress and join boney structures.

BACKGROUND INFORMATION

Over a hundred years ago surgeons determined that a combination of screws and plates worked as a method of internal fixation of two or more bone structures. In time surgeons empirically learned that placing two or more bones in mechanical compression greatly improved the speed and quality of bone healing. Mechanical compression was then rendered through external devices and internally fixated with the screw plate device.

Many believe that localized bone compression is the orthopaedic standard for bone healing. Current art uses plates with dedicated screw channels or directive apertures that determine the range of screw angulation and the resul-tant course of the screw's trajectory.

In many orthopedic related procedures, however, such as spinal, sternal chest closure, dental, and numerous orthope-dic reconstructions, plates and screws have not been found to follow compressive bone healing principals. Instead, the screw plate configurations stabilize the boney structures, but do not typically compress the bone structures together.

Furthermore, threaded anchors such as screws have many disadvantages, including the tendency to back out of a boney structure over time.

Therefore, what is needed is a novel plate anchor system that consistently achieves bone compression or distraction of two boney structures together.

SUMMARY

In response to these and other problems, in one embodi-ment, there is a system that includes non-threaded anchors that follow a trajectory into a boney structure and then a non-threaded head of the anchor interacts with the aperture features in an interbody implant to cause the anchor to move transversely within the aperture which can cause compres-sion or distraction of boney structures coupled to the anchors.

These and other features, and advantages, will be more clearly understood from the following detailed description taken in conjunction with the accompanying drawings. It is important to note the drawings are not intended to represent the only aspect of the invention.

DETAILED DESCRIPTION

Figures 1A, 1B:
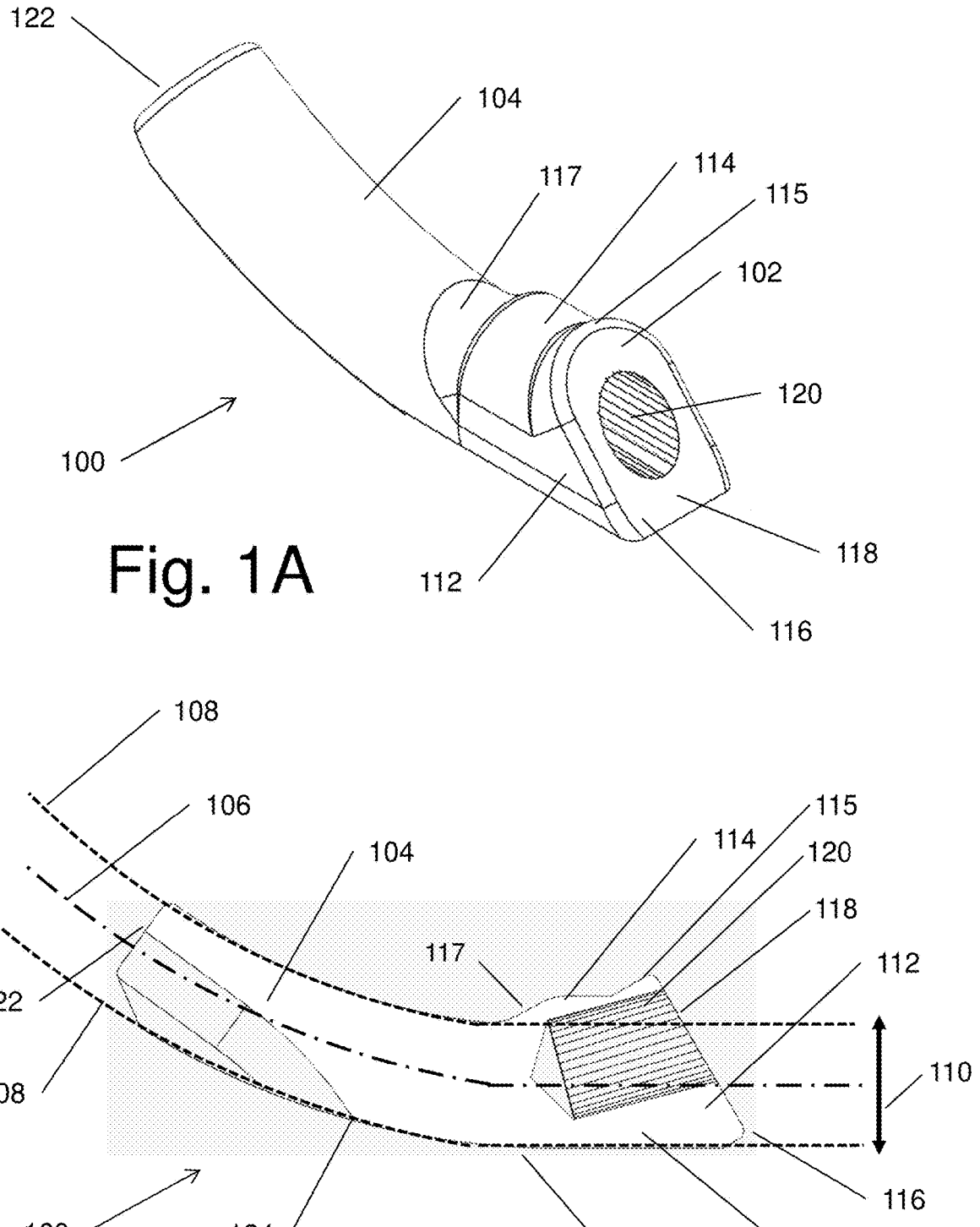
FIG. 1A is a perspective view of one aspect of a non-threaded anchor which can be used in one or more aspects of the present invention.
FIG. 1B is a longitudinal section view of the non-threaded anchor of FIG. 1A.

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientation of components in respect to each other or to illustrate the figures. The directions should not be read to imply actual directions used in any resulting invention or actual use. Under no circumstances, should such directions be read to limit or impart any meaning into the claims.

Anchor Embodiments

Offset Head Embodiments

Figure 10:
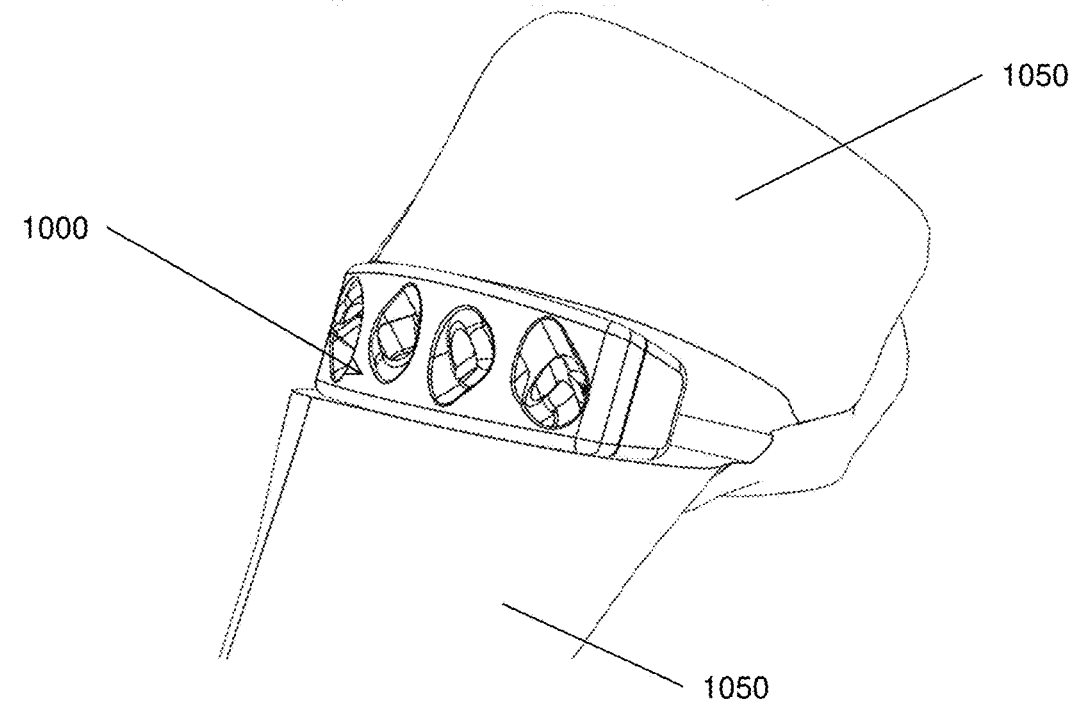
FIG. 10 is a four anchor embodiment used as an osteotomy wedge.

FIG. 1A is a proximal perspective view of one aspect of a non-threaded anchor 100 which can be used with several embodiments of the present invention. FIG. 1B is a longitudinal section view of the non-threaded anchor 100. FIG. 10 is a top perspective view of the anchor 100 orientated to illustrate a distal end 122. In contrast, FIG. 1D is a bottom perspective view of the anchor 100.

Turning now to FIGS. 1A through 1D, in the illustrative embodiment, the non-threaded anchor 100 includes a non-threaded proximal end or head portion 102 which is coupled to a non-threaded longitudinal body portion 104. The non-threaded elongated body 104 has a longitudinal or center axis 106, which in this embodiment, partially defines an initial trajectory into a boney structure as will further be discussed below. In the illustrated embodiment, the head portion 102 and the elongated body portion 104 share central axis 106 and the central axis 106 is curved within the elongated body portion 104 and straight within the head portion 102. In other embodiments, the elongated body portion 104 may be straight in which the center axis 106 would also be straight. In yet other embodiments, the head portion 102 may be curved and likewise, the center axis 106 within the head portion may also be curved.

FIG. 1B is a section view of the anchor 100 with the addition of dotted lines 108. For purposes of illustration, the dotted lines 108 are boundary lines that represent the portion of the anchor 100 that is generally equal distance with respect to the center axis 106 in a direction 110 that is generally normal or transverse to the direction of the center axis 106. For purposes of this disclosure, any portion of the head portion 102 that is outside of the dotted lines 108 is defined as "offset" or eccentric to the center axis 106. As can be seen most clearly in FIG. 1B, the non-threaded head portion 102 includes a first or "symmetrical" head portion 112 that is substantially within the boundary lines 108 and a second or "offset" portion 114 of the head portion 102 that is outside of the boundary lines 108 (where symmetrical is relative to the center axis). Looking from the perspective of FIG. 1B, the boundary lines 108 are generally symmetrical or equal distance from the center axis 106 in a direction 110 which is normal to the center axis. Thus, for purposes of this disclosure, the second or offset portion 114 of the head portion 102 that is outside of the boundary lines 108 is defined as an offset portion 114 from the center axis. In other words, an unsymmetrical mass or structure beyond an equal distance line from the center axis is considered to be an "offset" portion of a head for purposes of this disclosure. A transition or blended surface 117 allows for the smooth transition between the surface of the elongated body portion 104 and the offset anchor head portion 114.

In certain embodiments, a proximal end 116 contains an engagement surface 118 that is angled with respect to the normal direction 110 of center axis 106. In certain embodiments, the engagement surface 118 may have engagement features, such as aperture 120 for engaging with various embodiments of insertion instruments as will be explained below. In the illustrative embodiment, the longitudinal axis of the aperture 120 may be angled with respect to the center axis 106.

In the illustrative embodiment, a crest 115 of the offset portion 114 is formed at the distal end of the engagement surface 118 as illustrated in FIG. 1B. The height of the offset portion 114 decreases as one moves along the longitudinal direction from the proximal end 116 towards the distal direction as illustrated in FIG. 1A and FIG. 1B. In certain embodiments, the oversized geometry of the offset portion 114 causes a light press fit between the anchor head portion 114 and the aperture of an implant. Thus, in some embodiments, the offset portion 114 may be an oversized geometric volume which contacts a surface of the aperture. These are cylindrical surfaces which will largely be concentric in the final position, and in the offset portion 114 they may have an incrementally larger radius than the underside of the surface in the aperture resulting in being wedged together in the final position—which assists in preventing the anchor from "backing out" of the respective aperture. In yet other embodiments, other anti-back methods and techniques may also be employed, such as blocker plates, retaining rings, and locking screws.

Figure 1C:
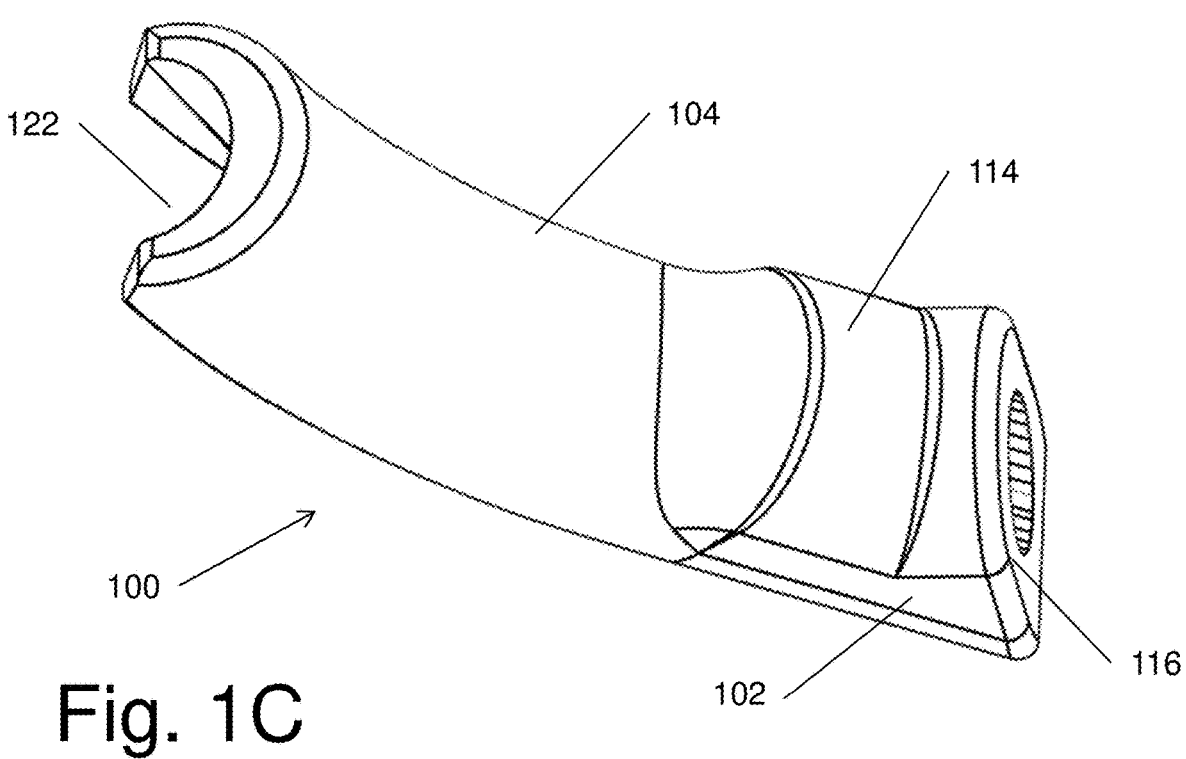
FIG. 1C is a top perspective view of the non-threaded anchor of FIG. 1A orientated so that the distal end is illustrated.
Figure 1D:
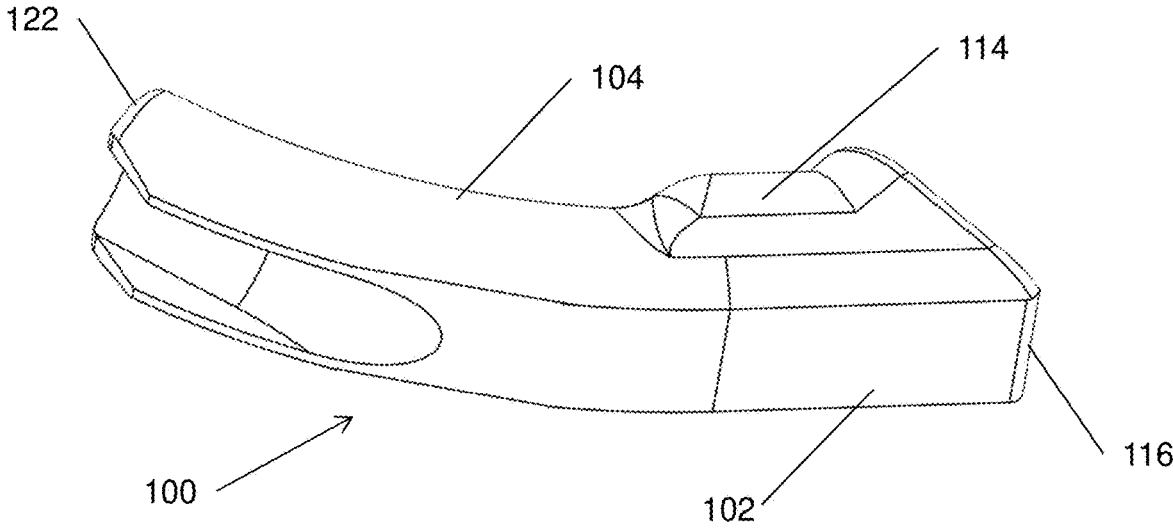
FIG. 1D is a bottom perspective view of the non-threaded anchor of FIG. 1A.
Figure 1E:
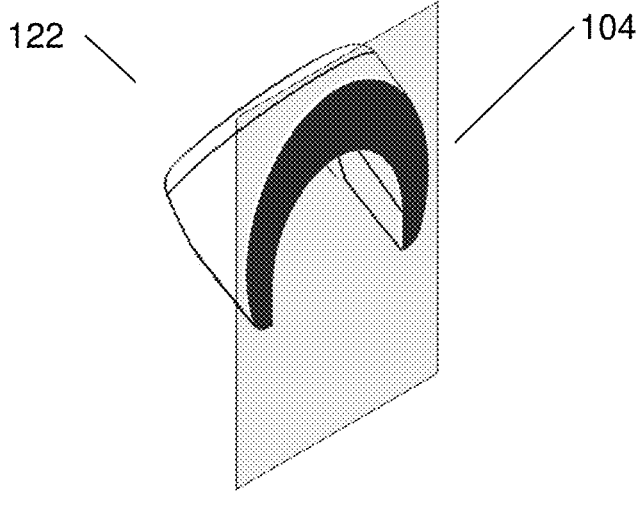
FIGS. 1E through 1H are transverse sectional views of the non-threaded anchor of FIG. 1A.
Figure 1F:
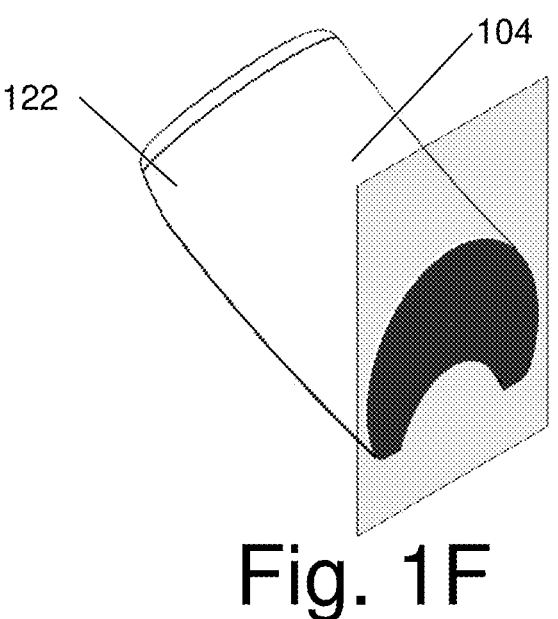

As can be best seen in FIGS. 1C and 1D, a distal end 122 of the anchor 100 is designed to penetrate and be pushed through a boney structure. Consequently, at the distal end 122 the cross-sectional area of the body portion 104 is significantly reduced which also reduces the force necessary to push the distal end 122 through the boney structure (not shown). In the illustrative embodiment as best seen in FIG. 1C, the distal end 122 has a generally semi-circular or horseshoe shaped cross-sectional area. For instance, FIG. 1E is a partial perspective view where the body portion 104 has been cut close to the distal end 122. The cut in FIG. 1E is in a vertical direction and illustrates the horseshoe shape of cross-section of the body portion 104 when the section is cut close to the distal end 122. In contrast, FIG. 1F is a partial perspective view where the body portion 104 has been cut at a point between the distal end 122 and a midsection point 124 (see FIG. 1B). The cut in FIG. 1F is in a vertical direction and illustrates a substantial thickening of the horseshoe shape of cross-section of the body portion 104.

Figure 1G:
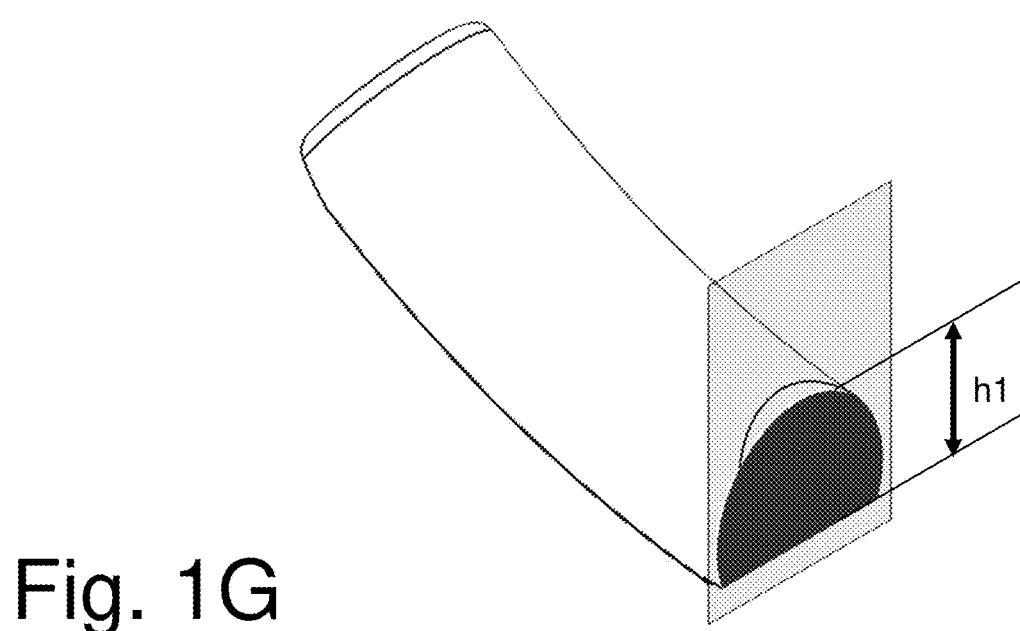
Figure 1H:
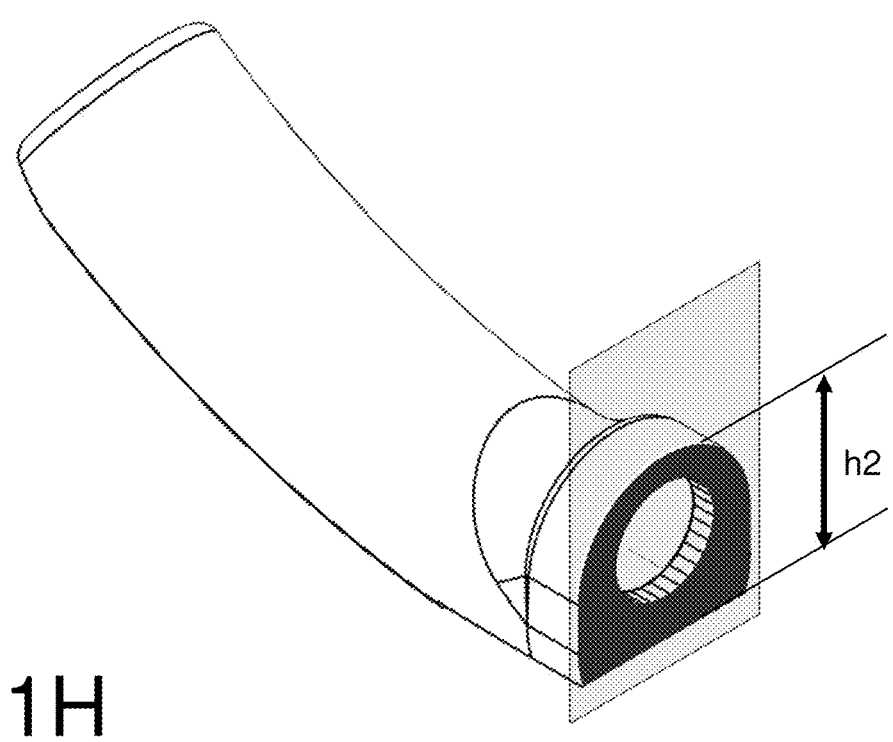

FIG. 1G is a partial perspective view where the body portion 104 has been cut at the midsection point 124 (see FIG. 1B). The cut in FIG. 1G is in a vertical direction and illustrates a cross-sectional shape of a solid elliptical segment. As illustrated, the body portion 104 has a vertical thickness or height of h1 at this cut point. In contrast, FIG. 1H is a partial perspective view where the head portion 102 has been cut around a point 126 (see FIG. 1B). As illustrated, the head portion 102 has a vertical thickness or height of h2 at this cut point. The height of the head portion increases until the crest 115 is reached as explained above. Note the difference in between the height h1 in FIG. 1G and the height h2 in FIG. 1H is created by the offset portion 114 of the head portion 102 as discussed above.

Figure 2A:
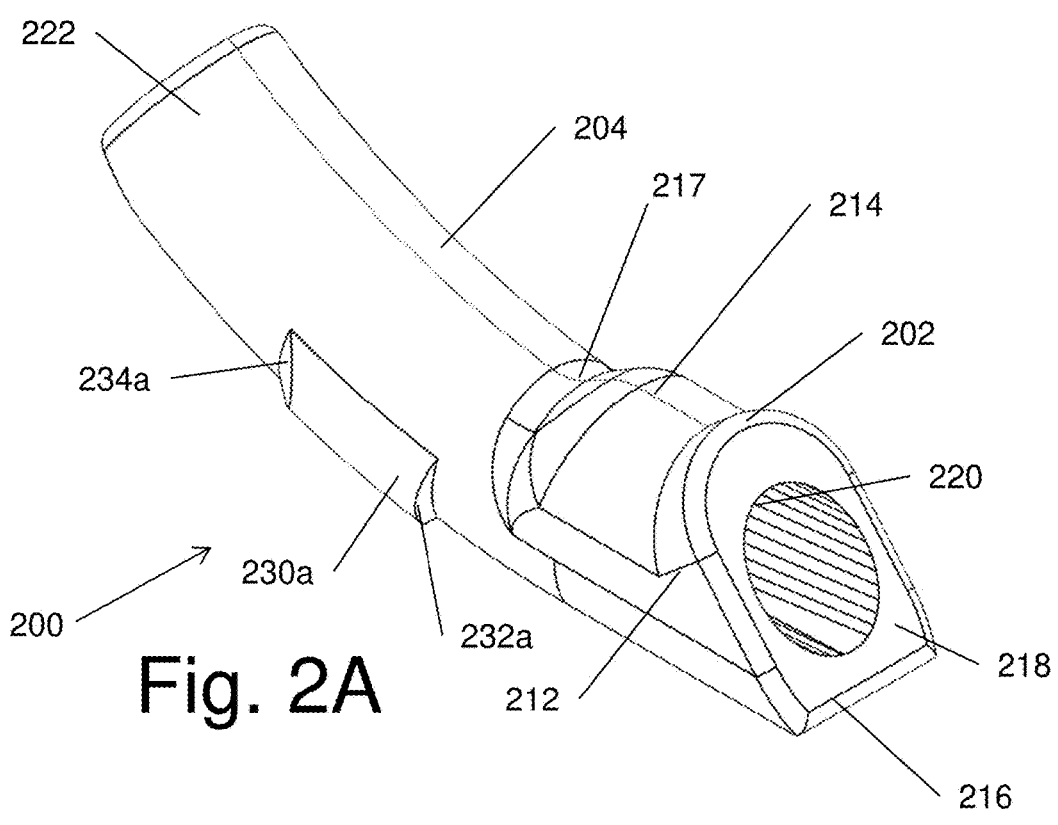
FIG. 2A is a perspective view of an alternative aspect of a non-threaded anchor which can be used in one or more aspects of the present invention.
Figure 2B:
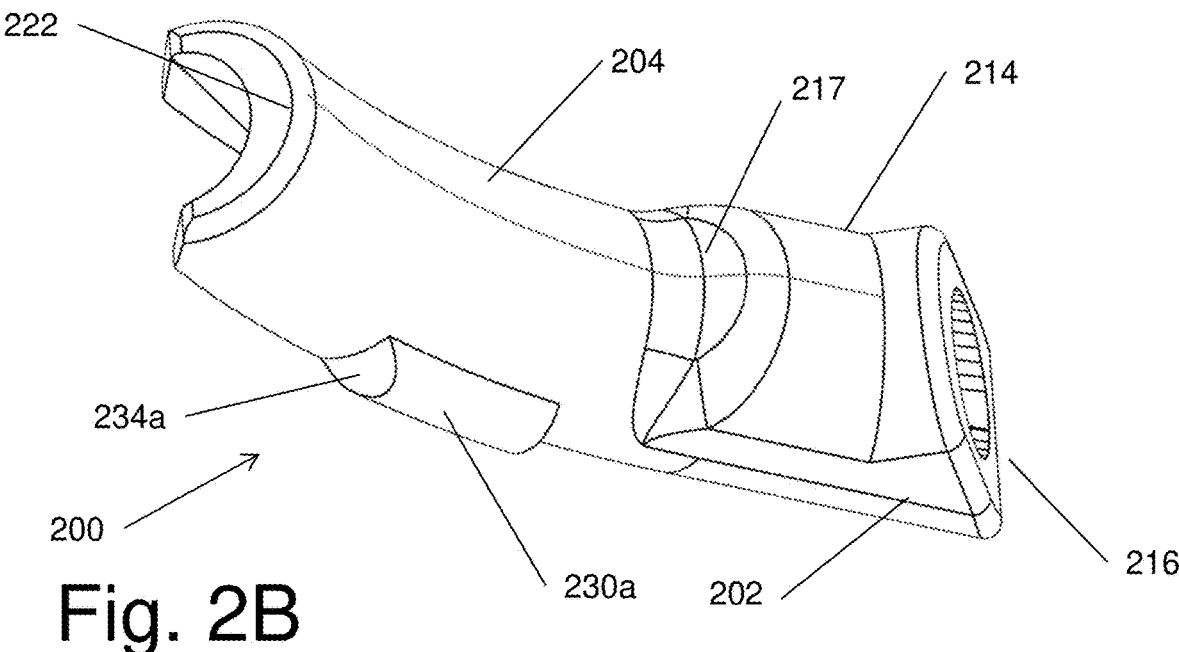
FIG. 2B is a top perspective view of the non-threaded anchor of FIG. 2A orientated so that the distal end is illustrated.

Anchors with Side Rails:

A second embodiment an anchor is illustrated in FIG. 2A which is a perspective view of an alternative anchor 200 and also can be used with several embodiments of the present invention. FIG. 2B is a top perspective view of the anchor 200 orientated to illustrate a distal end 222. In contrast, FIG. 2C is a bottom perspective view of the anchor 200.

For brevity and clarity, some of the description of those parts which are identical or similar to those described in connection with the first embodiment illustrated in FIGS. 1A through 1H will not be repeated here. Reference should be made to the foregoing paragraphs with the following description to arrive at a complete understanding of this second embodiment.

Figure 2C:
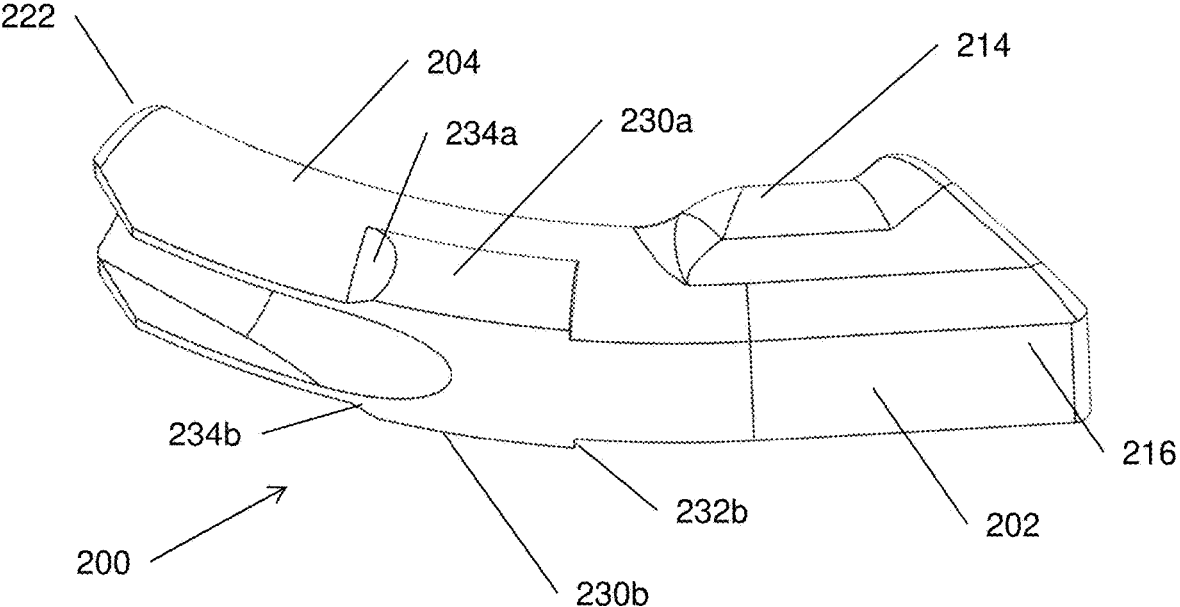
FIG. 2C is a bottom perspective view of the non-threaded anchor of FIG. 2A.

Turning now to FIGS. 2A through 2C, in the illustrative embodiment, the non-threaded anchor 200 includes a non-threaded proximal end or head portion 202 which is coupled to a non-threaded longitudinal body portion 204.

In certain embodiments, the head portion includes a proximal end 216 which includes a tool engagement surface 218 that is angled in a manner similar to the tool engagement surface 118 discussed above. In certain embodiments, the tool engagement surface 218 may have engagement features, such as aperture 220 for engaging with various embodiments of insertion instruments and tools as will be explained below. In the illustrative embodiment, the longitudinal axis of the aperture 220 may be angled with respect to the center axis of the head portion 202 as described above in reference to FIG. 1B.

In certain embodiments, the head portion 202 also includes an offset portion 214 which extends out on one side in a direction normal or transverse to the central axis of the head 202 as explained above in reference to FIG. 1B. A transition or blended surface 217 allows for the smooth transition between the surface of the elongated body portion 204 and the offset anchor head portion 214.

The distal end 222 of the anchor 200 is designed to penetrate and be pushed through a boney structure. Consequently, at the distal end 222 the cross-sectional area of the body portion 204 is significantly reduced which also reduces the force necessary to push the distal end 222 through the boney structure. In the illustrative embodiment the distal end 222 has a generally semi-circular or horseshoe shaped cross-sectional area. However, the cross-sectional shape is exemplary.

The primary difference between the anchor 100 and the anchor 200 is the addition of side rails 230a and 230b extending in a lateral direction or perpendicularly out from the surface on both sides of the body portion 204 (side rail 230b is not shown in FIGS. 2A and 2B). As will be explained below, the side rails 230a and 230b facilitate the centering of the anchor 200 within an aperture of an implant (not shown) when the body portion 204 is pushed through the aperture. In certain embodiments, the side rails 230*a* and 230*b* are curved and have the shape of a circular segment in cross-section as illustrated by a proximal surface 232*a* of the side rail 230*a* in FIG. 2A which extends out from the surface of body portion 204 in a lateral or perpendicular manner. In contrast, the side rails 230*a* and 230*b* also have distal or engaging surface 234*a* (234*b* is not shown) which is angled with respect to the surface of the body portion 204 to reduce the engaging force necessary to penetrate into the boney structure. The engaging surface 234*a* is best illustrated in FIG. 2B.

As will be explained below in greater detail, side rails 230*a* and 230*b* engage correspondingly shaped channels or grooves defined within apertures of an implant to assist in guiding an anchor along a trajectory as the anchor penetrates the boney structure.

Figures 3A, 3B:
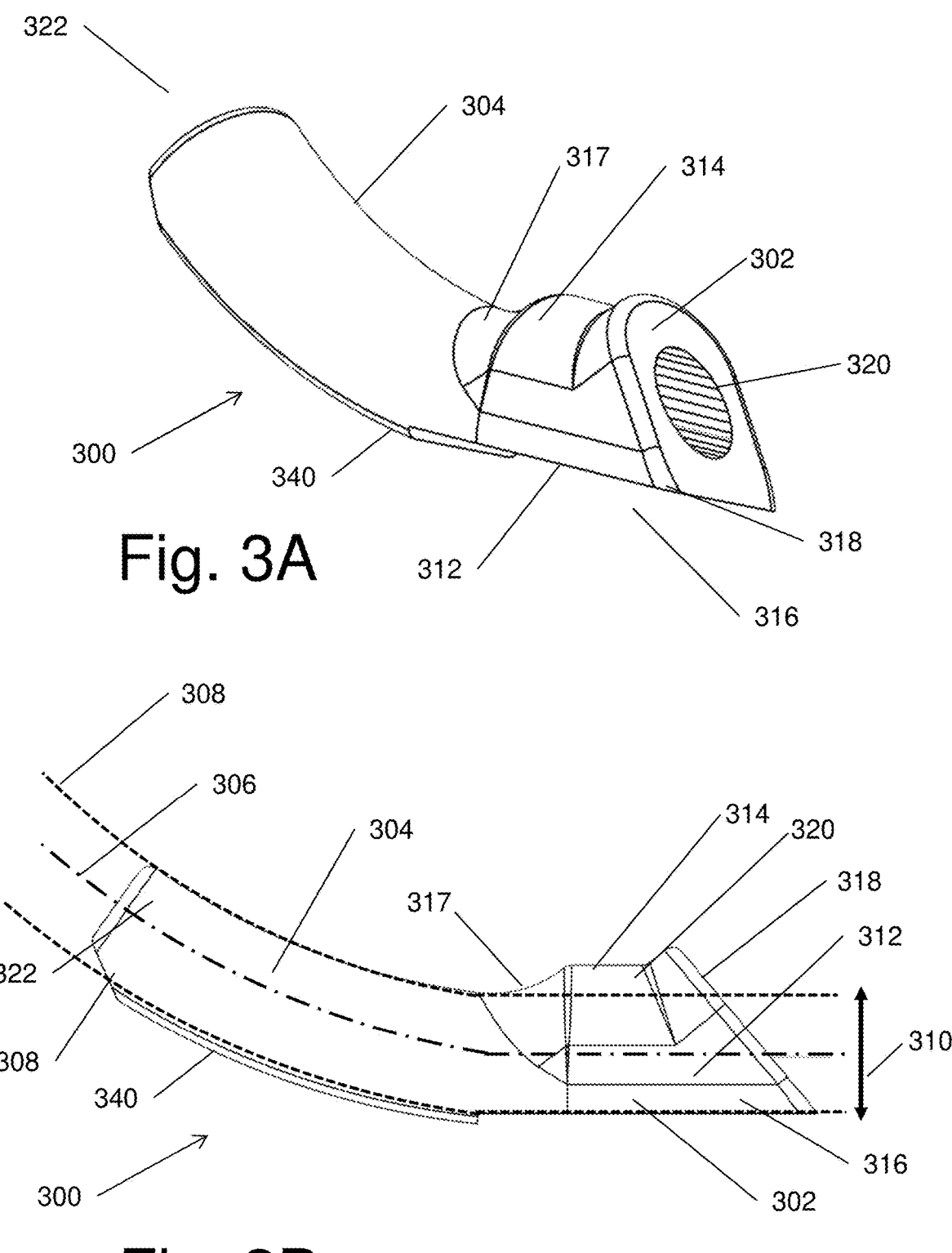
FIG. 3A is a perspective view of one aspect of a non-threaded anchor which can be used in one or more aspects of the present invention.
FIG. 3B is a longitudinal section view of the non-threaded anchor of FIG. 3A.
Figure 3C:
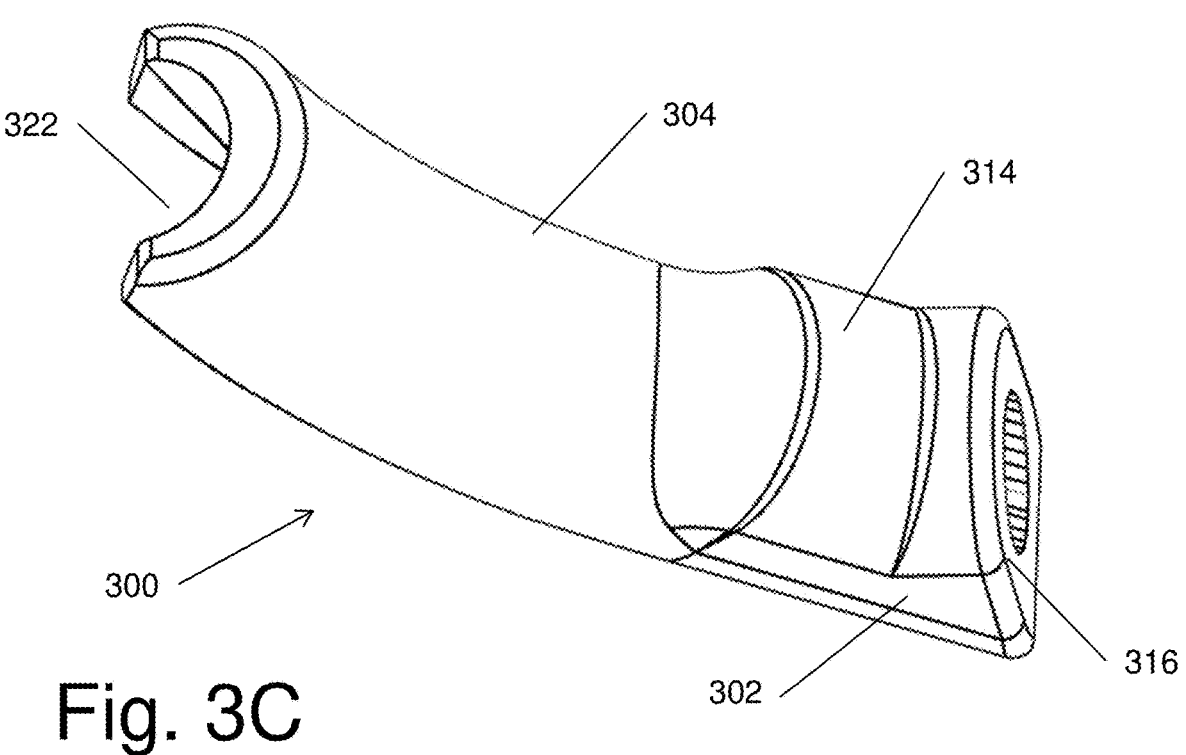
FIG. 3C is a top perspective view of the non-threaded anchor of FIG. 3A orientated so that the distal end is illustrated.
Figure 3D:
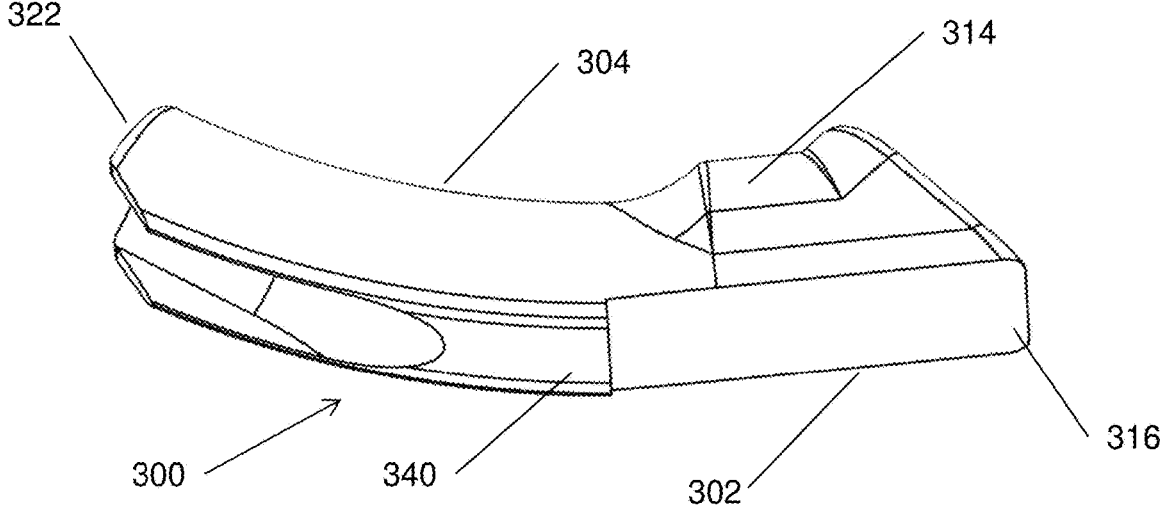
FIG. 3D is a bottom perspective view of the non-threaded anchor of FIG. 3A.

Anchors with a Stepped Surface:

A third embodiment an anchor is illustrated in FIG. 3A which is a side perspective view of an alternative anchor 300 which can be used with several embodiments of the present invention. FIG. 3B is a longitudinal side view of the anchor 300. FIG. 3C is a top perspective view of the anchor 300 orientated to illustrate a distal end 322. In contrast, FIG. 3D is a bottom perspective view of the anchor 300.

For brevity and clarity, some of the description of those parts which are identical or similar to those described in connection with the first two embodiments illustrated in FIGS. 1A through 2C will not be repeated here. Reference should be made to the foregoing paragraphs with the following description to arrive at a complete understanding of this second embodiment.

Turning now to FIGS. 3A through 3D, in the illustrative embodiment, the non-threaded anchor 300 includes a non-threaded proximal end or head portion 302 which is coupled to a non-threaded longitudinal body portion 304. The non-threaded elongated body 304 has a center axis 306, which in this embodiment, partially defines an initial trajectory into a boney structure as will further be discussed below.

FIG. 3B is a longitudinal side view of the anchor 300 illustrating the center axis 306 and with the addition of dotted lines 308. For purposes of illustration, the dotted lines 308 are "boundary" lines that represent the portion of the anchor that is generally equal distance with respect to the center axis 306 in a direction 310 that is generally normal to the direction of the center axis 306. For purposes of this disclosure, any portion of the head portion 302 that is outside of the dotted lines 308 is defined as "offset" or eccentric to the center axis 306. As can be seen most clearly in FIG. 3B, the non-threaded head 302 includes a first portion 312 of the head 302 that is substantially within boundary lines 308 and a second portion 314 of the head portion 302 that is outside of the boundary lines 308.

Looking from the perspective of FIG. 3B, the boundary lines 308 are generally symmetrical or equal distance from the center axis 306 in a direction 310 which is normal or transverse to the center axis. Thus, for purposes of this disclosure, the second portion 314 of the head portion 302 that is outside of the boundary lines 308 is defined as an offset portion 314 from the center axis. A transition or blended surface 317 allows for the smooth transition between the surface of the elongated body portion 304 and the offset anchor head portion 314.

In certain embodiments a proximal end 316 of the anchor 300 contains a tool engagement surface 318 that is angled with respect to the normal direction 310. In certain embodiments, the tool engagement surface 318 may have engagement features, such as aperture 320 (see FIG. 3A) for engaging with various embodiments of insertion instruments and tools as will be explained below. In the illustrative embodiment, the longitudinal axis of the aperture 320 may be angled with respect to the center axis 306.

As can be best seen in FIGS. 3C and 3D, a distal end 322 of the anchor 300 is designed to penetrate and be pushed through a boney structure. Consequently, at the distal end 322 the cross-sectional area of the body portion 304 is significantly reduced which also reduces the force necessary to push the distal end 322 through the boney structure. In the illustrative embodiment as best seen in FIG. 3C, the distal end 322 has a generally semi-circular or horseshoe shaped cross-sectional area and is similar in cross sectional shape to the embodiment illustrated in FIGS. 1E through 1H described above.

The primary difference between the anchor 300 and the anchor 100 is the addition of an opposing step 340 positioned along the body portion 304 as illustrated in FIGS. 3A, 3B and 3D. In certain embodiments, the opposing step 340 is on a side of the longitudinal axis 306 opposite from or opposing the offset head portion 314. As will be explained below, the opposing step 340 facilitates the centering or positioning of the anchor 300 within an aperture of an implant (not shown) when the body portion 304 is pushed through the aperture. Once the opposing step 340 clears the aperture, the opposing step 340 when combined with the offset head portion 314 allows for a greater shift of the boney element in the direction 310 when the anchor head 302 is fully seated within the implant (not shown).

Figure 4A:
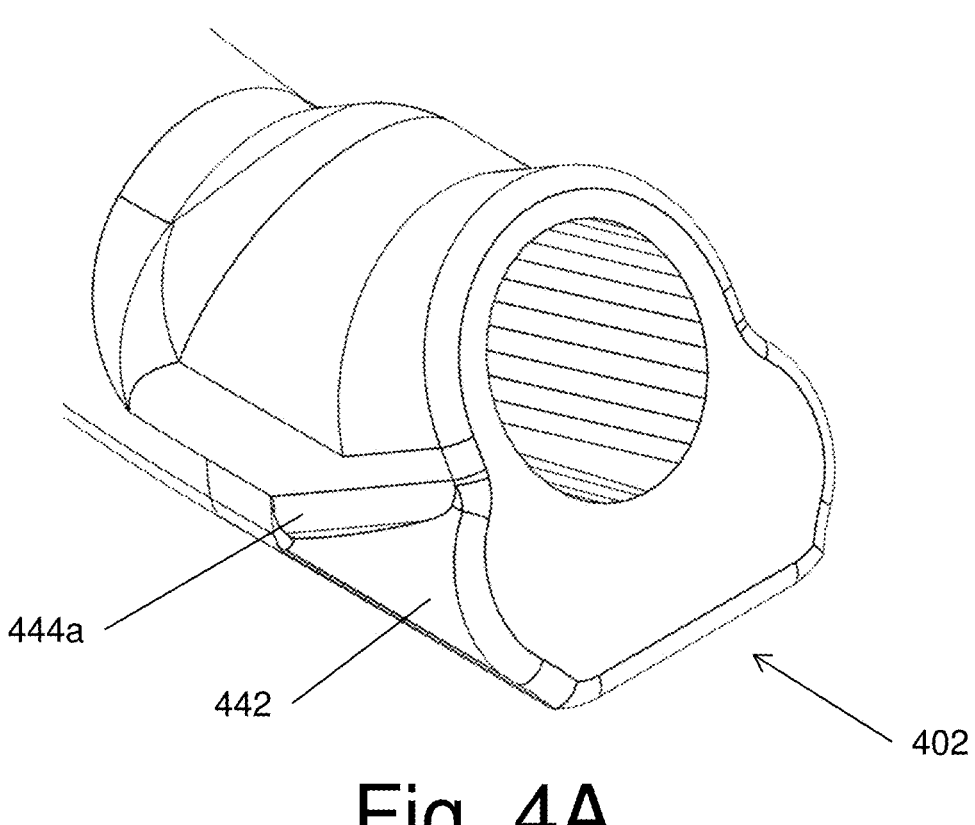
FIG. 4A is a detailed top perspective view of an alterna-tive aspect of a non-threaded head which could be used in any aspect of the anchors disclosed herein.
Figure 4B:
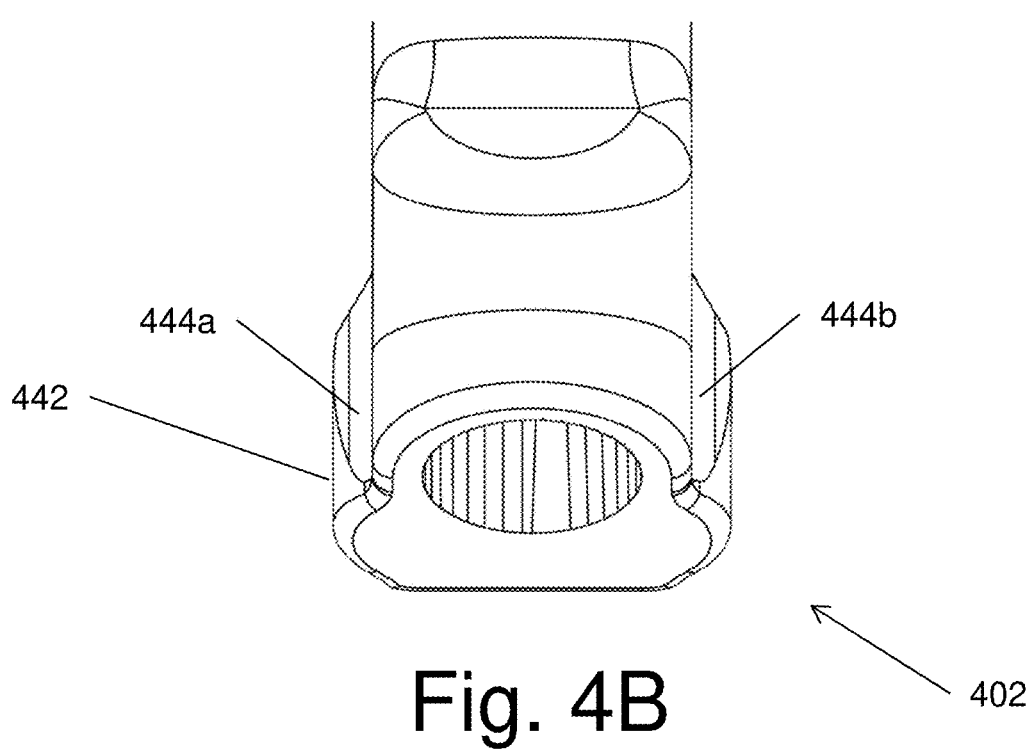
FIG. 4B is a top view of the non-threaded head in FIG. 4A.

An alternative embodiment an anchor head 402 is illustrated in FIGS. 4A and 4B. FIG. 4A is a detailed perspective view of an alternative anchor head 402 which can be used with the anchors disclosed above. FIG. 4B is a top view of the anchor head 402. In this embodiment, an exterior surface 442 of the anchor head 402 has indents or transition surfaces 444*a* and 444*b* defined therein. In certain embodiments, the indents 444*a* and 444*b* are designed to retain detents (not shown) defined within the corresponding aperture of an implant (not shown) as explained below. The combination of surfaces 442, indents 444*a* and 444*b* along with the corresponding detents in the apertures of the implant assist in sealing off the grooves in the aperture in order to limit or minimize tissue ingrowth around the aperture which might make retrieval more difficult.

Although the anchors 100 to 400 as illustrated and discussed above use a tapering horseshoe cross-sectional shape for the body portions 104, 204, and 304, any cross-sectional shape could be used and still be within the inventive aspects of the present invention. Such shapes include triangular, diamond, rectangular, circular or equilateral polygon cross-sectional shapes or a combination thereof. For instance, a triangular cross-sectional shape could be used on the body portion 104 while the head portion 102 may be largely circular in cross-sectional shape. If such shapes are used, generally the body portion will taper down from the head portion 102 to the distal end 122. In other words, the cross sectional areas of the body portions 104 will decrease as the distal end is approached.

In certain embodiments, the anchors discussed above may be fabricated from any number of biocompatible implantable materials, including but not limited to Titanium Alloys (Ti 6Al4V ELI, for example), commercially pure titanium, Chromium Cobalt (Cr—Co) and/or stainless steels. In yet other embodiments, the anchors may also be manufactured from polymer, including Carbon Fiber Reinforced Polymer ("CFRP") with a high carbon mass percentage.

In yet other embodiments, various components, for example anchor 100 may be made from nickel titanium (also known as Nitinol®) or another shape memory alloy. The anchor would have a very specific shape at a cooler temperature, such as room temperature. Once inserted into a human body, the metal would rise to a body temperature which will cause the anchor to change shape to enhance compression.

For instance, at or below room temperature a straight anchor might be inserted. At body temperature, the straight anchor turns into a curved anchor and applies additional compression or distraction. Similarly, a curved anchor could turn into a straight anchor at body temperature to enhance either compression or distraction.

A First Embodiment of an Implant

Figure 5A:
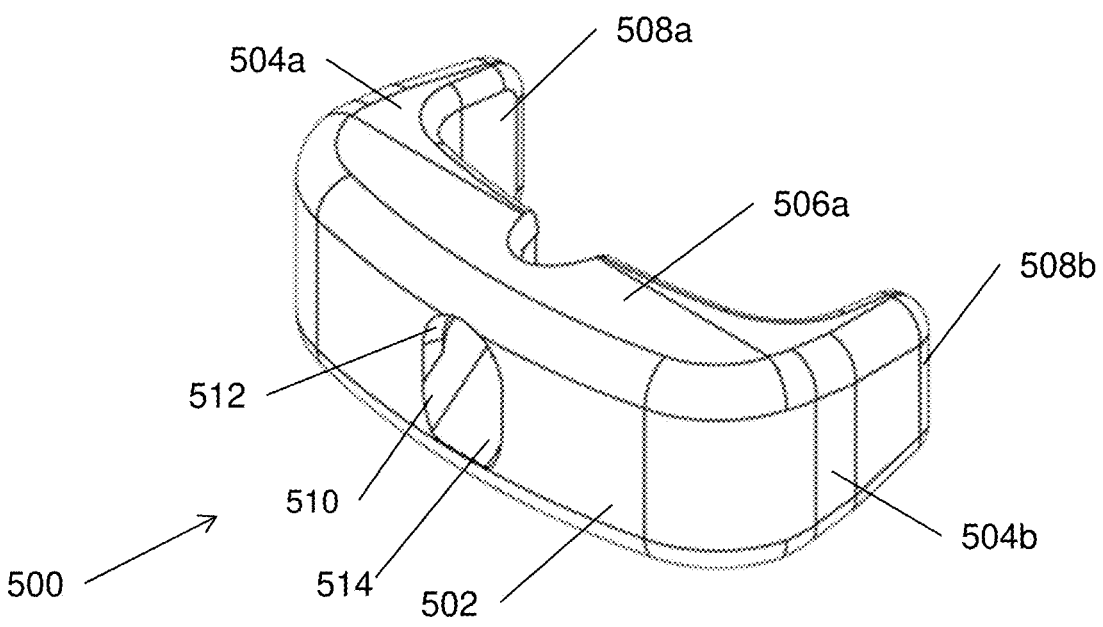
FIG. 5A is an isometric view of one embodiment of an implant which can be used with different aspects of the present invention.

Turning now to FIG. 5A, there is presented one embodiment of an interbody or interbone implant (also known in the art as a fixation plate, insert plate, or insert). The interbody implant 500 can be used with the anchors discussed above. The implants disclosed herein, such as implant 500, may be manufactured from any number of implant grade materials, including, but not limited to Titanium and Titanium Alloys, as well as Carbon Fiber Reinforced Polymer (CFRP).

In certain embodiments, the implant 500 may be generally C-shaped having a main body portion 502 with lateral side elements 504a and 504b opposing each other. There may be an upper bone engaging surface 506a and a lower bone engaging surface 506b (not shown). In certain embodiments, the implant 500 may form a structure to partially receive a cage or spacer (not shown). In certain embodiments, the lateral side elements 504a and 504b may gradually decrease or increase in height in an anterior to posterior direction with respect to a human body in order to generally conform the implant 500 to the geometry of the cage, spacer or boney body. In certain embodiments, the lateral side elements 504a and 504a may have engaging features (not shown in FIG. 5A) defined at their distal ends 508a and 508b configured to releasably engage retaining features of the cage or spacer. In other embodiments, the implant 500 may be designed to work as a stand-alone implant.

In certain embodiments, the main body portion 502 may have a central aperture 510 defined therethrough having an inner engagement feature 512 (such as an edge and/or surface). In certain embodiments, the aperture 510 may have a lower surface 514 defined therein sized to receive and engage a surface of a non-threaded anchor discussed above. In other embodiments, the aperture 510 may define a force engaging feature, such as an engagement edge or surface, which as explained below will produce a force on the head of the non-threaded anchor. In certain embodiments, the interaction of the lower surface 514 with the longitudinal shape or geometry of the non-threaded anchor defines an initial insertion trajectory for the non-threaded anchor. For purposes of this disclosure the "initial trajectory" is the path of movement of the elongated body portion (such as body portion 104) of an anchor (such as anchor 100) starting when the elongated body portion is first introduced into the aperture 510 and ending when the head portion 102 of the anchor 100 first comes into contact with the engaging features (such as engagement edge 512) forming a portion of the inside of the aperture 510.

Figure 5B:
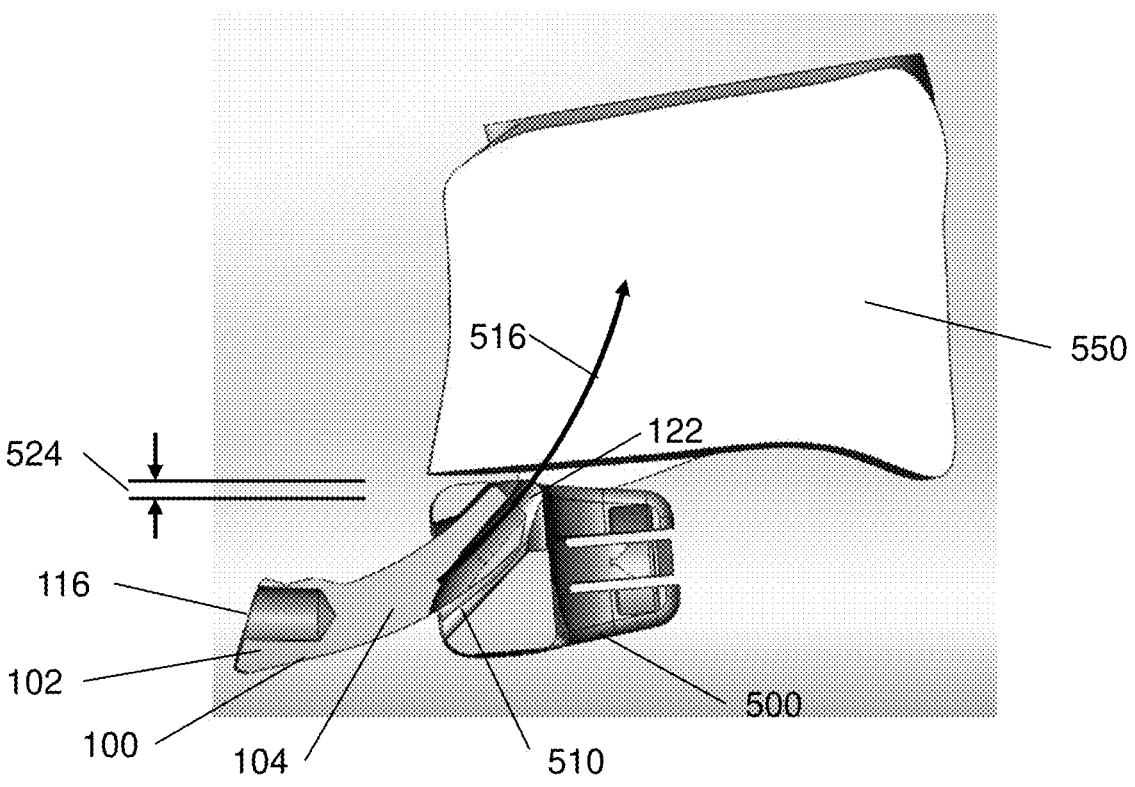
FIGS. 5B through 5F are sectional views illustrating the progression of one aspect of an anchor proceeding through the implant of FIG. 5A and a boney structure.

Methods of Use:

FIGS. 5B through 5F demonstrate a method of using one or more anchors 100 with the implant 500 to compress a boney structure 550 (such as a human vertebra) against the implant 500. For purposes of this disclosure, a boney structure many be an entire human bone or a portion of a bone that has been fragmented or otherwise separated. FIGS. 5B through 5F are cross-sectional views of the implant 500, the boney structure 550, and the anchor 100 discussed above showing different stages of interaction between these elements. In FIG. 5B, the implant 500 is positioned adjacent to the boney structure 550. For purposes of explaining the illustrated embodiment, a gap 524 (not drawn to scale) is illustrated between the boney structure 550 and the implant 500. Additionally, for purposes of illustration, an initial trajectory of elongated body portion 104 of anchor 100 can be visualized as an arrow 516.

In FIG. 5B, the distal end 122 of the body portion 104 is illustrated as having been introduced into aperture 510. In certain embodiments, a smooth non-torsional force may be applied onto the proximal end 116 of the head portion 102 to drive the first elongated body 104 through the central aperture 510, and into the boney structure 550 along the trajectory illustrated as arrow 516. In certain embodiments this non-torsional force may be a "smooth" non-torsional force as opposed to a series of impact forces. In yet, other embodiments, an impact force or a rotating force may be applied to drive the elongated body portion 104 into the boney structure 550.

Figure 5C:
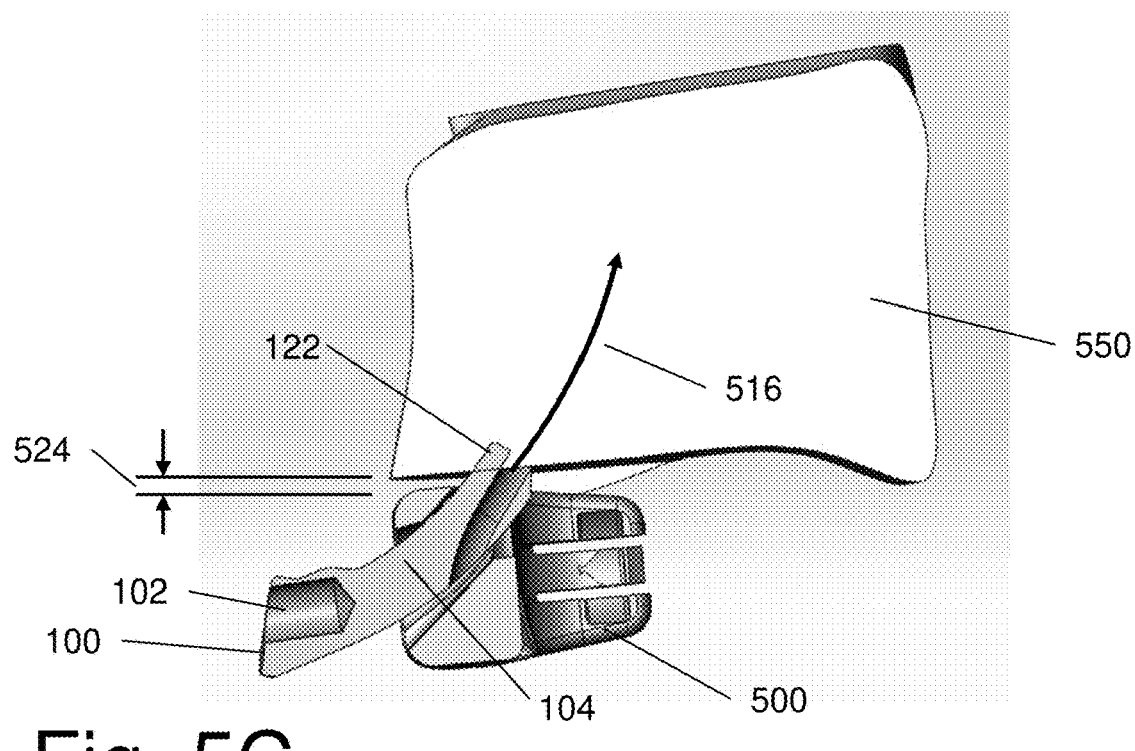
Figure 5D:
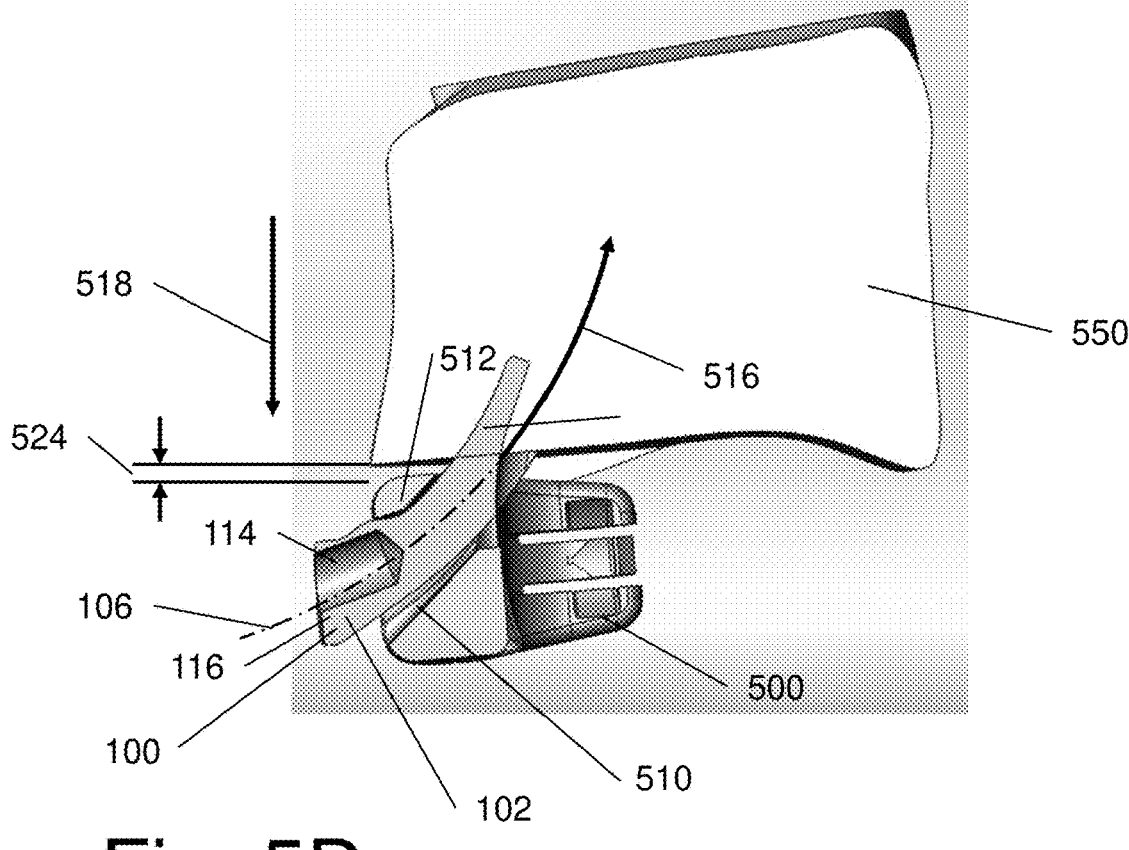

FIG. 5C illustrates the system and boney structure of FIG. 5B, but with the distal end 122 of elongated body 104 partially driven into the boney structure 550. Similarly, FIG. 5D illustrates the system and boney structure 550 of FIG. 5B, but with the elongated body 104 driven further into the boney structure 550. As can be seen in FIG. 5D, the elongated body portion 104 has been mostly driven through the aperture 510 and is still following its initial trajectory as illustrated by arrow 516.

FIG. 5D also illustrates the situation where the non-torsional force continues to be applied onto the proximal end 116 of the head 102 as the transition surface 117 of head portion 102 begins to interact with the bone engaging feature 512 of the aperture 510. The interaction between the aperture 510 and the offset portion 114 of the head portion 102 (see above) forces the head in a direction that is generally transverse to the center axis 106 of the anchor 100. The direction of this transverse movement is represented by the arrow 518. The transition surface 117 allows for a smooth transition and kinematic transverse movement. The transverse movement of the head portion 102 also causes movement of the elongated body portion 104. Because the boney structure 550 is now attached to the body portion 104 as indicated in FIG. 5D, the first boney structure 550 is also forced to move in the transverse direction as represented by arrow 518. Thus, causing the boney structure 550 to move closer to the implant 500.

Figure 5E:
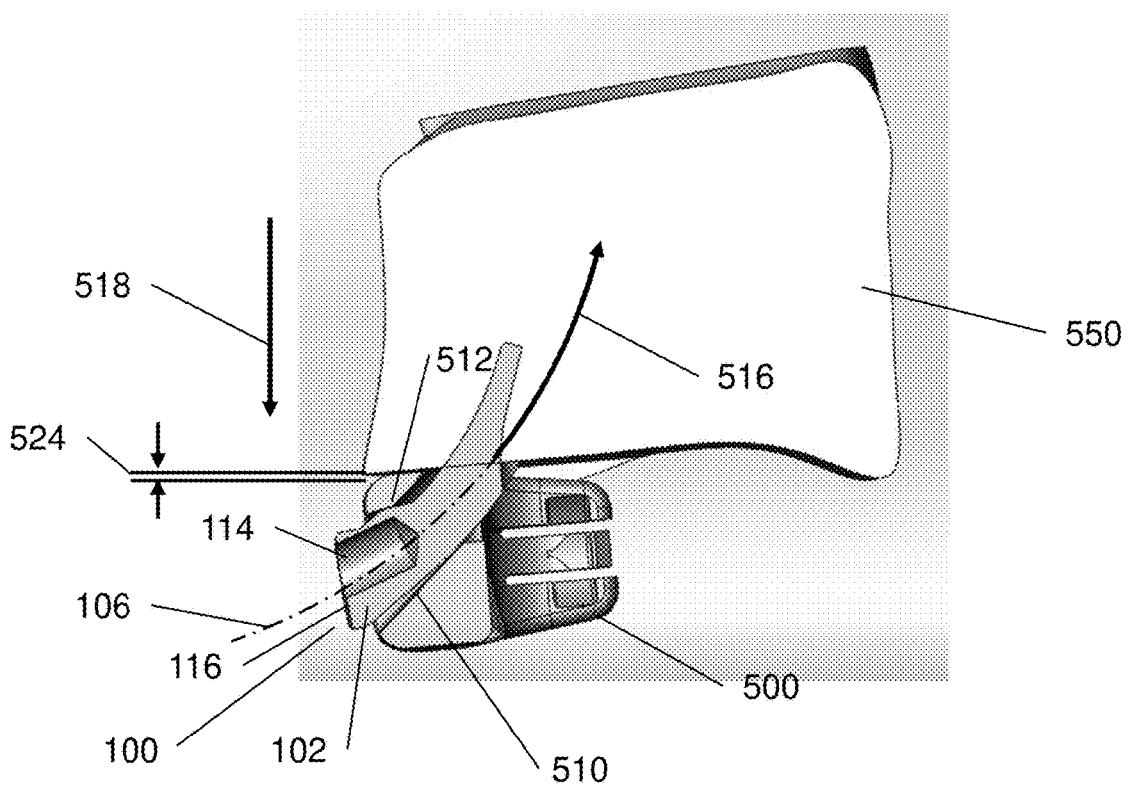

FIG. 5E illustrates the situation where the non-torsional force continues to be applied onto the proximal end 116 of the head portion 102 as the head portion is pushed further into the first aperture 510. The interaction between the inwardly sloped surface 512 of the aperture 510 and the offset portion 114 of the head portion 102 forces the head to keep moving in the transverse direction as represented by the arrow 518. As discussed above, the transverse movement of the head portion 102 also causes transverse movement of the elongated body portion 104, which causes the boney structure 550 to also move in the direction of arrow 218. Thus, causing the gap 524 to significantly narrow.

Figure 5F:
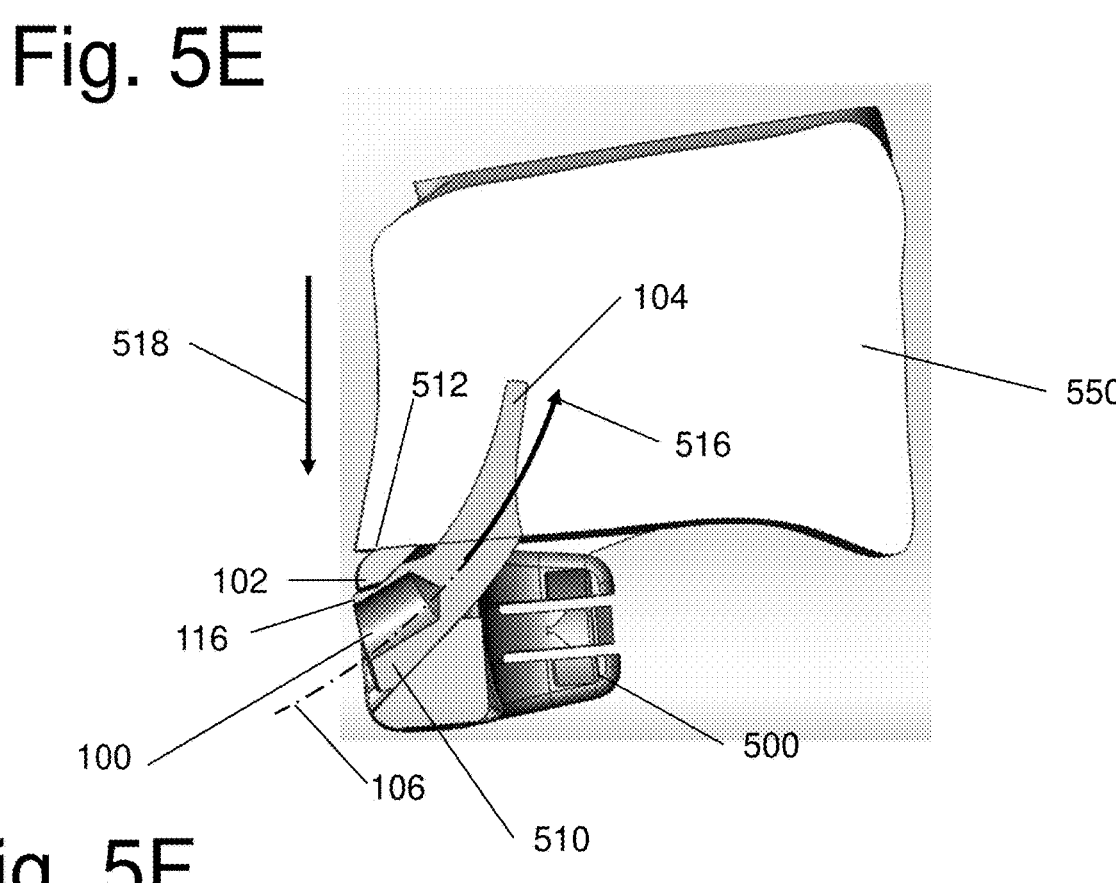

FIG. 5F illustrates the situation where the head 102 has been pushed completely into the aperture 510. As explained above, the interaction between the inwardly sloped surface 512 of the aperture 510 and the offset portion 112 of the head 102 has forced the head 102 to move transversely in the direction of the arrow 518. The transverse movement of the head portion 102 also causes transverse movement of the elongated body portion 104, which causes the boney structure 550 to compress against the implant 500. The magnitude or height of the offset of the anchor head 102 determines the amount of compression achieved.

A Second Embodiment of an Implant

Figures 6A, 6B:
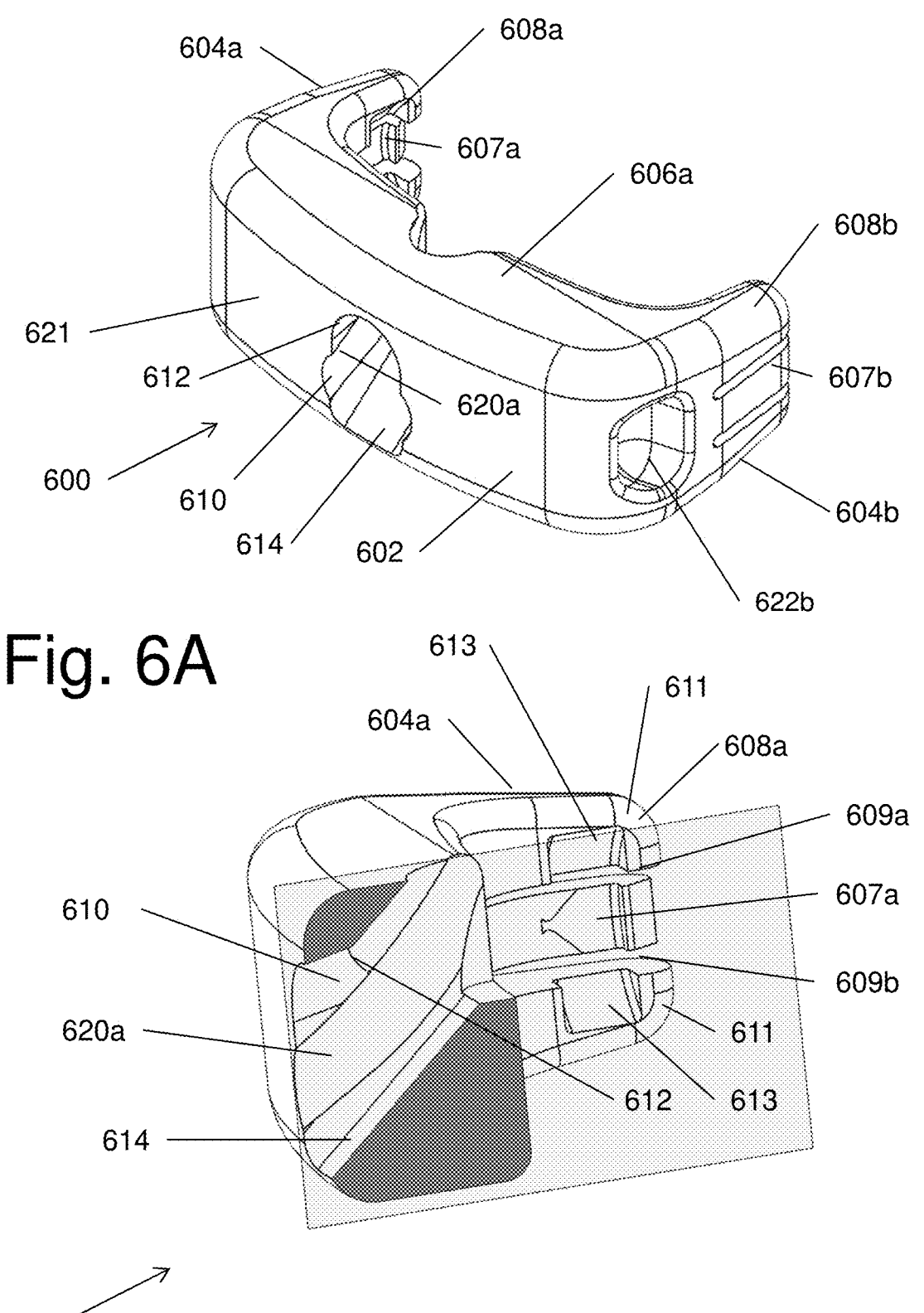
FIG. 6A is an isometric view of alternative embodiment of an implant which can be used with different aspects of the present invention.
FIG. 6B is a sectional view of the implant of FIG. 6A.

A second embodiment an implant is illustrated in FIG. 6A which is a top perspective view of an alternative implant 600 that also can be used with several embodiments of the present invention. FIG. 6B is a perspective sectional view of the implant 600 cut at its midline and orientated to illustrate details of a central aperture 610. For brevity and clarity, some of the description of those parts which are identical or similar to those described in connection with the first embodiment of the implant 500 illustrated in FIG. 5A through 5F will not be repeated here. Reference should be made to the foregoing paragraphs with the following description to arrive at a complete understanding of this second embodiment of an implant.

In certain embodiments, the implant 600 may be generally C-shaped having a main body portion 602 with lateral side elements 604a and 604b opposing each other. There may be an upper bone engaging surface 606a and a lower bone engaging surface 606b (not shown). In certain embodiments, the implant 600 may form a structure to partially receive a cage or spacer (not shown). In certain embodiments, the lateral side elements 604a and 604b may gradually decrease or increase in height in an anterior to posterior direction in order to generally conform the implant 600 to the geometry of the cage, spacer or boney body.

In certain embodiments, the lateral side elements 604a and 604a may have engagement features 607a and 607b defined at their distal ends 608a and 608b configured to releasably engage retaining features of the cage or spacer. In certain embodiments, there may be one or more longitudinal slits 609a and 609b cut within the lateral side elements 604a and 604b to provide some flexibility to the lateral side elements for flexibly engaging the cage or spacer. In certain embodiments, there may also be one or more end ribs 611 sized to interact with a catch a matching side protrusion on the cage or spacer (not shown). Immediately adjacent to the end ribs 611, there may one or more concave surfaces 613 sized to mate with a convex surface protrusion of the cage or spacer (not shown). In other embodiments, the implant 600 may be designed to work as a stand-alone implant and thus may not need the engagement mechanisms. For instance the implant 500 discussed above, is an example of stand-alone implant configuration.

In certain embodiments, an anterior side 621 of the implant 600 may have a pair of indents or side apertures 622a (not shown) and 622b defined therein and configured to receive grasping members of a delivery instrument. In the illustrated embodiment, the side apertures 622a and 622b may be generally oval in shape and may have a lip (not shown) on the inside anterior face (not shown) to allow for a complimentary rib of an insertion instrument (not shown) to conveniently grasp the implant. However any other aperture shape may be defined as appropriate.

In certain embodiments, the main body portion 602 has the central aperture 610 defined therethrough having an upper inner engagement surface 612. In certain embodiments, the aperture 610 may have a lower surface 614 defined therein sized to receive a portion of surface of a non-threaded anchor discussed above. In other embodiments, the aperture 610 may define a force engaging feature, such as an engagement edge or surface, which as explained below will produce a force on the head of the non-threaded anchor. In the illustrative embodiment, the aperture 610 has two longitudinal arcuate grooves or recesses 620a and 620b defined therein (only arcuate groove 620a is viewable in FIGS. 6A and 6B). (In other embodiments using straight anchors, the two arcuate grooves 620a and 620b would be replaced with straight grooves or recesses.) The two arcuate grooves 620a and 620b are sized to slidingly accommodate side rails on the anchor, such as side rails 230a and 230b of the anchor 200 discussed above. The interaction between the side rails 230a and 230b with the arcuate grooves 620a and 620b may be used to guide the anchor 200 in a non-centered insertion location.

In certain embodiments, the interaction of the arcuate grooves 620a and 620b with the corresponding side rails 230a and 230b and longitudinal shape or geometry of the non-threaded anchor also defines a portion of insertion trajectory for the non-threaded anchor. In other embodiments, the arcuate grooves 620a and 620b may be disposed about the aperture 610 in any desired configuration and may define any insertion trajectories as appropriate. In the example embodiment depicted in FIGS. 6A and 6B, the arcuate grooves 620a and 620b are defined in opposing sides around the center of aperture. It should be noted that this configuration of arcuate groove 620a and 620b locations and is merely an example, and the scope of this disclosure should not be limited thereto to the illustrative embodiments.
Method of Use:

FIGS. 6C through 6M demonstrate a method of using one or more anchors 200 with the implant 600 to compress the boney structure 550 against the implant 600. In FIGS. 6C through 6M, the implant 600 is positioned adjacent to the boney structure 550. FIGS. 6C, 6E, 6G, 6J, and 6L are a series of cross-sectional illustrations of the implant 600, the boney structure 550, and the anchor 200 cut at the mid-plane of the implant 600 and anchor 200 to show the progression of the anchor 200 into the boney structure 550. In contrast, FIGS. 6D, 6F, 6H, 6K, and 6M are cross-sectional illustrations of the implant 600, the boney structure 550, and the anchor 200 cut to one side of the mid-plane to show the interaction of the side rails 230a-230b projecting from the anchor 200 with that of the arcuate grooves 620a-620b (see FIGS. 2A to 2C) defined within the aperture 610 as the anchor 200 progresses into the boney structure 550.

Figure 6C:
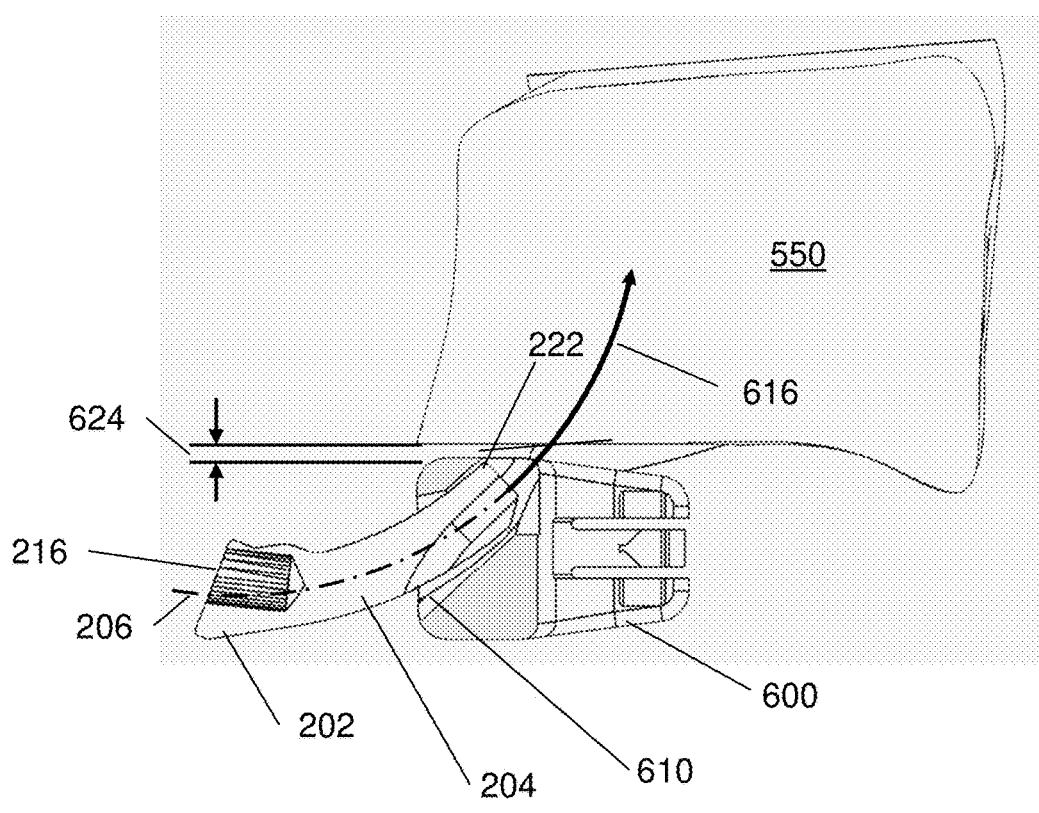
FIGS. 6C, 6E, 6G, 6J, 6L are a series of section views cut at a mid-plane illustrating the progression of one aspect of an anchor proceeding through the implant of FIG. 6A and into a boney structure.

In FIG. 6C, the distal end 622 of the body portion 204 is illustrated as having been introduced into aperture 610. For purposes of explaining the illustrated embodiment, a gap 624 (not drawn to scale) is illustrated between the boney structure 550 and the implant 600. Additionally, for purposes of illustration, an initial trajectory of elongated body portion 204 of anchor 200 can be visualized as an arrow 616. In certain embodiments, a smooth non-torsional force may be applied onto the proximal end 216 of the head portion 202 to drive the first elongated body 204 through the aperture 610, and into the boney structure 550 along the initial trajectory as represented by the arrow 616. In other embodiments, an impact force may be applied to drive the elongated body 204 into the boney structure 550.

Figure 6D:
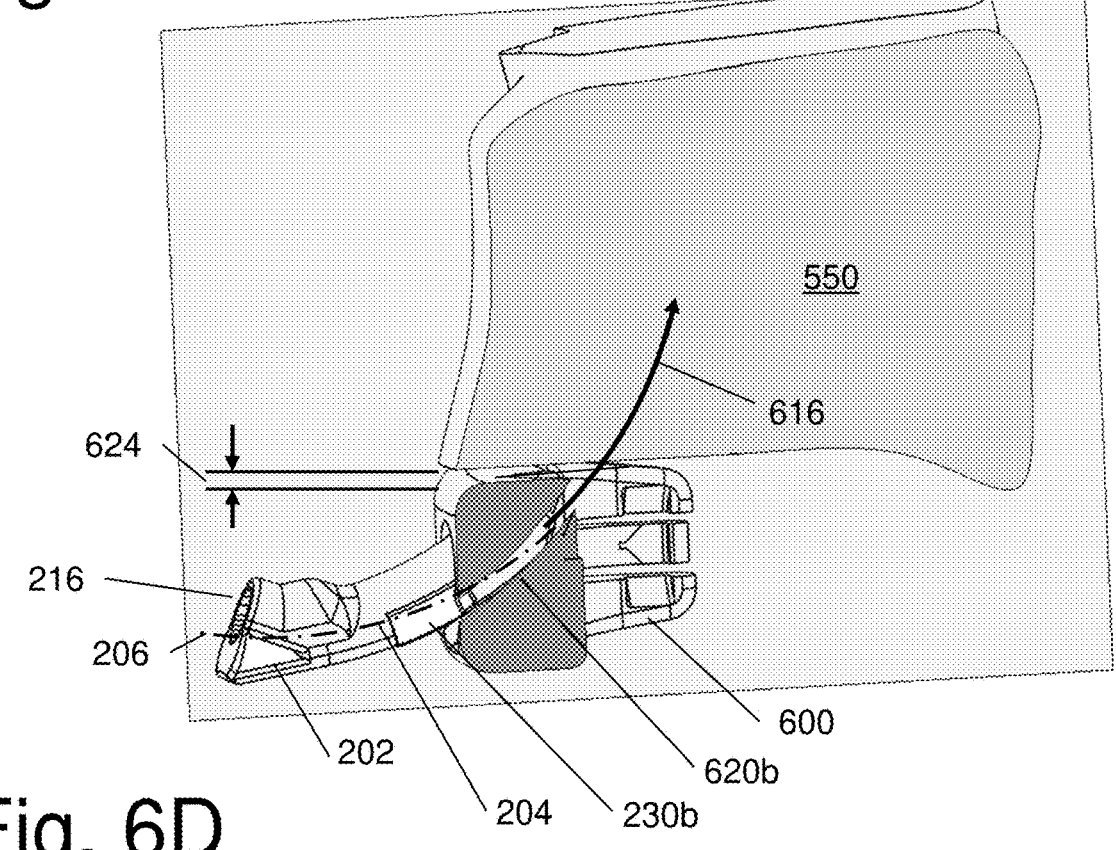
FIGS. 6D, 6F, 6H, 6K, 6M are a series of section views cut offset of the midplane illustrating the progression of one aspect of an anchor proceeding through the implant of FIG. 6A and into a boney structure.

FIG. 6D illustrates the relative position of the elements in FIG. 6C, but the sectional view of FIG. 6D is cut offset from the mid-plane to show the relationship of the side rail 230*b* with that of the arcuate grooves 620*a*-620*b* defined within the aperture 610. FIG. 6D is actually cut at the arcuate groove 620*b* and shows the side rail 230*b* as it enters the arcuate groove.

Figure 6E:
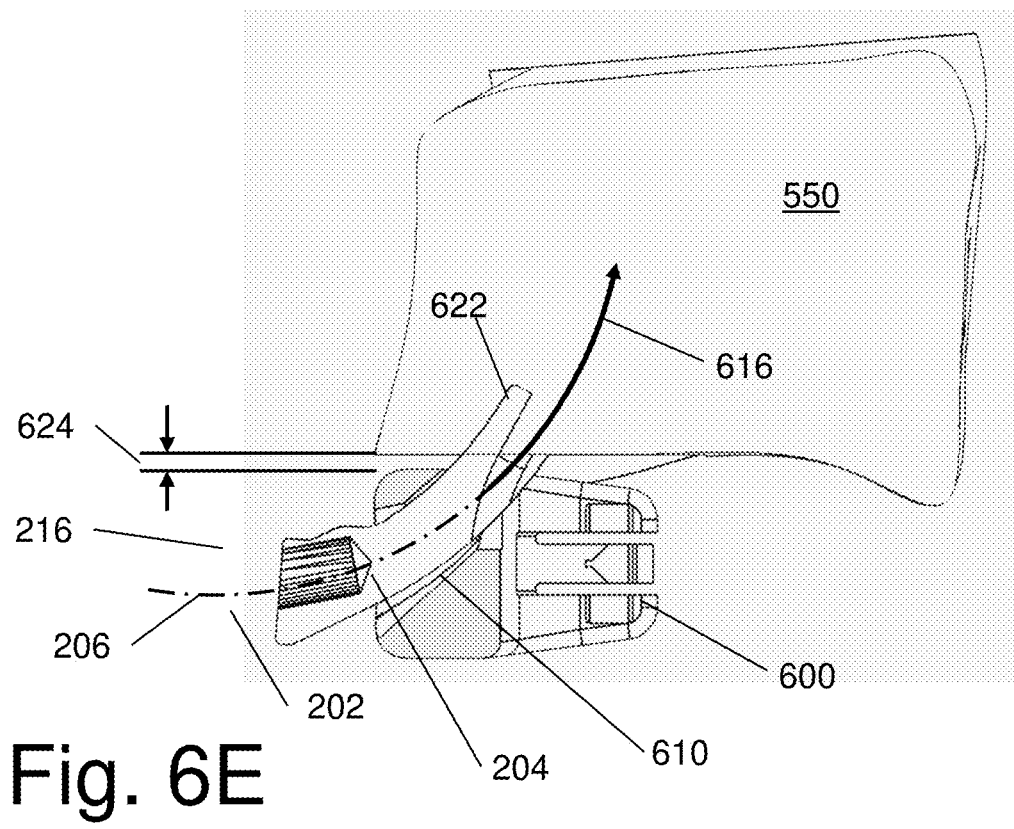

FIG. 6E illustrates the system and boney structure of FIG. 6C, but with the distal end 222 of elongated body 204 partially driven into the boney structure 550 along the initial insertion trajectory as illustrated by the arrow 616.

Figure 6F:
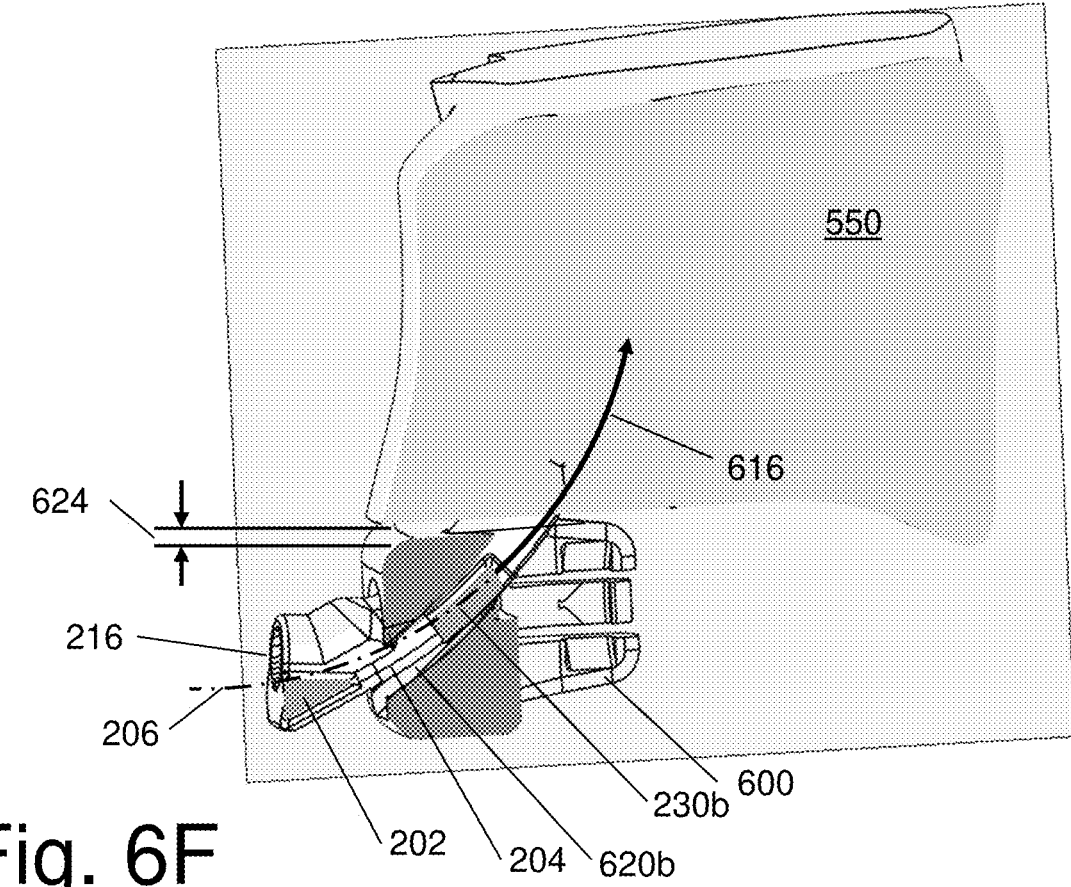

FIG. 6F illustrates the relative position of the elements in FIG. 6E, but the sectional view of FIG. 6F is cut offset from the mid-plane to show the side rail 230*b* within the arcuate groove 620*b* as the body portion 204 is pushed through the aperture 610, the arcuate groove 620*a* (not shown) and arcuate groove 620*b* guide and define the placement of the anchor 200 along the initial trajectory as illustrated by the arrow 616.

Figure 6G:
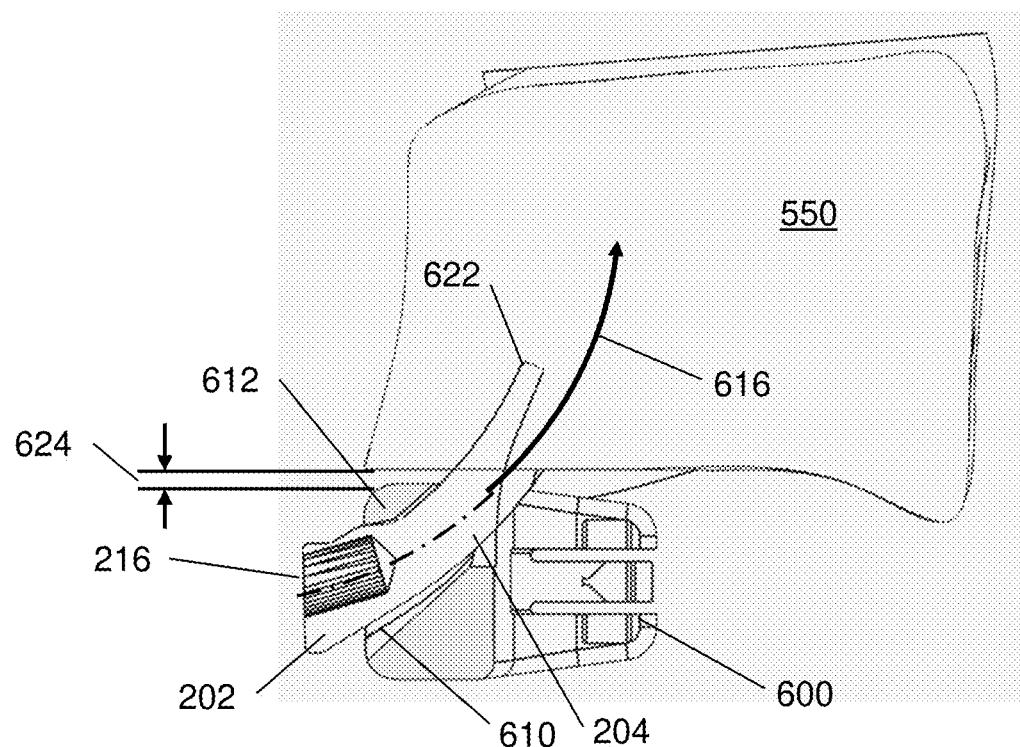

FIG. 6G illustrates the system and boney structure 550 of FIG. 6E, but with the elongated body 204 of the anchor 200 driven further into the boney structure 550. As can be seen in FIG. 6G, the elongated body portion 104 has been mostly driven through the aperture 610 and is still following its initial trajectory along arrow 616. Furthermore, the transition surface 217 of offset portion 214 of the anchor head 202 has just started to engage the engaging surface 612 of the aperture 610.

Figure 6H:
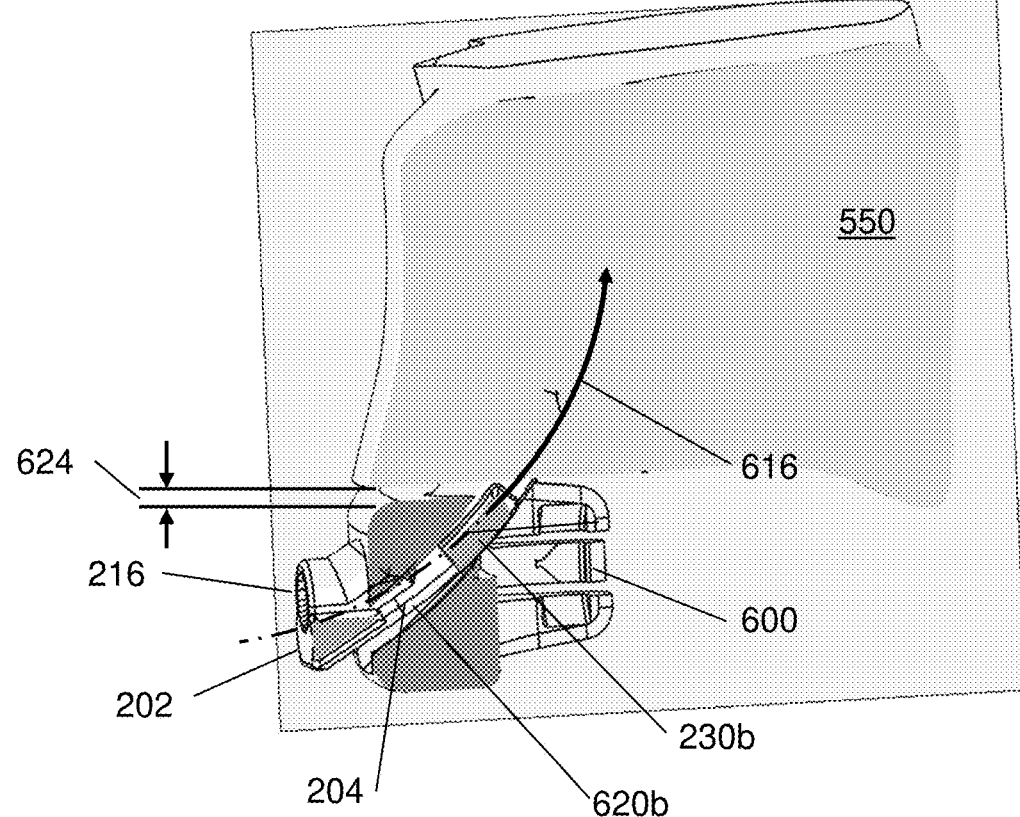

FIG. 6H illustrates the relative position of the elements in FIG. 6G, but the sectional view of FIG. 6H is cut offset from the mid-plane to show the side rail 230*b* within the arcuate groove 620*b* as the body portion 204 is pushed through the aperture 610. In FIG. 6H, the side rail 230*b* has almost been pushed entirely through the arcuate groove 620*b*. However, because a portion of the side rail 230*b* is still within the arcuate groove 620*b*, the anchor body 204 is still following the initial trajectory as illustrated by the arrow 616.

Figure 6J:
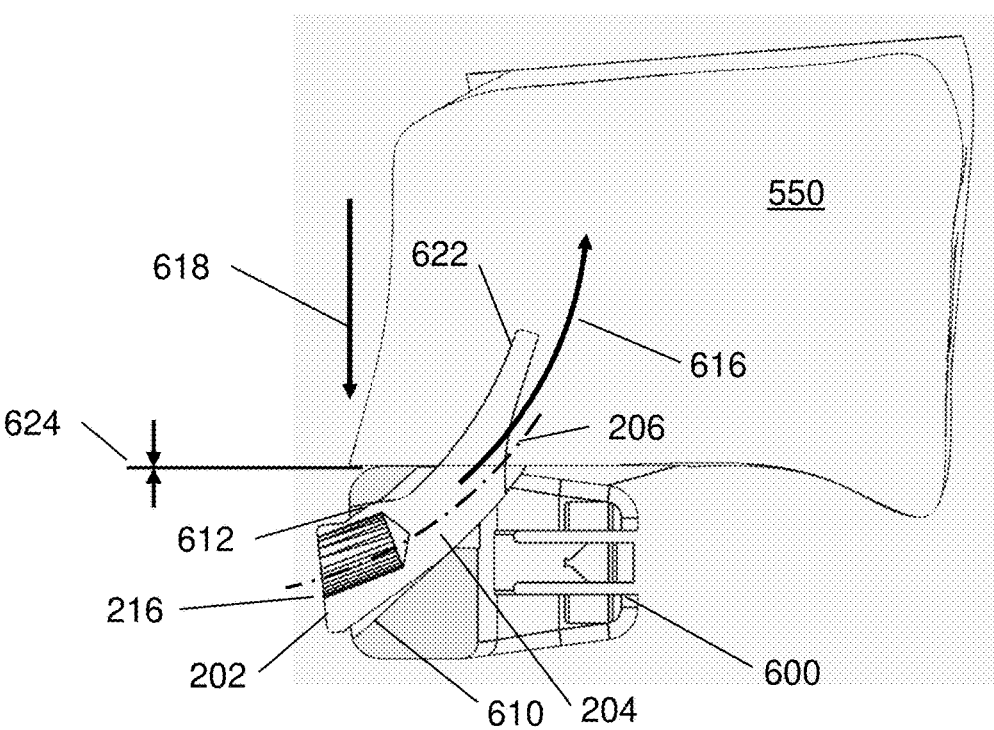

FIG. 6J illustrates the situation where the non-torsional force continues to be applied onto the proximal end 216 of the head 202 as the transition surface 217 of head portion 202 interacts with the bone engaging feature 612 of the aperture 610. The interaction between the aperture 610 and the offset portion 214 of the head 202 (see above) forces the head to move in direction that is generally transverse to the center axis 206 of the anchor 200. The transition surface 217 allows for a smooth transition and kinematic transverse movement. This transverse movement is in the direction of the arrow 618. The transverse movement of the head 202 also causes movement of the elongated body portion 204. Because the boney structure 550 is now attached to the body portion 204, the boney structure 550 is also forced to move in the transverse direction of the arrow 618. Thus, causing the boney structure 550 to move closer to the implant 600 which eliminates or reduces the gap 624.

Figure 6K:
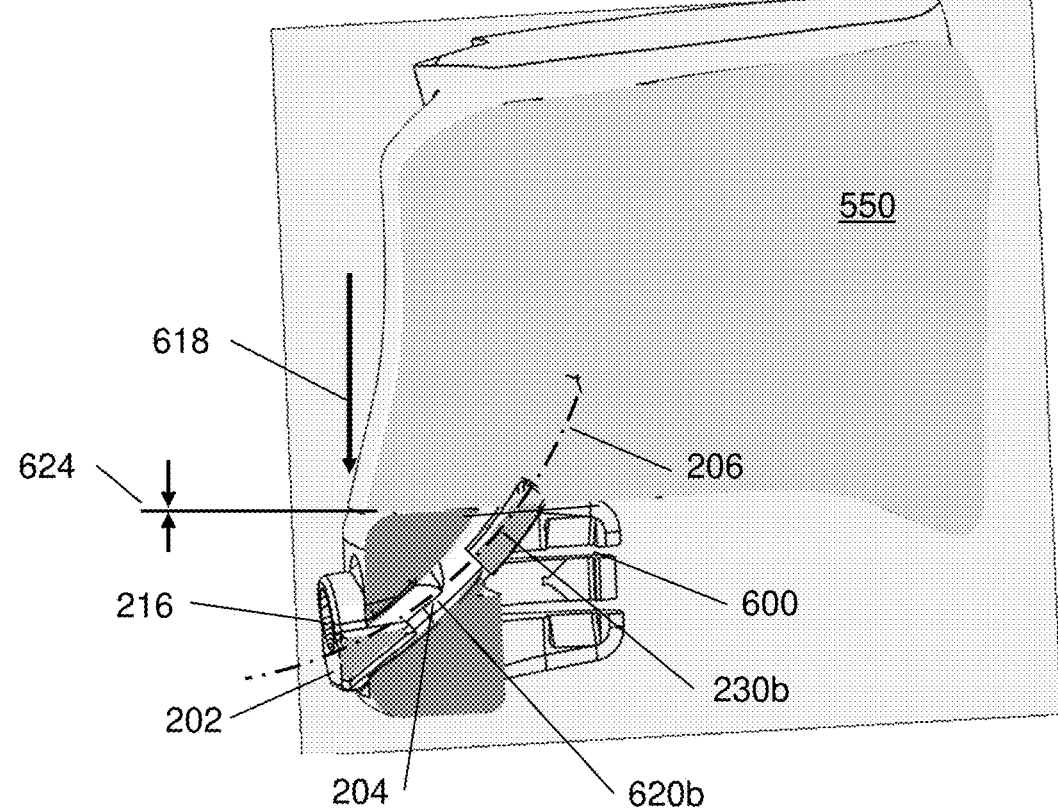

FIG. 6K illustrates the relative position of the elements in FIG. 6J, but the sectional view of FIG. 6K is cut offset from the mid-plane to show the side rail 230*b* and the arcuate groove 620*b* as the body portion 204 is pushed farther through the aperture 610. In FIG. 6K, the side rail 230*b* has been pushed entirely through the arcuate groove 620*a* which allows for the transverse shift of the body portion 204 in the direction of the arrow 618 as discussed above in reference to FIG. 6J. Thus, the movement of the elongated body portion 204 no longer follows the initial insertion trajectory along arrow 618 because of this transverse shift with respect to the trajectory. In other words, the trajectory of the anchor 200 with respect to the implant 600 starts as the "initial trajectory" and then shifts with respect to the aperture 610. Once the shift occurs, the trajectory of the anchor 200 within the boney structure 550 remains fixed, and the anchor 200 and the boney structure 550 shift due to the force of the implant aperture on the anchor head 202. In other words, the anchor 200 moves transversely off the initial trajectory (within the aperture) but the anchor 200 and boney structure 550 now move together.

Figure 6L:
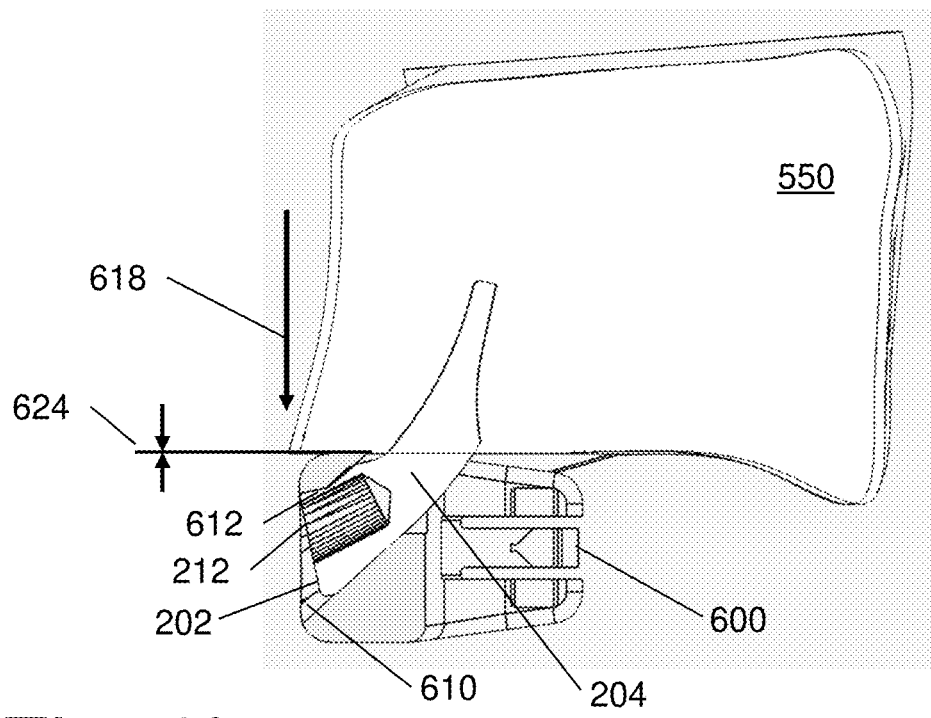

FIG. 6L illustrates the situation where the head 202 has been pushed completely into the aperture 610. As explained above, the interaction between the inwardly sloped surface 612 of the aperture 610 and the offset portion 212 of the head 202 has forced the head 202 to move transversely in the direction of the arrow 618. The transverse movement of the head 202 also causes a transverse movement of the elongated body portion 204, which causes the boney structure 550 to compress against the implant 600.

Figure 6M:
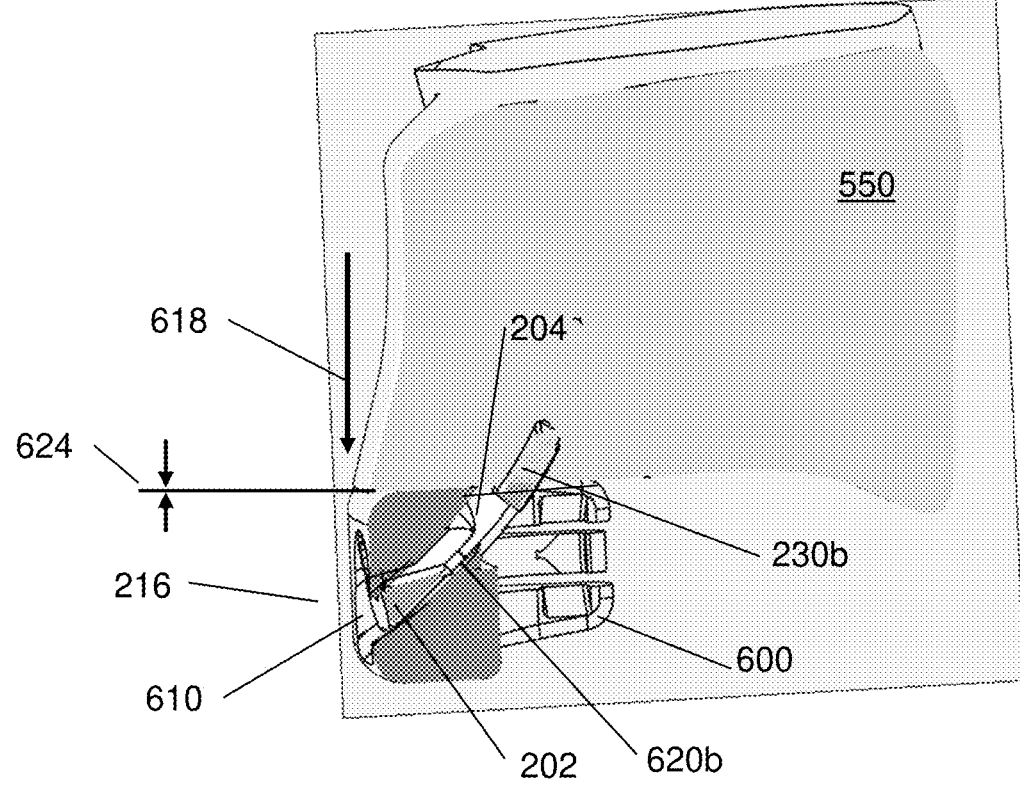

FIG. 6M illustrates the relative position of the elements in FIG. 6L, but the sectional view of FIG. 6K is cut offset from the mid-plane to show the side rail 230*b* and the arcuate groove 620*b* as the body portion 204 is pushed farther through the aperture 610. In FIG. 6M, the side rail 230*b* has been pushed entirely through the arcuate groove 620*a* and into the boney structure 550 and the gap 624 has been eliminated as the boney structure is pressed against the implant 600.

Figure 6N:
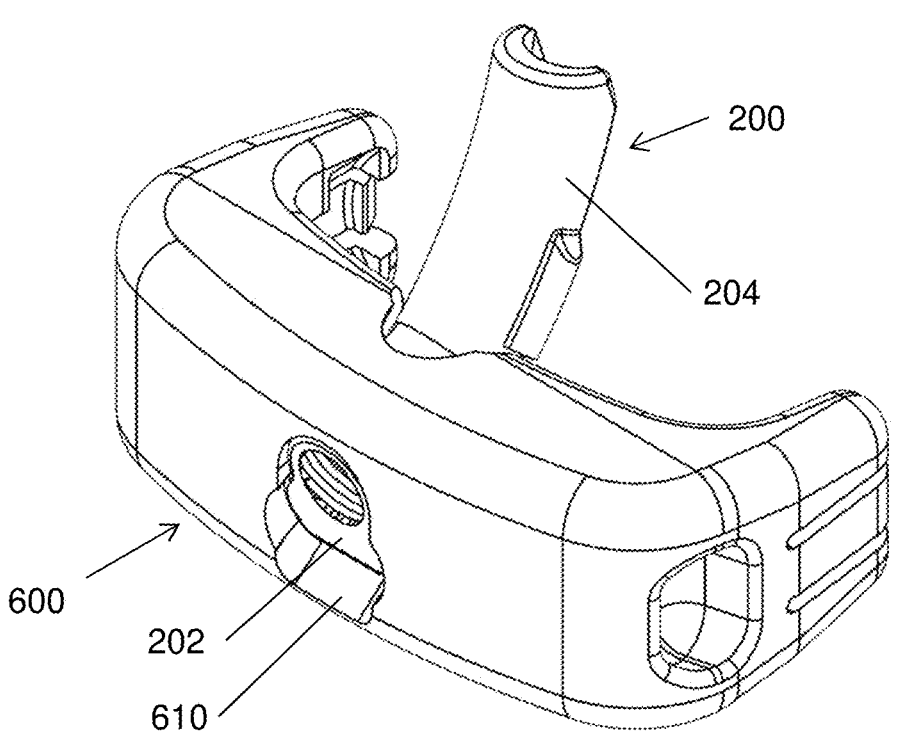
FIG. 6N is an isometric view of the implant of FIG. 6A with an anchor fully inserted into its central aperture.

FIG. 6N is an isometric view of the implant 600 with the anchor 200 is in fully inserted position. In FIG. 6N, the anchor 200 has been positioned such that the head portion 202 is fully inserted into the aperture 610 and most of the body portion 204 is now outside of the aperture.

A Third Embodiment of an Implant

Figure 7A:
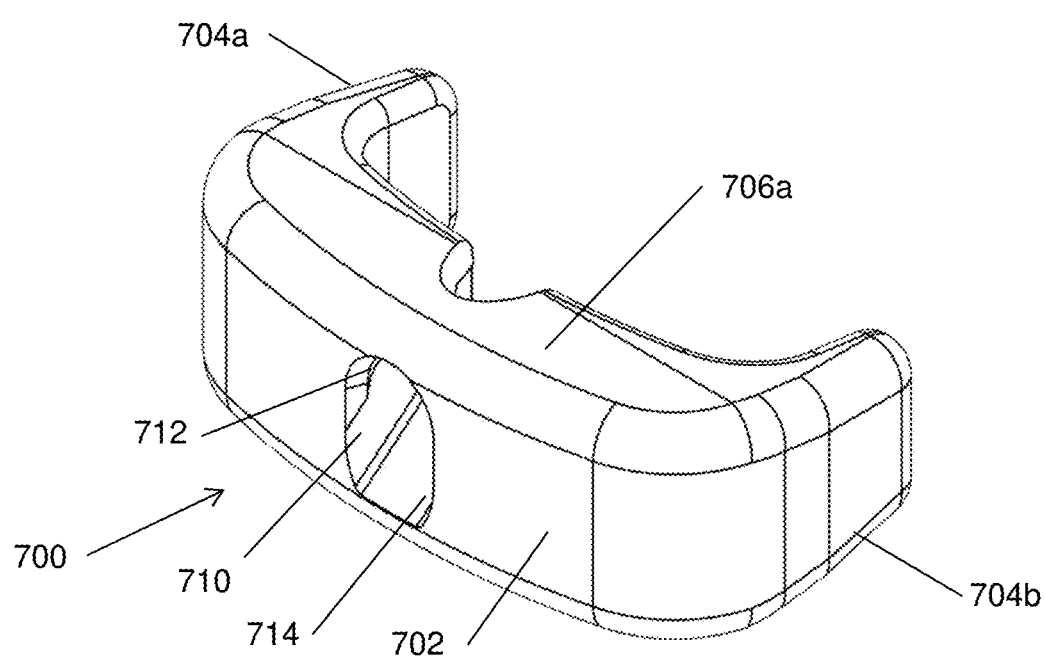
FIG. 7A is an isometric view of alternative embodiment of an implant which can be used with different aspects of the present invention.
Figure 7B:
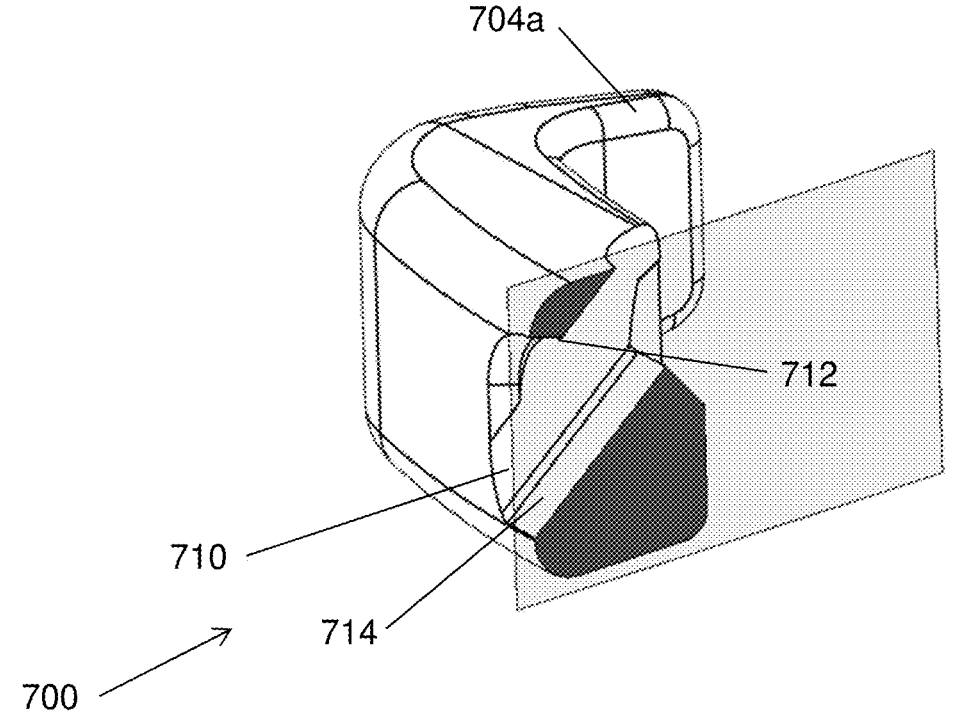
FIG. 7B is a sectional view of the implant of FIG. 6A.

A third embodiment an implant is illustrated in FIG. 7A which is a top perspective view of an alternative implant 700 which also can be used with several embodiments of the present invention. FIG. 7B is a perspective sectional view of the implant 700 cut at its midline and orientated to illustrate details of a central aperture 710. For brevity and clarity, some of the description of those parts which are identical or similar to those described in connection with the embodiments described above will not be repeated here. Reference should be made to the foregoing paragraphs with the following description to arrive at a complete understanding of this second embodiment of an implant.

In certain embodiments, the implant 700 may be generally C-shaped having a main body portion 702 with lateral side elements 704*a* and 704*b* opposing each other. There may be an upper bone engaging surface 706*a* and a lower bone engaging surface 706*b* (not shown). In certain embodiments, the implant 700 may form a structure to partially receive a cage or spacer (not shown). In certain embodiments, the lateral side elements 704*a* and 704*b* may gradually decrease or increase in height in an anterior to posterior direction in order to generally conform the implant 700 to the geometry of the cage, spacer or boney body.

In other embodiments, the implant 700 may be designed to work as a stand-alone implant and thus may not require the engagement mechanisms. In certain embodiments, the main body portion 702 has the central aperture 710 defined therethrough having an upper inner engagement surface 712 and a lower engagement surface 714 defined therein sized to receive a portion of surface of a non-threaded anchor discussed above. In other embodiments, the aperture 710 may define a force engaging feature, such as an engagement edge or surface, which as explained below will produce a force on the head of the non-threaded anchor. The interaction between the lower engagement surface 714 of the implant 700 and an engagement surface of an anchor, such as anchor 300 discussed above, may be used to guide the anchor 300 in a non-centered insertion location.

Turning briefly back to FIG. 3D above, there is a perspective view showing a lower surface of the anchor 300. As previously described, anchor 300 includes a step or engaging surface 340 running from a point close to its distal end 322 to a point where the longitudinal body portion 304 begins to transition into the offset head portion 314. Thus, in this embodiment of an anchor, almost the entire longitudinal body portion 304 includes the step 340. Furthermore, the step 340 is located on an opposing side from the offset head portion 314.

Thus, in certain embodiments, the interaction of the lower engagement surface 714 with the step 340 of the anchor 300 and longitudinal shape or geometry of the non-threaded anchor 300 also defines a portion of an initial insertion trajectory for the non-threaded anchor 300.

Method of Use:

FIGS. 7C through 7H demonstrate a method of using one or more anchors 300 with the implant 700 to compress the boney structure 550 against the implant 700. In FIGS. 7C through 7H, the implant 700 is positioned adjacent to the boney structure 550. FIGS. 7C through 7H are a series of cross-sectional illustrations of the implant 700, the boney structure 550, and the anchor 300 cut at the mid-plane of the implant 700 and anchor 300 to show the progression of the anchor 300 into the boney structure 550.

Figures 7C, 7D:
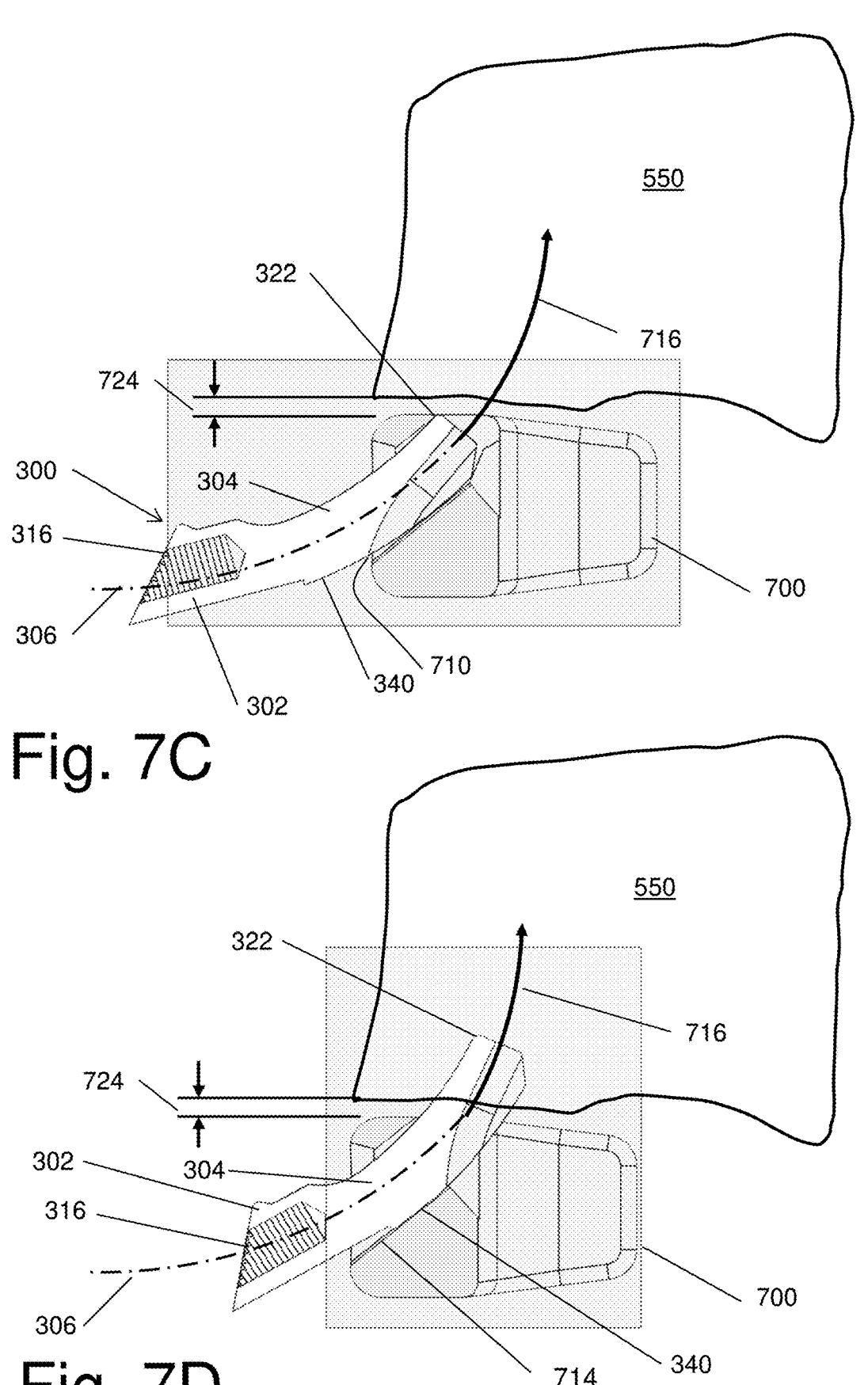
FIGS. 7C through 7G are sectional views illustrating the progression of one aspect of an anchor proceeding through the implant of FIG. 7A and into a boney structure.

In FIG. 7C, the distal end 322 of the body portion 304 is illustrated as having been introduced into aperture 710. For purposes of explaining the illustrated embodiment, a gap 724 (not drawn to scale) is illustrated between the boney structure 550 and the implant 700. Additionally, for purposes of illustration, an initial trajectory of elongated body portion 304 of anchor 300 can be visualized as an arrow 716. In certain embodiments, a smooth non-torsional force may be applied onto the proximal end 316 of the head portion 302 to drive the elongated body 304 through the aperture 710, and into the boney structure 550 along the initial insertion trajectory 716. In other embodiments, an impact force may be applied to drive the elongated body 304 into the boney structure 550.

In FIG. 7D, the distal end 322 of elongated body 304 has been driven farther into the boney structure 550 along the initial insertion trajectory 716 via the interaction of the step 340 and the engagement surface 714.

Figure 7E:
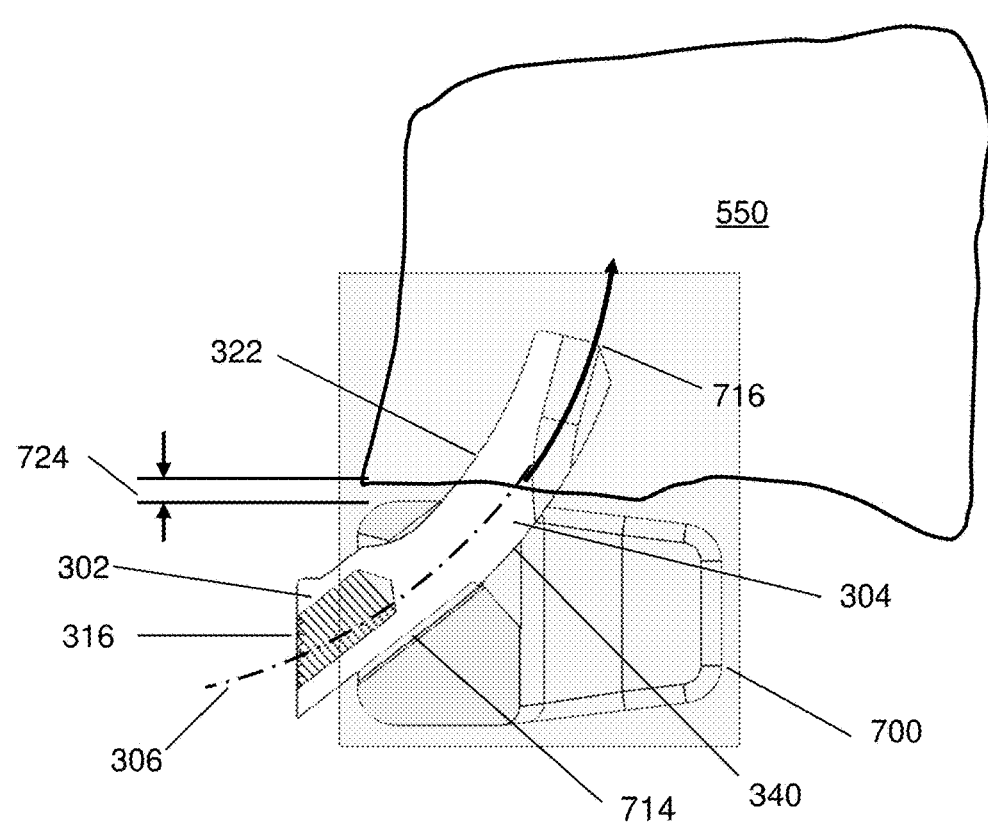

FIG. 7E illustrates a situation the elongated body 304 has been driven into the boney structure 550 until the step 340 is almost completely through the aperture 710. As illustrated, the step 340 allows the anchor 300 to be positioned within the aperture 710 in a somewhat offset manner.

Figure 7F:
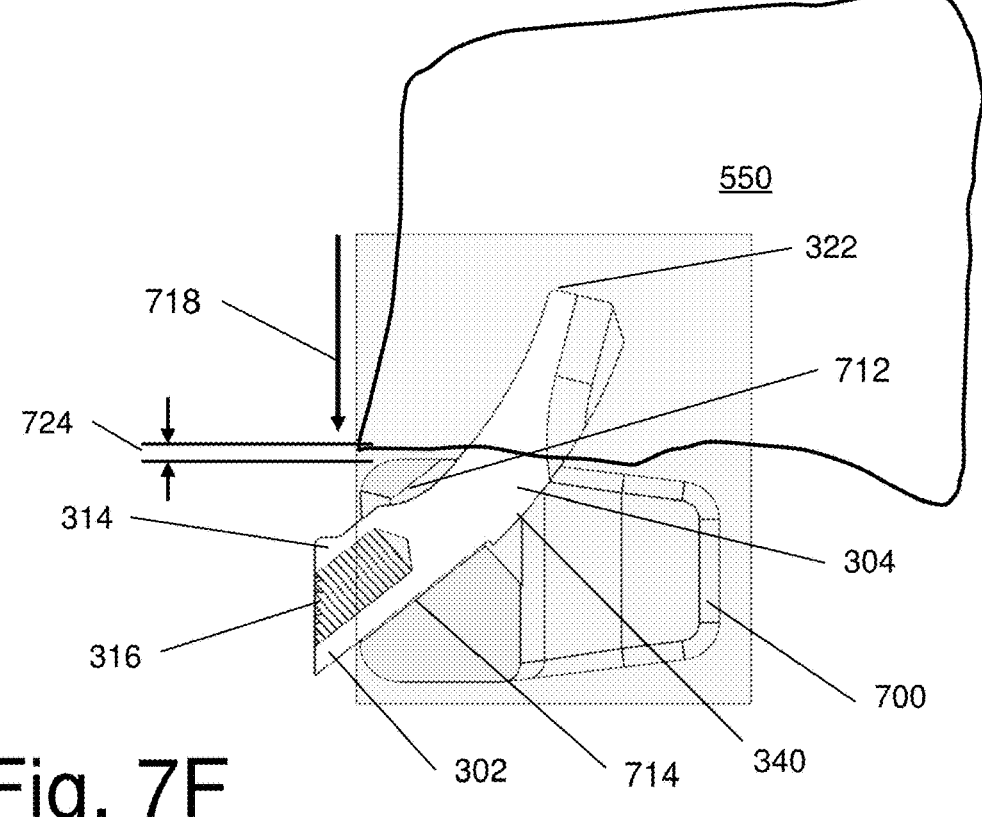

FIG. 7F illustrates the system and boney structure 550 of FIG. 7E, but with the elongated body 304 of the anchor 300 positioned such that the step 340 is past the aperture 710. Once the step 340 is past the aperture 710, the entire anchor 300 is free to shift in a generally transverse manner as represented by the arrow 718. Additionally, in this position, the transition surface 317 of the offset portion 314 of the anchor head 302 has just started to engage the upper engaging surface 712 of the aperture 710. As explained above, the engagement between the engaging surface 712 and the offset portion 314 has started the head 302 to shift in a generally transverse direction as indicated by the arrow 718. This shift narrows the gap 724 between the boney structure 550 and the implant 700.

Figure 7G:
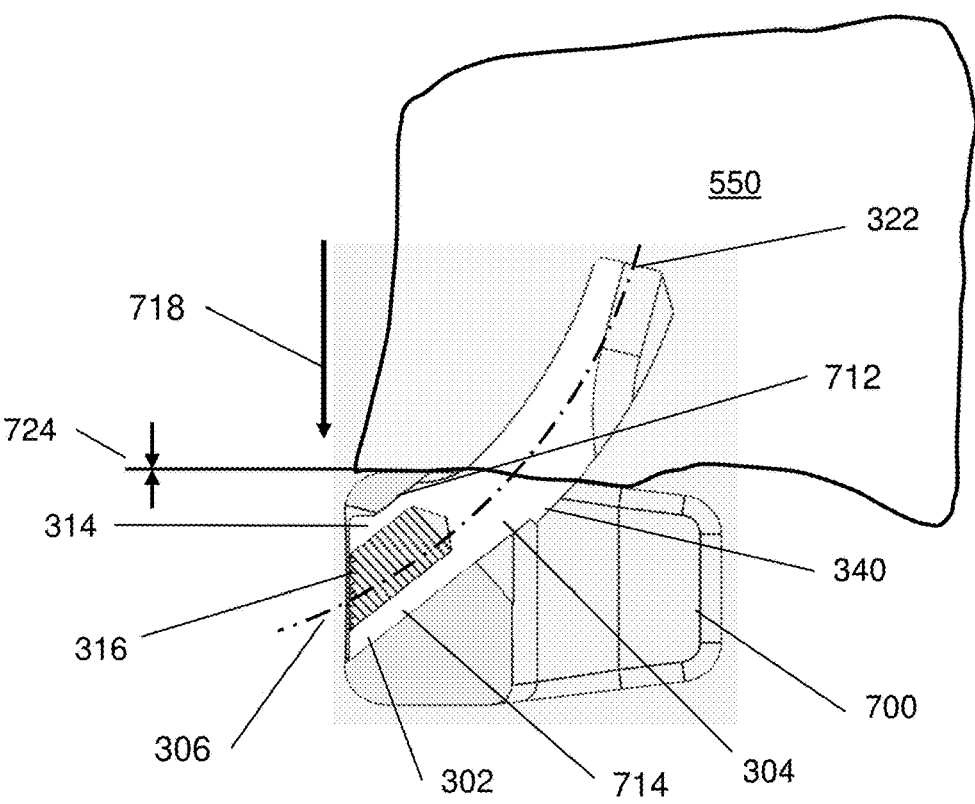

FIG. 7G illustrates the situation where the non-torsional force continues to be applied onto the proximal end 316 of the head 302 as the transition surface 317 of head portion 302 interacts with the bone engaging feature 712 of the aperture 710. The interaction between the aperture 710 and the offset portion 314 of the head 302 (see above) forces the head to move in direction that is generally transverse to the center axis 306 of the anchor 300. The transition surface 317 allows for a smooth transition and kinematic transverse movement. In the illustrated embodiment, the transverse movement is in the direction of the arrow 718. The transverse movement of the head 302 also causes movement of the elongated body portion 304. Because the boney structure 550 is now attached to the body portion 304, the boney structure 550 is also forced to move in the transverse direction of the arrow 718 which causes the boney structure 550 to compress against the implant 700.

Figure 7H:
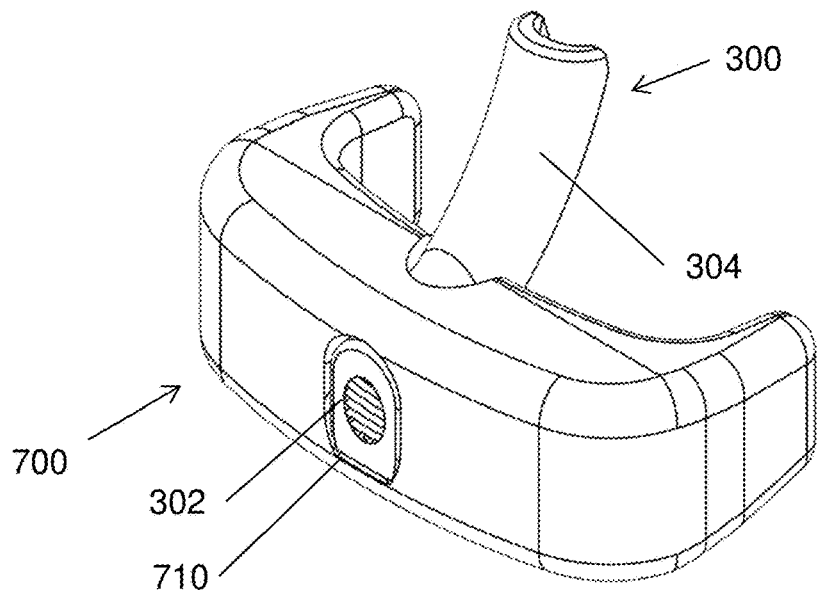
FIG. 7H is an isometric view showing the implant of FIG. 7A with an anchor fully deployed into an aperture of the implant.

FIG. 7H is an isometric view of the implant 700 with the anchor 300 in a fully inserted position and the boney structure 550 removed for clarity. In FIG. 7H, the anchor 300 has been positioned such that the head portion 302 is fully inserted into the aperture 710 and most of the body portion 304 is now outside of the aperture.

Multi-Anchor Embodiments

For purposes of simplification, the implant embodiments discussed above have illustrated and described with an implant a single anchor. However, the present invention contemplates the use of implant systems using two or more anchors. The use of two or more anchors will compress two adjacent boney structures together as explained below.

Figures 8A, 8B:
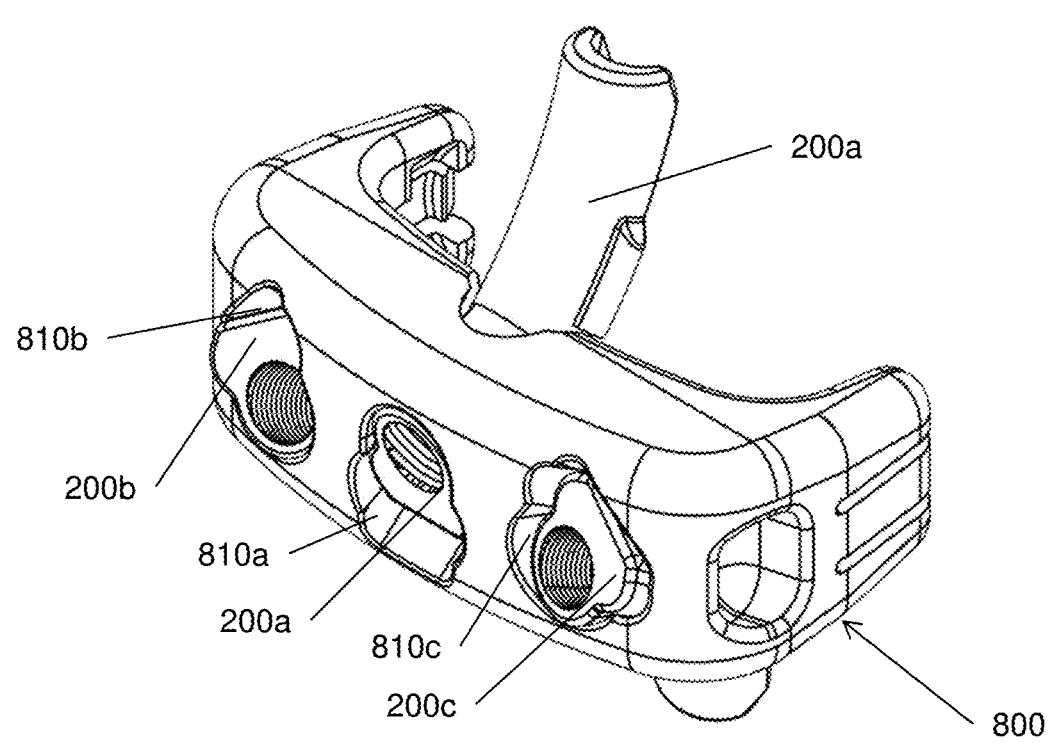
FIG. 8A is an isometric view of alternative embodiment of an implant which can be used with different aspects of the present invention.
FIG. 8B is a front view of the implant of FIG. 8A.

Three Anchor Implant:

FIG. 8A is an isometric view of an implant 800 and three anchors, such as anchor 200 discussed above. FIG. 8B is a front view of the implant 800 with the three anchors. In the illustrative embodiment, implant 800 is similar to implant 600 discussed above except that implant 800 can accommodate three anchors: 200a, 200b, and 200c. Anchors 200a, 200b, and 200c are similar to anchor 200 discussed above with the subscribe reference letters added to distinguish the anchors from one another. For brevity and clarity, a description of those parts which are identical or similar to those described in connection with the second embodiment of an implant 600 or the anchor 200 will not be repeated here. Reference should be made to the foregoing paragraphs with the following description to arrive at a complete understanding of this embodiment.

Implant 800 defines a central aperture 810a which is curved in a generally upwards manner relative to the orientation of FIGS. 8A and 8B. Additionally, the implant 800 defines two side apertures 810b and 810c which in the illustrative embodiment are curved in a generally downward direction relative to the orientation in FIGS. 8A and 8B (or in a direction that is flipped about a horizontal axis when compared to the central aperture). In certain embodiments, the side apertures 810b and 810c also are inclined relative to a vertical axis 801 and in some embodiments, the longitudinal axes of the apertures 810b and 810c converge at some point.

Similarly, the anchor 200a is illustrated as being fully inserted into the aperture 810a. Consequently, the anchor 200a is shown angled in an upwards position relative to FIGS. 8A and 8B. The anchors 200b and 200c are shown as being fully inserted into the apertures 810b and 810c, respectively. They are illustrated angled in a downwards position relative to the FIGS. 8A and 8B and their longitudinal axis are inclined and converge along vertical axis 801.

Figure 8C:
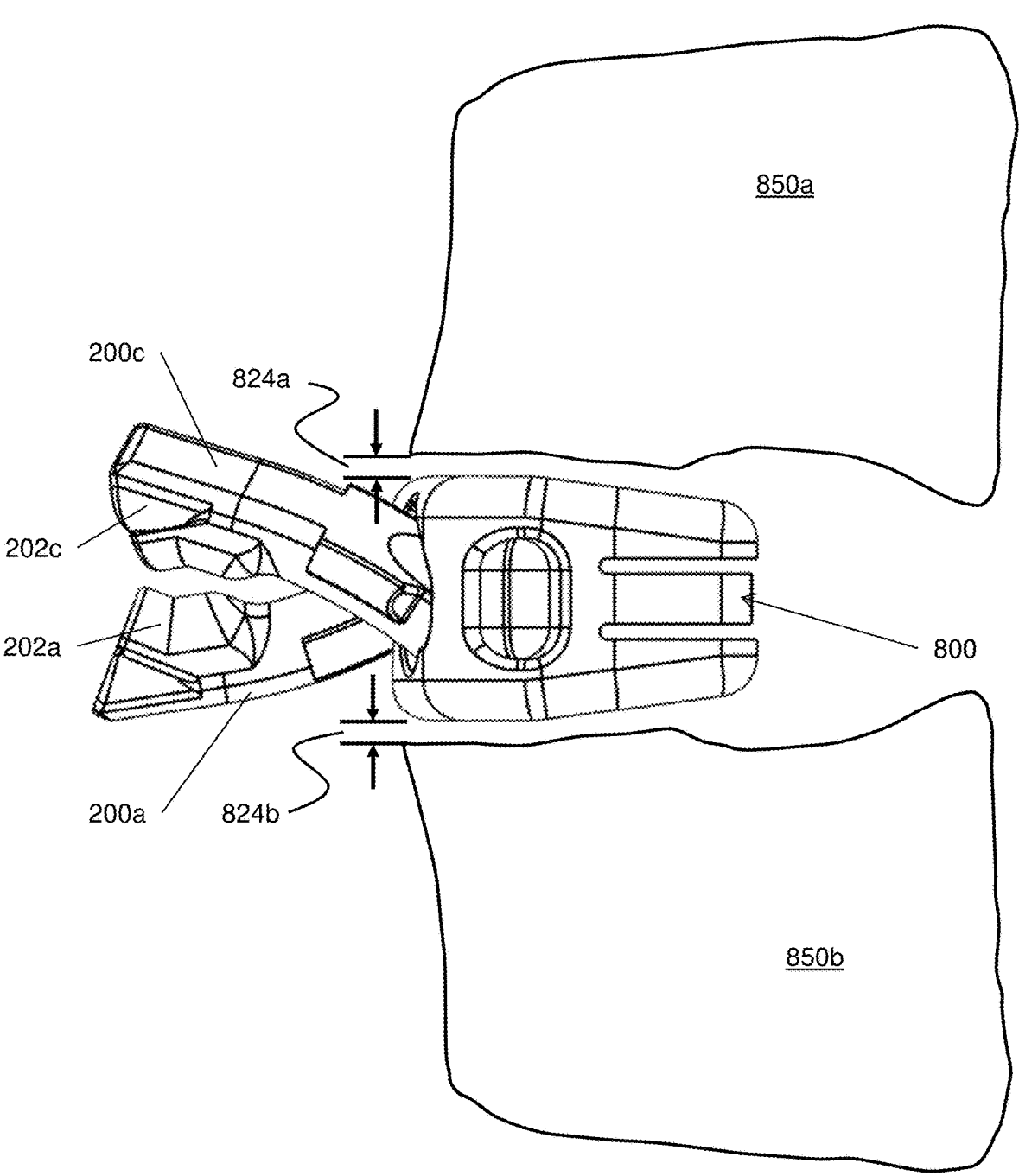
FIG. 8C is a side/sectional view of the implant of FIG. 8A with anchors in an un-deployed position.

In FIG. 8C, the implant 800 is illustrated sandwiched between two boney structures 850*a* and 850*b* (such as vertebrae of a human spine). The distal ends (not shown) of the anchors 200*a*, 200*b*, and 200*c* (anchor 200*b* is not visible in FIG. 8C because it is obscured by anchor 200*c*) are positioned within the implant 800 in a position similar to that shown in FIGS. 6C and 6D above. For purposes of explaining the illustrated embodiment, a gap 824*a* (not drawn to scale) is shown between the boney structure 850*a* and the implant 800. Similarly, a gap 824*b* (not drawn to scale) is shown on the opposing side of the implant 800 between the boney structure 850*b* and the implant.

A method of compressing boney structure 850*a* to boney structure 850*b* via the implant 800 is similar to the method discussed above in reference to FIGS. 6C through 6M except that where the previous method joined the single boney structure 550 to an implant using a single anchor, this method joins two boney structures 850*a* and 850*b* to the implant 800 using two or more anchors. For instance, when a force is applied to the head 202*a* of the anchor 200*a*, the anchor will progress as described above in reference to FIGS. 6C through 6M to close the gap 824*a* and to compress the boney structure 850*a* against the implant 800. Simultaneously, or near simultaneously, additional forces are applied to the heads 202*b* (not shown in FIG. 8C) and 202*c* of the anchors 200*b* and 200*c*, respectively. Such forces will cause the anchors 200*b* and 200*c* to penetrate the boney structure 850*b* in a manner similar to the method described above in reference to FIGS. 6C through 6M. This penetration will close the gap 824*b* and cause the boney structure 850*b* to press against the implant 800.

Figure 8D:
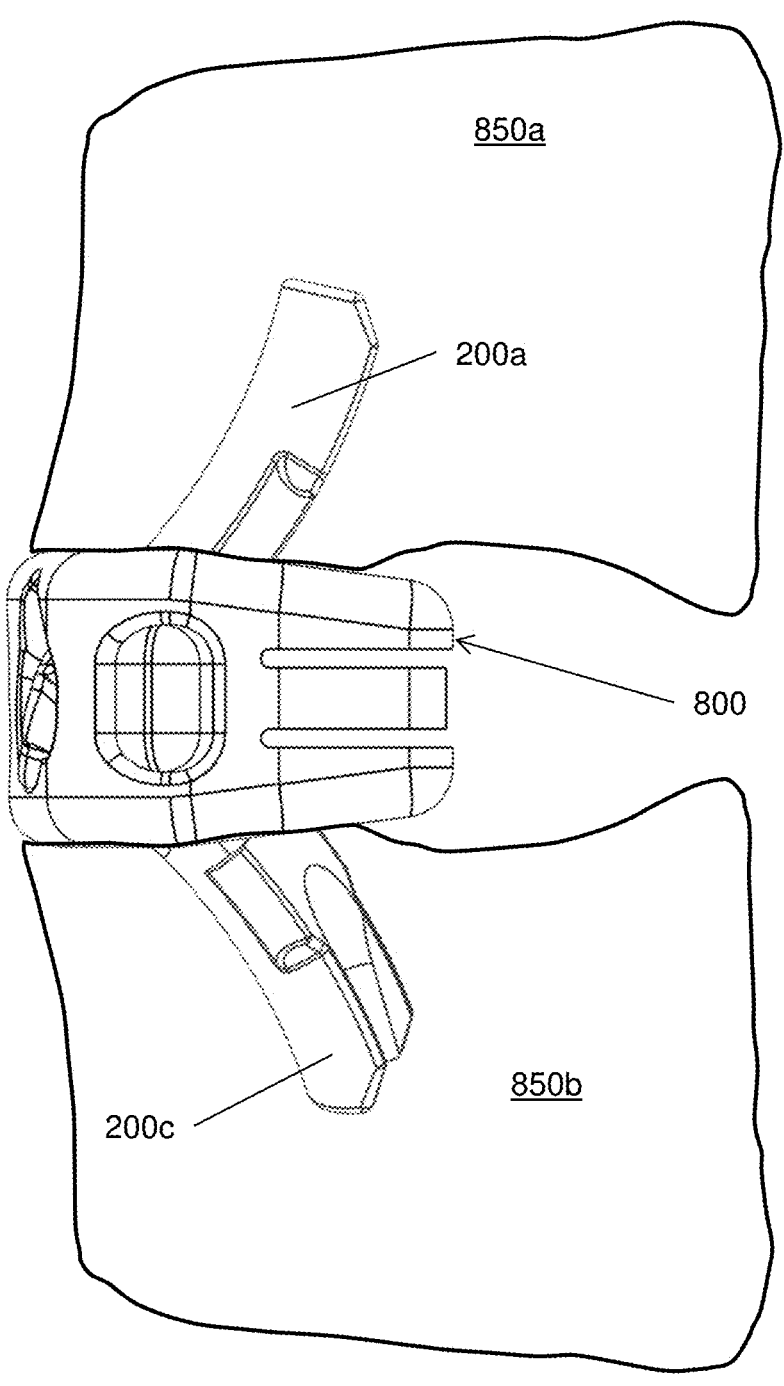
FIG. 8D is a side/sectional view of the implant of FIG. 8A with anchors in a fully deployed position.

In contrast, FIG. 8D shows the final positioning of the implant 800 with the anchors 200*a*, 200*b*, and 200*c* fully inserted into the implant and the boney structures 850*a* and 850*b* in compression against the implant 800.

Alternative Anchor Embodiments

In alternative embodiments, one or more anchors may be a traditional anchor without an offset head portion. For instance in FIGS. 8A through 8D, the anchor 200*a* may be replaced with a traditional anchor (either threaded or non-threaded) having a symmetrical head portion. Similarly, the aperture 810*a* may be replaced with a traditional concentric aperture designed to accommodate an anchor with a concentric or symmetrical head. In this alternative embodiment, the symmetrical head and concentric aperture would not cause a transverse shift as explained above. Consequently, significant compression would not occur on the "upper" side of the implant. For example in FIG. 8C, if the anchor 200*a* is replaced with a traditional anchor and the aperture 810*a* is replaced with a symmetrical aperture, then only the boney structure 850*b* will significantly compress against the implant 800. The boney structure 850*a* only compresses against the implant 800 in as much as a traditional anchor would allow with any transverse shifting.

While the above example uses anchors 200 with the three aperture implant 800, implants may have one, two, three, four or more apertures and the corresponding number of anchors and still be within the scope of this invention.

Figure 9:
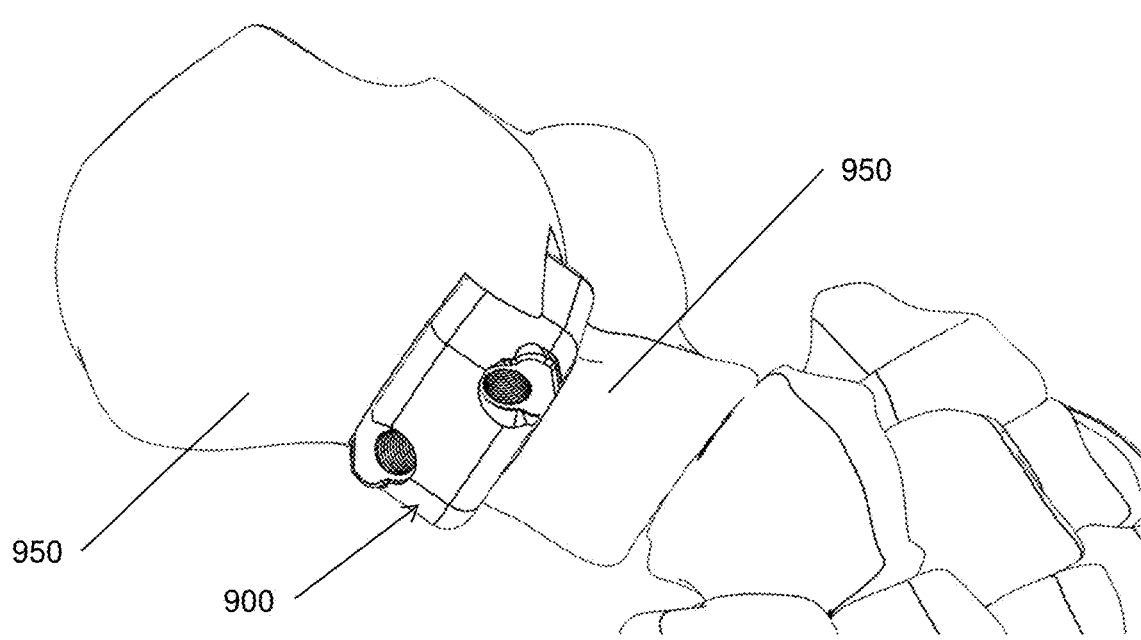
FIG. 9 is a two anchor embodiment used as an osteotomy wedge.

For instance, FIG. 9 depicts a perspective view of two anchor implant 900 joining a fractured re-aligned calcaneus 950 together (the Talus has been removed for clarity). The implant 900 and the associated anchors fixes and holds the osteotomies together. Other applications are possible. As an example, FIG. 10 is a perspective view of a top of a tibia 1050 showing a four anchor implant 1000 joining the top of the tibia together.

Distraction:

Although the above discussion focuses on compressing boney structures together or compressing a boney structure against an implant, the above anchors and methods could also be used to cause distraction between a first boney structure and a second boney structure via a modification of the anchors and implants. By reversing or flipping the head geometry (i.e. offset portions 114, 214, and 314) of the anchors 100, 200, or 300 and reversing or flipping the engagement surfaces 512, 612, and 712 and geometries of the respective apertures of implants 500, 600, and 700, distraction of boney structures can be achieved by using the methods described above.

Inserter Embodiments

Figure 11A:
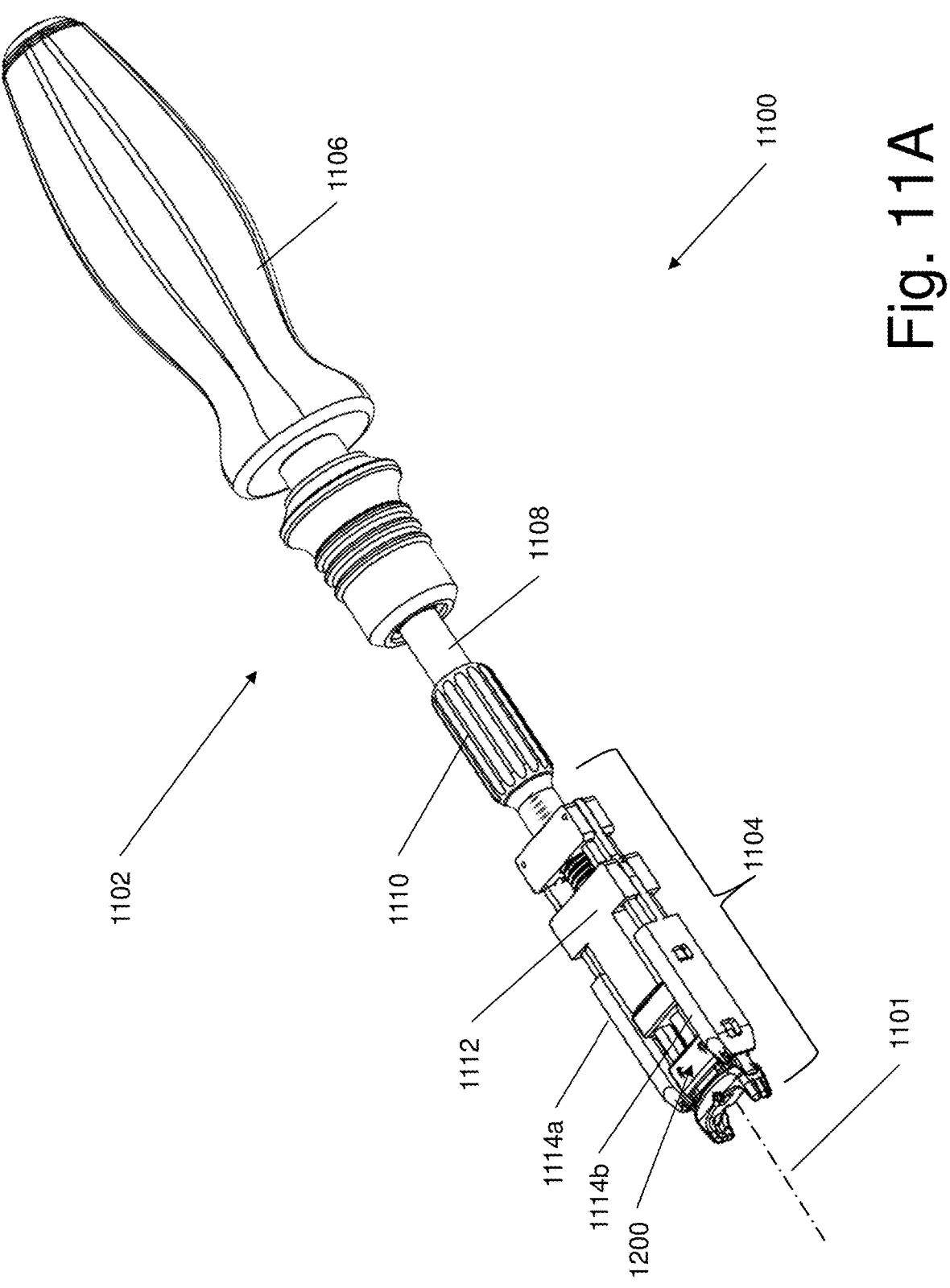
FIG. 11A is a perspective view of one aspect of an implant insertion system which can be used in one or more aspects of the present invention.
Figure 11B:
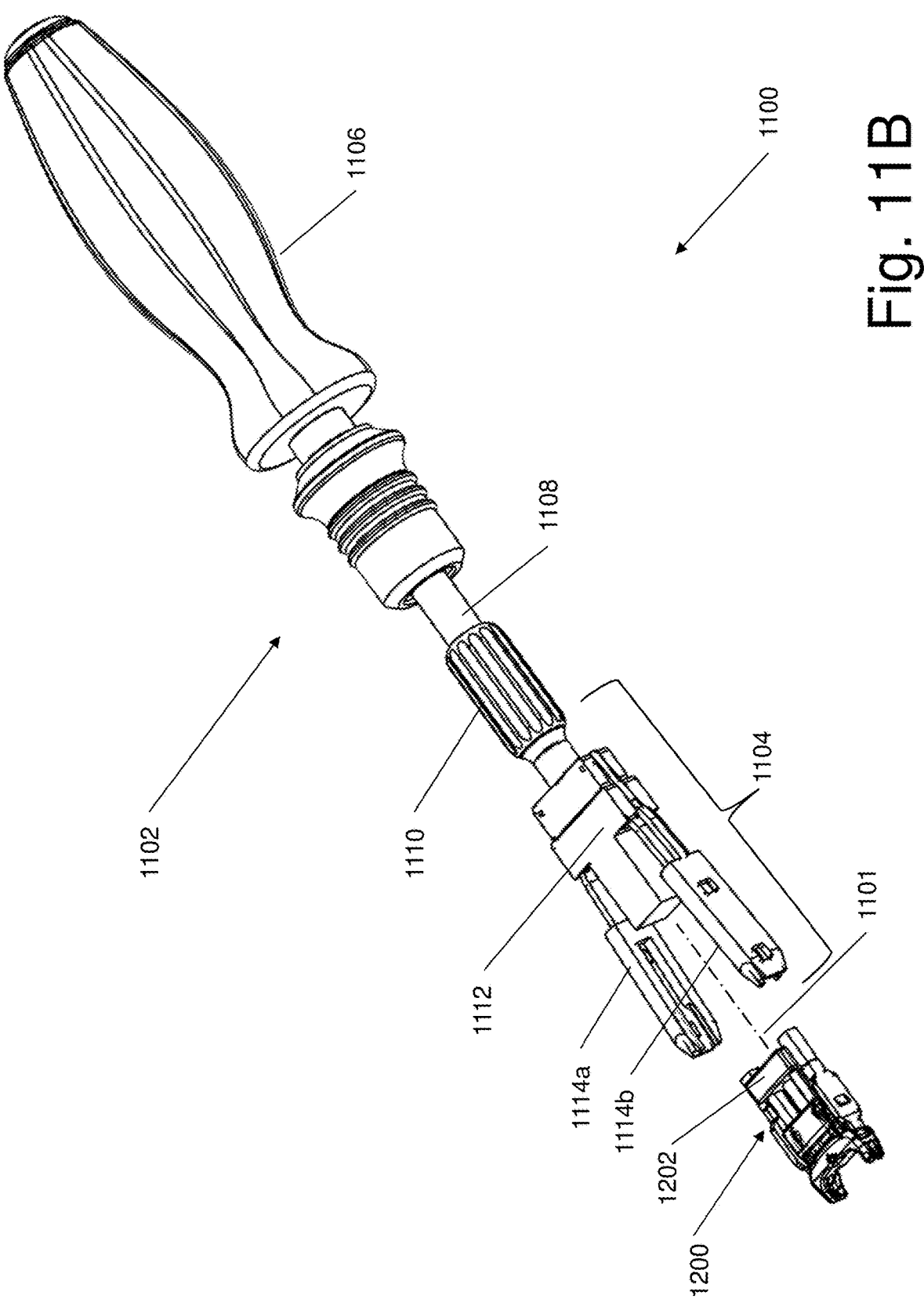
FIG. 11B is an exploded perspective view of the implant insertion system of FIG. 11A showing an implant cassette detached from the implant inserter system.

Turning now to FIG. 11A, there is presented a perspective view of an implant insertion system 1100. In certain embodiments, the implant insertion system 1100 comprises an inserter tool 1102 and an implant cassette 1200. FIG. 11B is a perspective view of the implant insertion system 1100 with the implant cassette 1200 decoupled from the inserter tool 1102.

In certain embodiments, a rotatable handle 1106 or another torque inducing mechanism is positioned at the proximal end of the inserter tool. The rotatable handle 1106 is coupled to a proximal end of a longitudinal shaft or actuating rod 1108. In certain embodiments, the actuating rod 1108 passes through a fixed or non-rotating collar 1110 and has a distal end that is rotatably coupled to an implant deployment mechanism 1104. In certain embodiments, the rotatable handle 1106 is designed to impart a torque on the actuating rod 1108 when a user turns the rotatable handle 1106. The fixed collar or non-rotating collar 1110 allows the user to provide stability and counter-torque when the rotatable handle 1106 is turned during insertion and deployment of the anchors. The use of the term "fixed collar" or "non-rotating" collar in this disclosure means that the user will hold the collar stationary with respect to the turning motion imparted on the handle 1106. The actuating rod 1108, the rotatable handle 1106, the fixed collar 1110 may be positioned concentrically along a longitudinal axis 1101 of the inserter tool 1102.

In certain embodiments, the implant deployment mechanism 1104 comprises a translating element 1112 which may be used to impart a linear force on a force transmission sub-assembly 1202 of the implant cassette 1200 when a torque is introduced on the actuating rod 1108. In certain embodiments, the implant deployment mechanism 1104 is releasably coupled to the implant cassette 1200 via side arms 1114*a* and 1114*b* which retain the implant cassette 1200 during deployment of the anchors.

Figure 11C:
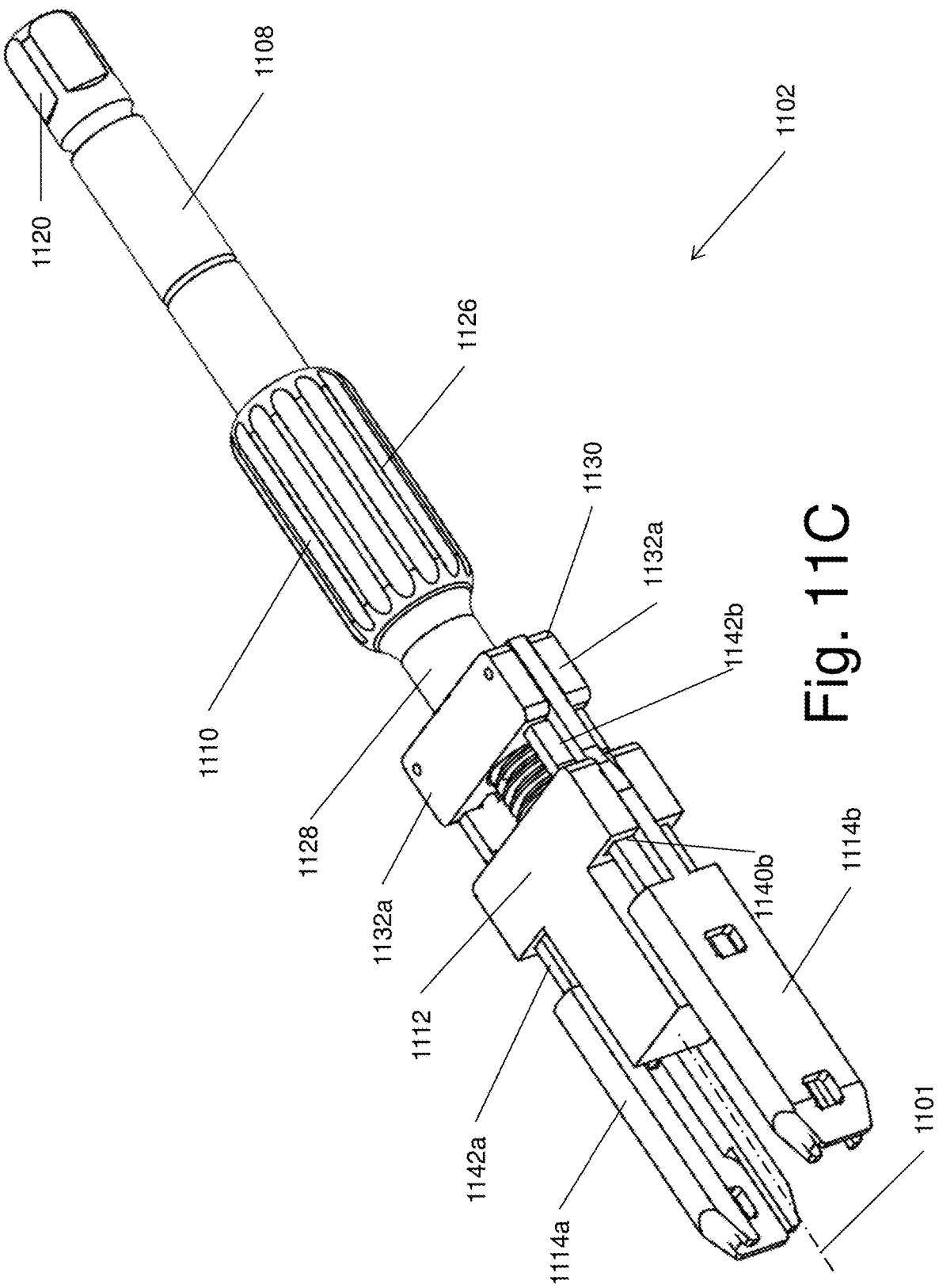
FIG. 11C is a detailed perspective view of an inserter tool with the handle removed for clarity.
Figure 11D:
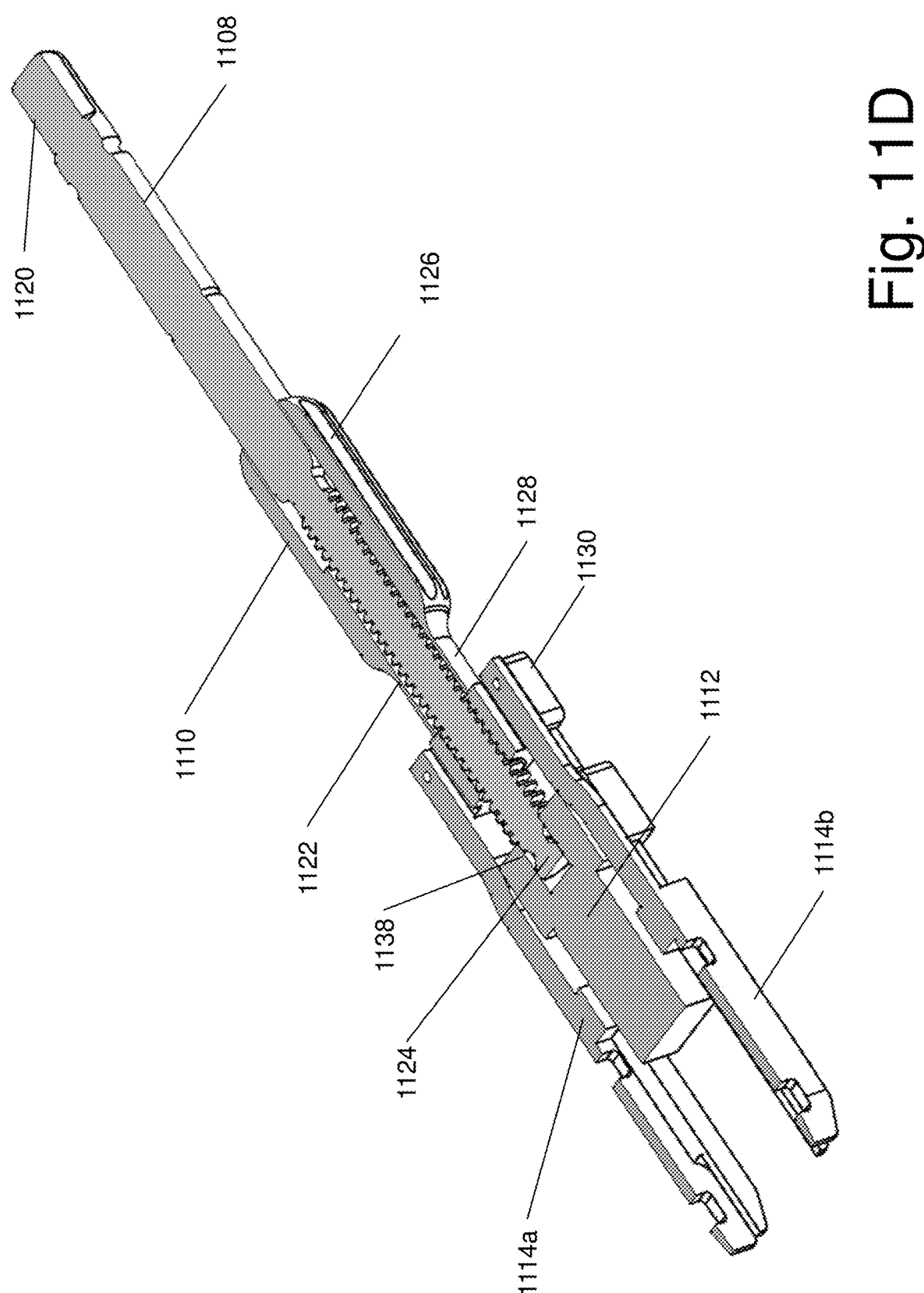
FIG. 11D is a horizontal sectional perspective view of the inserter tool of FIG. 11C.
Figure 11E:
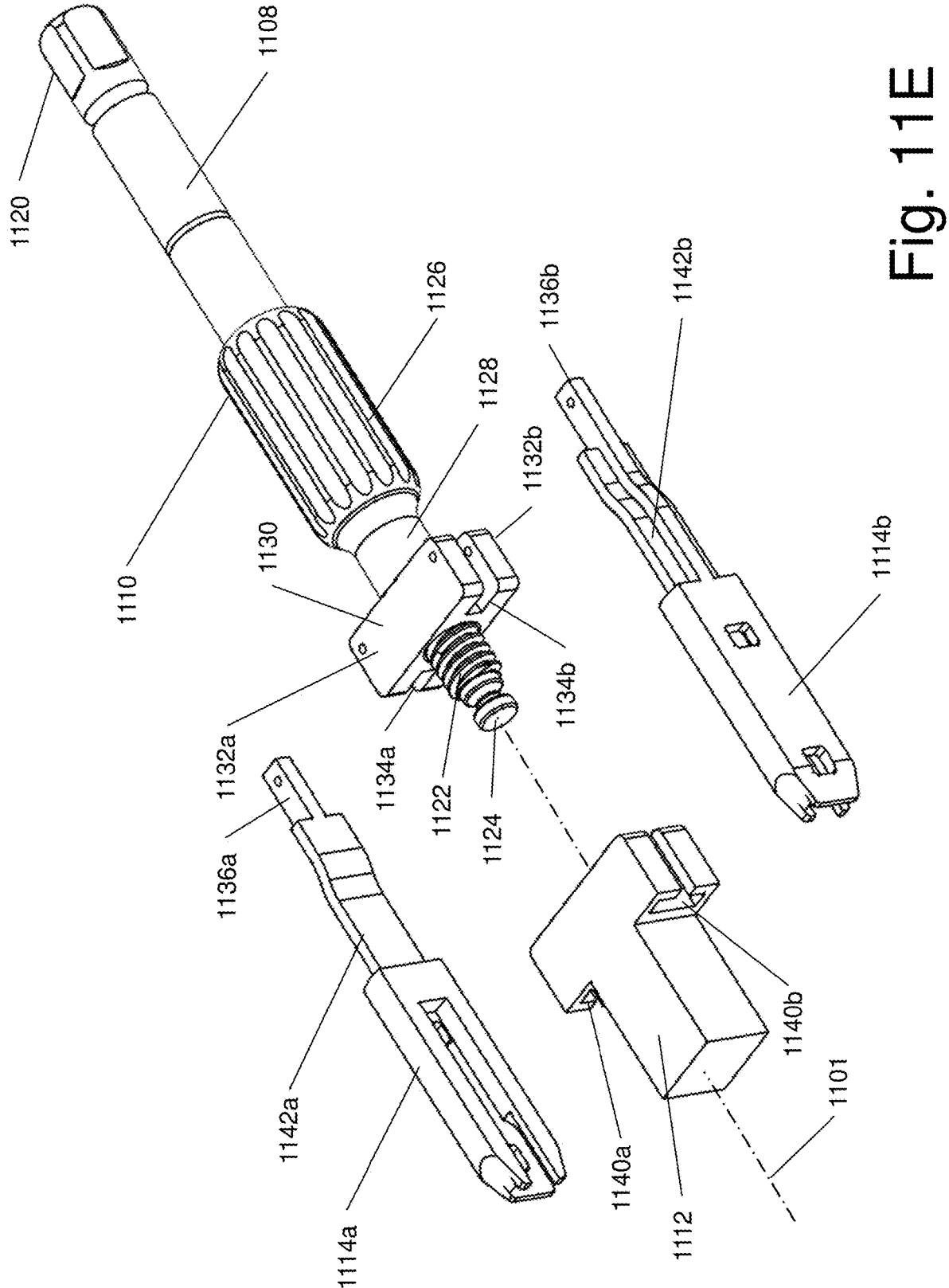
FIG. 11E is an exploded perspective view of the inserter tool of FIG. 11C.

FIG. 11C is a perspective view of the implant insertion tool 1102 with the handle 1106 removed for clarity. FIG. 11D is horizontal section cut of the components illustrated in FIG. 11C. FIG. 11E is an exploded view of the components illustrated in FIG. 11C.

In certain embodiments, a proximal end 1120 of the actuating rod 1108 may have a rectangular, hexagonal, or other shape designed to transmit torque from the handle 1106 (not shown) to the actuating rod 1108 without slipping. Such as shape may be especially advantageous in embodiments where the handle 1106 is removable from the actuating rod 1108. In certain embodiments, the actuating rod 1108 may have an outer threaded surface 1122 defined over a substantial portion of its distal longitudinal length as indicated in FIG. 11D. The distal end 1124 of the actuating rod may have a pin or ball connection to allow the distal end 1124 to rotate without imparting a significant torsional force onto the translating element 1112.

In the illustrative embodiment, the fixed collar 1110 comprises a gripping collar 1126, a connecting collar 1128, and a translation block 1130. In certain embodiments, the translation block 1130 has an interior through bore which has a threaded interior surface sized to rotationally mate with the outer threaded surface 1122 of the actuating rod 1108 (See FIG. 11D). In certain embodiments, the translation block 1130 has two opposing side elements 1132a and 1132b. Each side element 1132a and 1132b has a corresponding horizontal slot 1134a and 1134b sized to accommodate proximal ends 1136a and 1136b of the side arms 1114a and 1114b, respectively. In certain embodiments, a pin (not shown) may be used to couple the ends 1136a-1136b to the opposing side elements 1132a and 1132b such that the side arms 1114a and 1114b can swing out in a transverse manner with respect to the longitudinal axis 1101.

The translating element 1112 has a proximal opening 1138 (visible in FIG. 11D) sized to accommodate and house the distal end 1124 of the actuating rod 1108. In certain embodiments the translating element 1112 has side channels 1140a and 1140b (See FIG. 11E) which are sized to loosely slide along rails 1142a and 1142b of the side arms 1114a and 1114b, respectively.

Referring back to FIG. 11A, when a user turns the handle 1106, a torque is applied to the actuating rod 1108. The user also holds the fixed collar 1110 stationary. Because the outer threaded surface 1122 of the actuating rod 1108 is mated with the inner threaded bore of the translation block 1130 (See FIG. 11E), the actuating rod 1108 moves linearly along the axis 1101 as torque is applied to its proximal end. The linear movement of the distal end 1124 actuating rod 1108 causes the translating element 1112 to also move along the linear axis 1101. The translating element 1112 is rotatably coupled to the distal end 1124 such that the distal end 1124 can impart a linear movement to the translating element. The translating element 1112 is also loosely guided by the interaction of its channels 1140a and 1140b and the rails 1142a and 1142b of the side arms 1114a and 1114b, respectively. The side arms 1114a and 1114b also keep the translating element 1112 from rotating about the longitudinal axis 1101. Consequently, the translating element 1112 retains its radial position with respect to the longitudinal axis 1101 as it is pushed or pulled along the longitudinal axis by the distal end 1124 of the actuating rod.

Figure 12A:
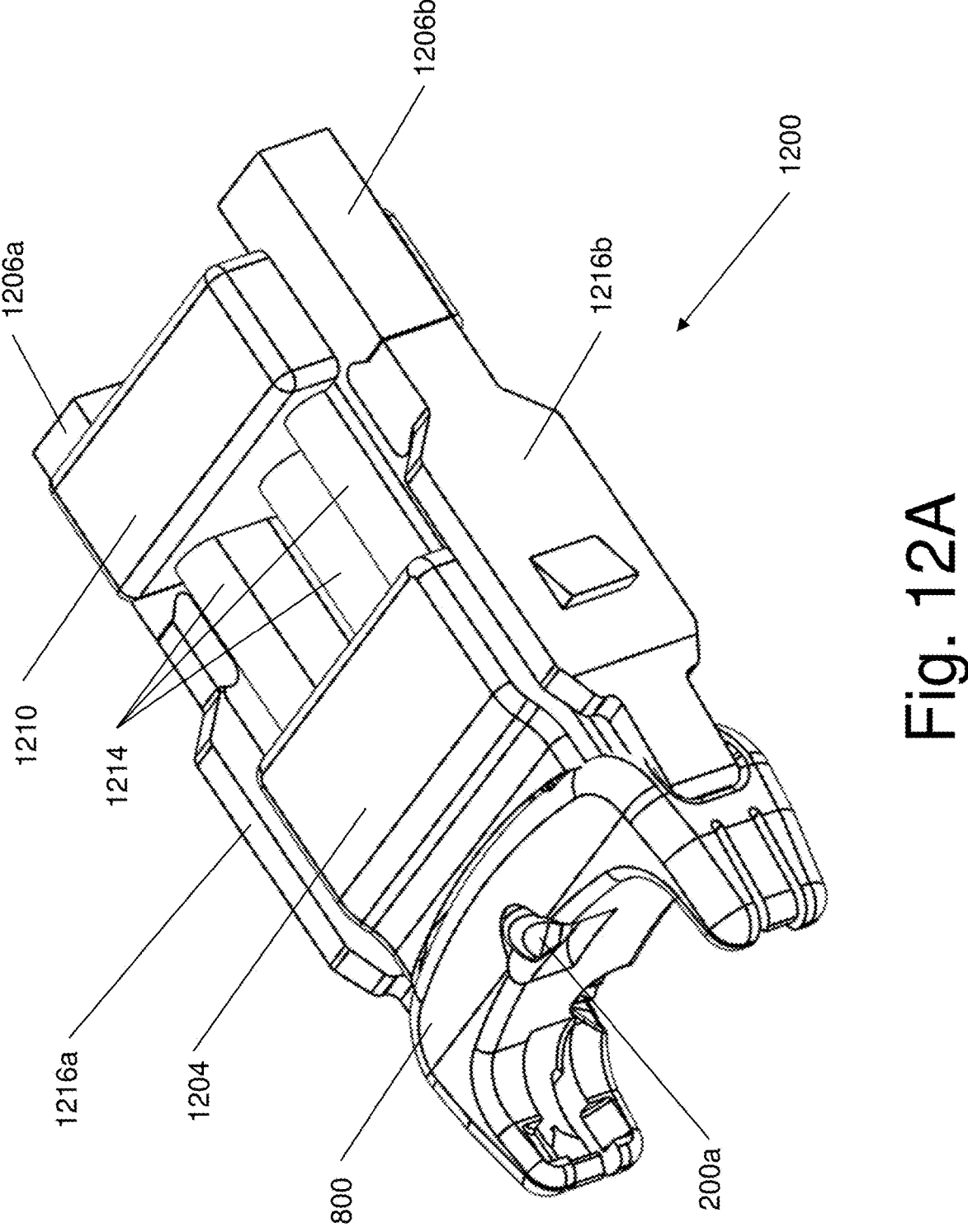
FIG. 12A is a perspective view of an implant cassette which may be used with one or more aspects of the present invention.
Figure 12B:
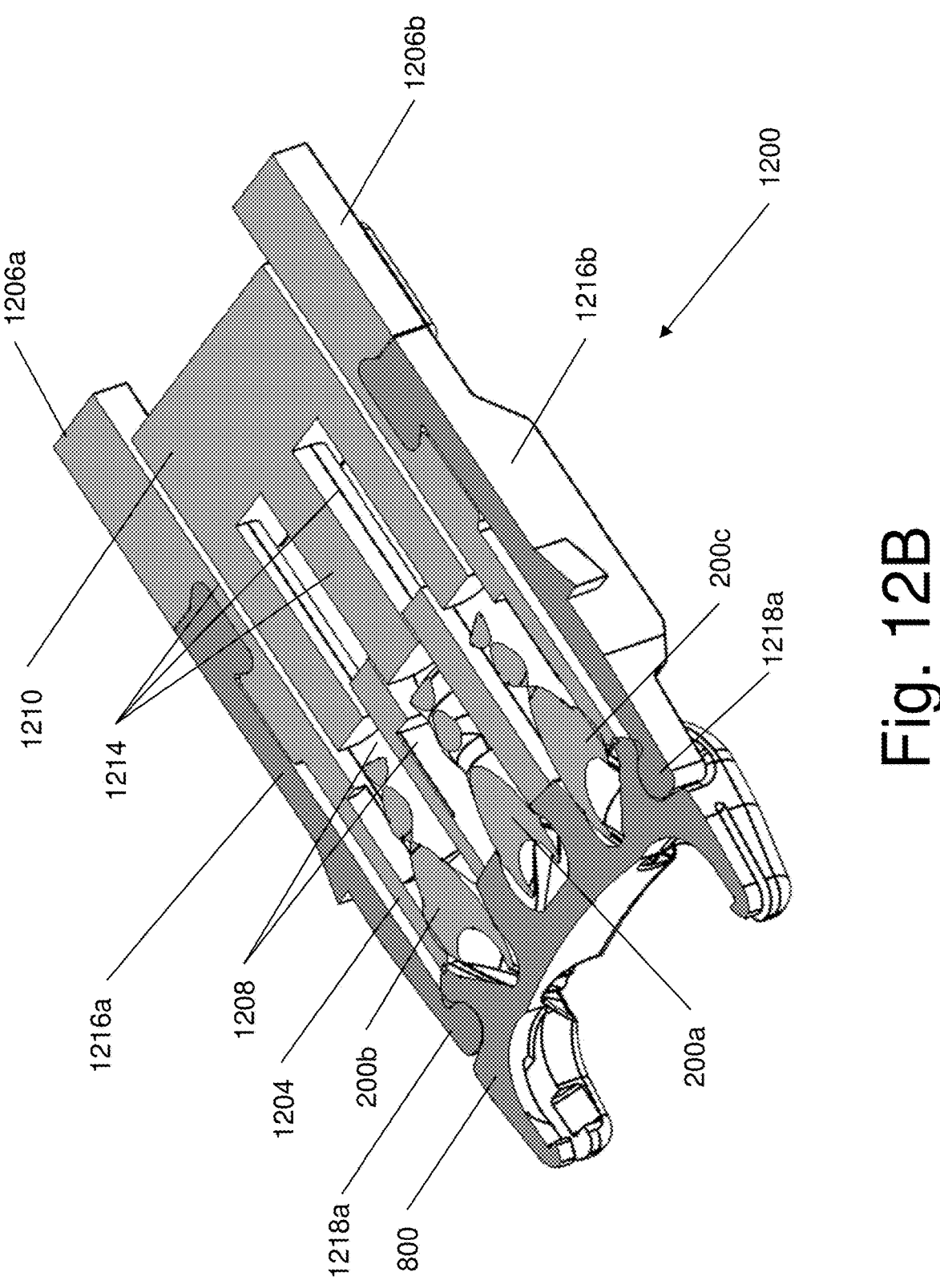
FIG. 12B is a horizontal sectional perspective view of the implant cassette of FIG. 12A.

FIG. 12A is a perspective view of one embodiment of an implant cassette 1200 in a pre-loaded condition which can be used with the implant inserter tool 1102. FIG. 12B is horizontal section cut of the implant cassette 1200 and FIG. 12C is an exploded view of the implant cassette.

Figure 12C:
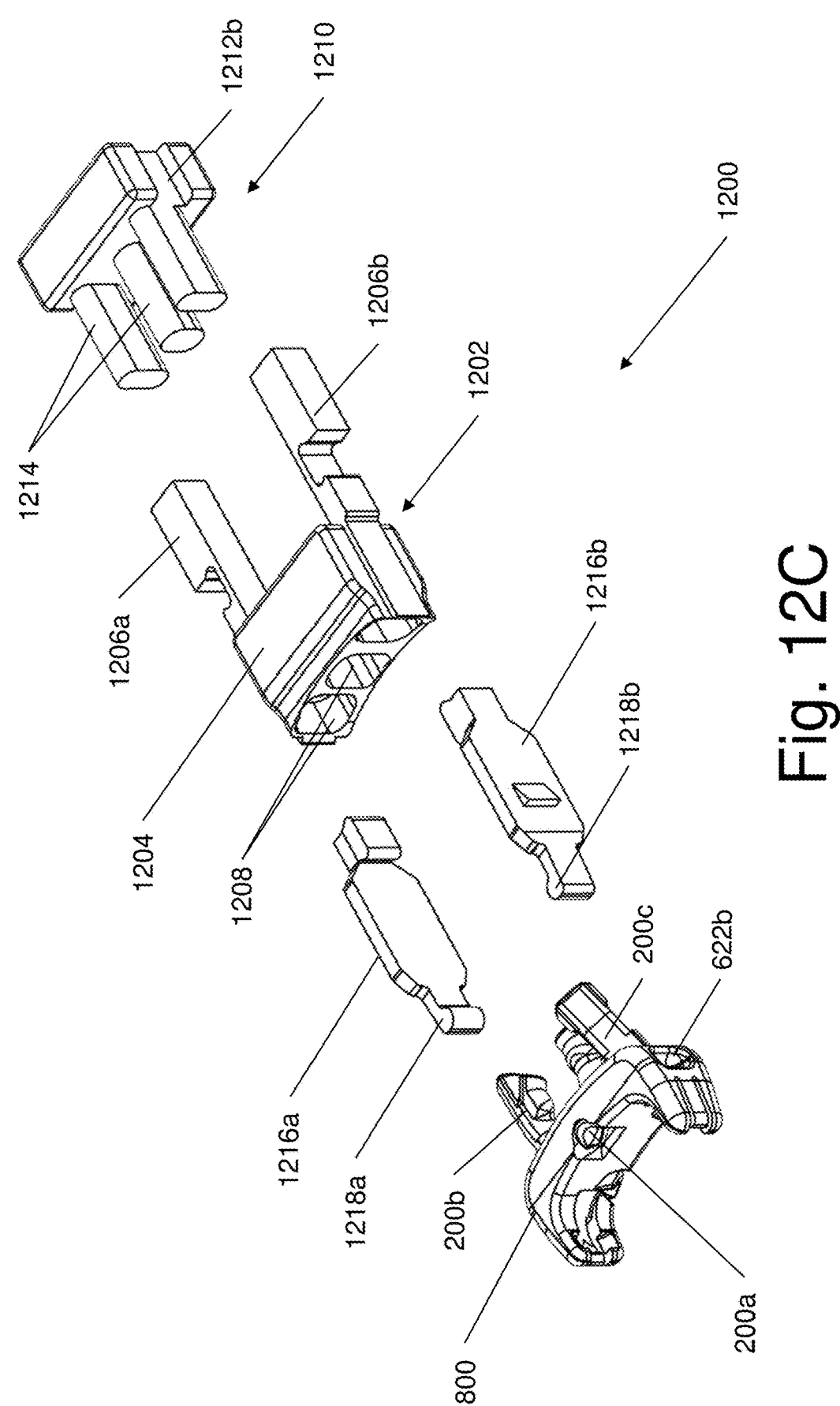
FIG. 12C is an exploded perspective view of the implant cassette of FIG. 12A.

Turning now to FIGS. 12A to 12C, there is a mounting unit 1202 comprising a main body 1204 and guide arms 1206a and 1206b extending on each side of the main body 1204 in a longitudinal direction towards a proximal end of the cassette 1200. The main body 1204 defines a plurality of deployment channels 1208 where each deployment channel corresponds to the number of anchors in the implant. In the illustrative embodiment, there are three deployment channels 1208 corresponding to three anchors 200a, 200b, and 200c of the implant 800 as discussed in reference to FIG. 8A above. As best illustrated by FIG. 12B, when the implant cassette 1200 is in a pre-deployed configuration, the anchors 200a-200c are partially positioned within the implant 800 and partially positioned within the plurality of deployment channels 1208 where each anchor 200a-200c is at least partially within its own corresponding deployment channel. In other embodiments, the anchors 200a-200c are entirely positioned within their respective deployment channels.

A force transmission unit 1210 is positioned on the proximal side of the main body 1204 and primarily fits between the guide arms 1206a-1206b of the mounting unit 1202. Each side of the force transmission unit 1210 defines a channel 1212a-1212b (only channel 1212b is visible in FIG. 12C) sized to interact with the guide arms 1206a-1206b such that the force transmission unit 1210 can slide along the guide arms in the longitudinal direction. The proximal face of the force transmission unit 1210 is designed to interact with and receive a longitudinal linear force from the translation element 1112 of the implant inserter tool 1102 (see FIGS. 11A and 11B). A plurality of push rods 1214 projects from a distal face of the force transmission unit 1210. The number and location of push rods 1214 corresponds to the number and location of the plurality of deployment channels 1208 defined within the main body 1204 of the mounting unit 1202. The push rods 1214 are sized and shaped to be received by the plurality of deployment channels 1208 of the mounting unit 1202.

In certain embodiments, proximal ends of retention arms 1216a-1216b are sized and shaped to couple with the guide arms 1206a and 1206b of the mounting unit 1202. Ribs 1218a and 1218b formed on the distal ends of the retention arms 1216a-1216b are sized to releasably couple with side apertures 622a-622b (note only side aperture 622b is visible in FIG. 12C) of the implant 800.

Figure 12D:
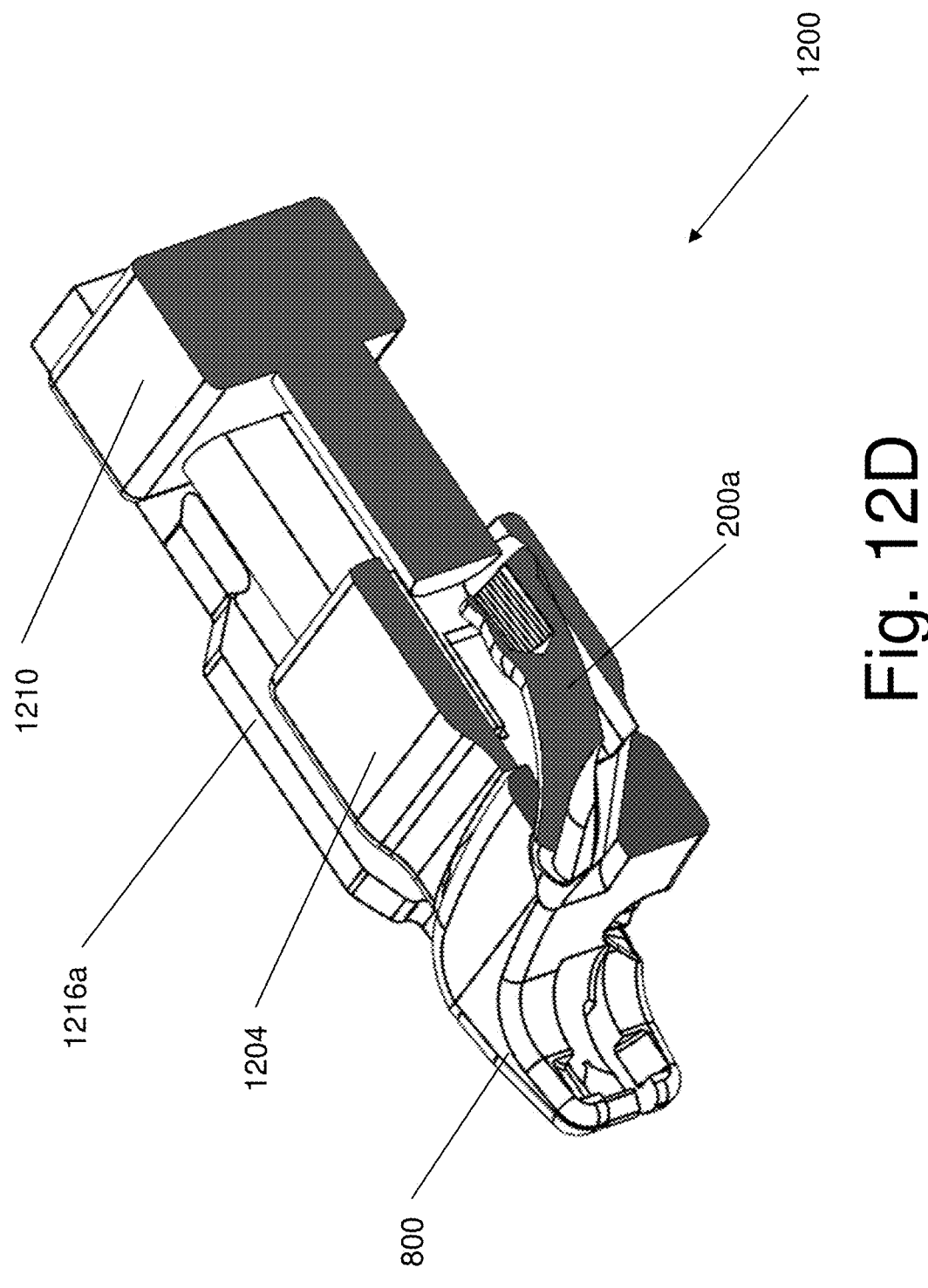
FIG. 12D is a vertical sectional perspective view of the implant cassette of FIG. 12A showing an anchor in a pre-deployed position.
Figure 12E:
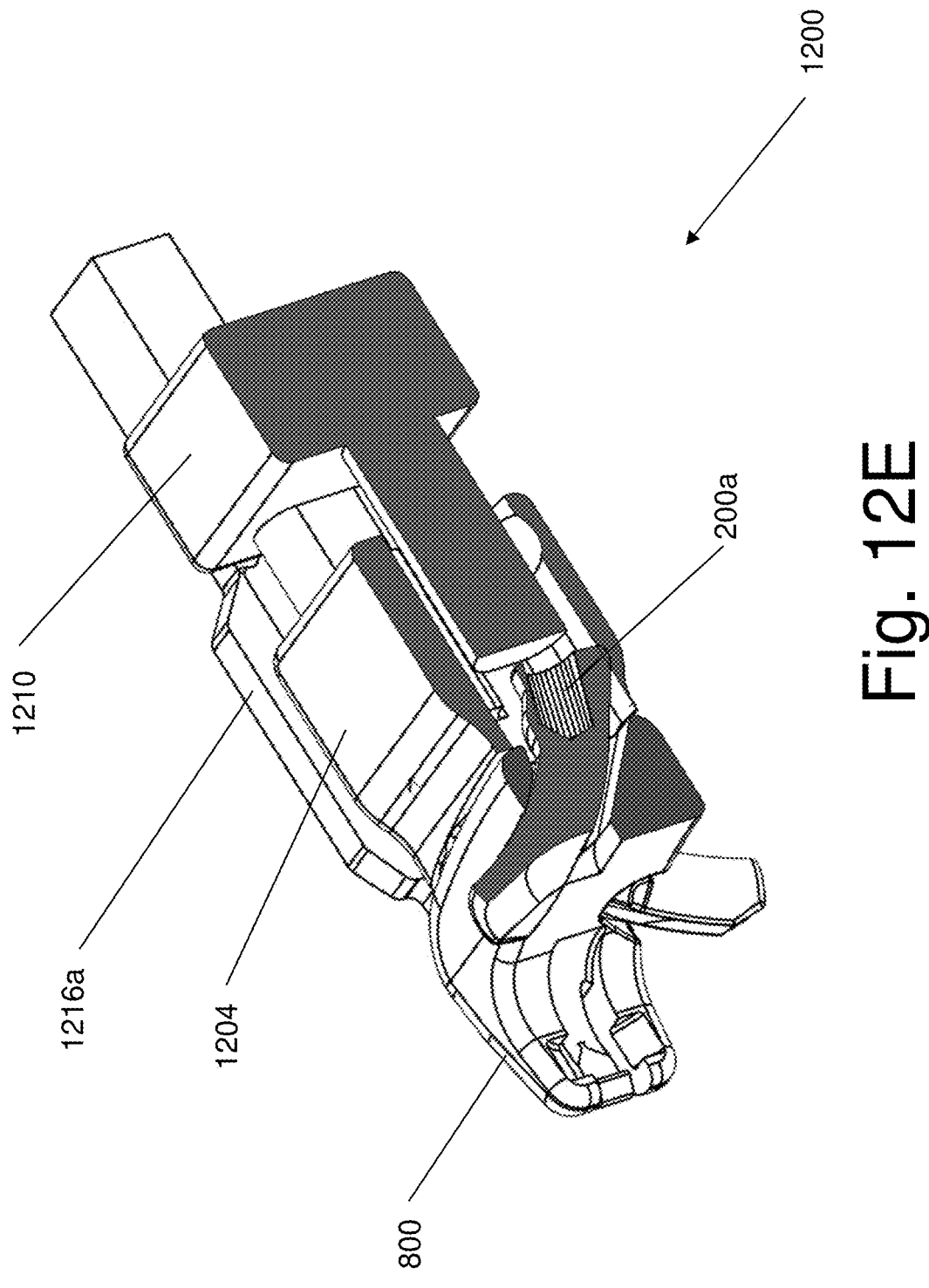
FIG. 12E is a vertical sectional perspective view of the implant cassette of FIG. 12A showing an anchor in a mid-deployed position.
Figure 12F:
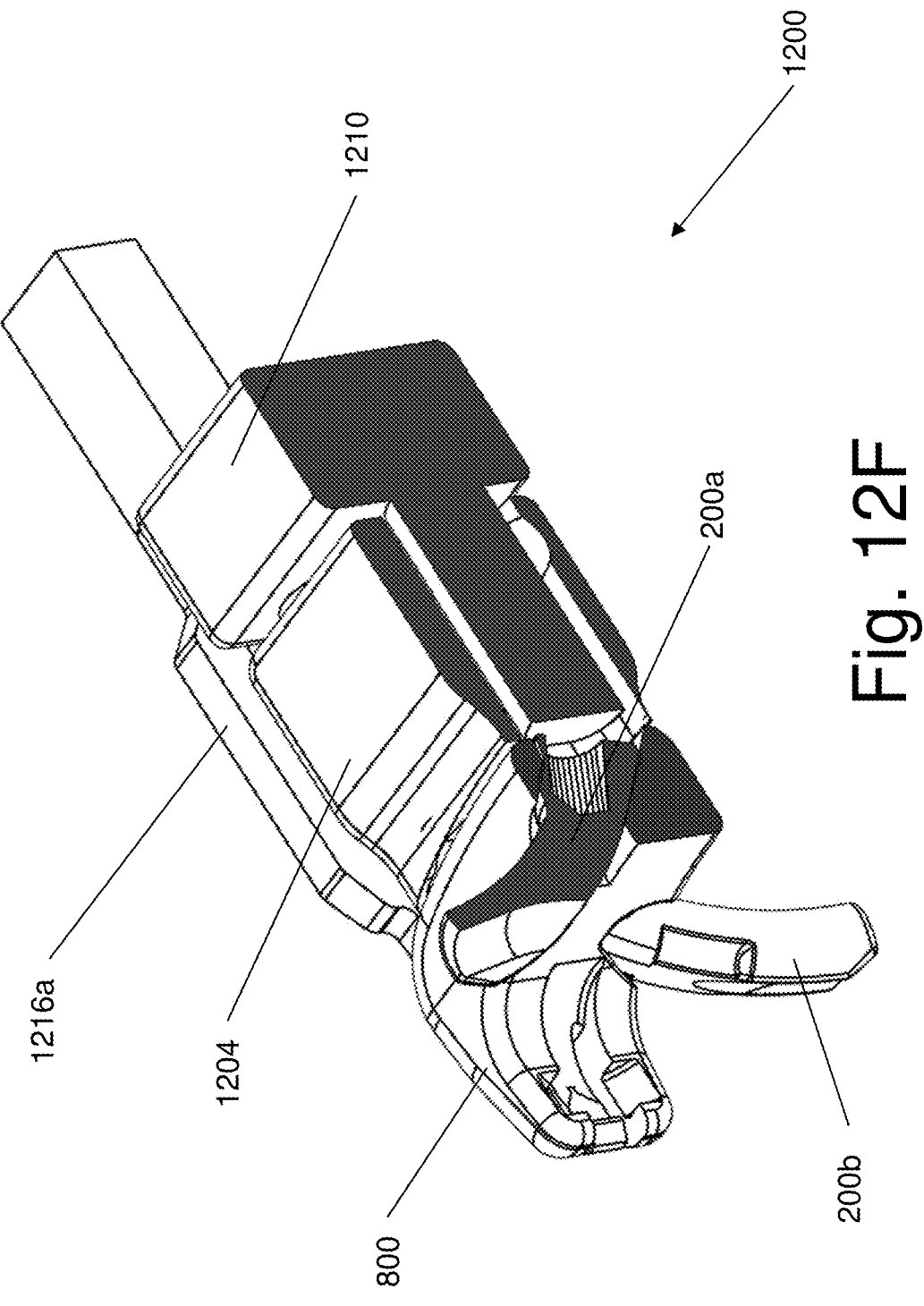
FIG. 12F is a vertical sectional perspective view of the implant cassette of FIG. 12A showing an anchor in a fully deployed position.

Referring now to FIGS. 11A and 11B and more specifically to FIGS. 12D through 12F, a manner of using one embodiment of the implant insertion system 1100 will now be described. FIG. 12D is a vertical sectional perspective view of the implant cassette 1200 in a pre-deployed or first configuration. FIG. 12E is a vertical sectional perspective view of the implant cassette 1200 in a mid-deployed or second configuration. FIG. 12F is a vertical sectional perspective view of the implant cassette 1200 in a fully deployed or third configuration.

In certain embodiments, a user can use the system 1100 to position the implant 800 into a surgical site as illustrated in FIG. 8C, above. As discussed previously, in FIG. 8C, the implant 800 has been positioned adjacent to a first boney structure 850a and a second boney structure 850b. As discussed above, the three anchors 200a, 200b, and 200c have been positioned inside the implant cassette 1200 and they are partially positioned (or introduced) inside the implant 800 and partially positioned inside the deployment channels 1208 of the mounting unit 1202 as indicated in FIG. 12D (in FIG. 12D, only implant 200a is visible).

The user can then apply a rotating force to the handle 1106 while holding the fixed collar 1110 stationary (see FIGS. 11A through 11E, above). The rotation of the handle 1106 causes a torque to be applied to the actuating rod 1108. In response, the actuating rod 1108 advances in a linear fashion with respect to the fixed collar 1110 due to the interaction of the threaded exterior surface 1122 of the actuating rod and the threaded interior surface of the fixed collar as described above. As the actuating rod 1108 advances along the longitudinal axis 1101, the translating element 1112 is pushed towards the distal end of the inserting tool 1102. This results in a smooth non-rotating force applied to the proximal end of the force transmission unit 1210.

In response to the linear force being applied to the proximal end of the force transmission unit 1210, the transmission unit 1210 begins to move which causes the push rods 1214 to apply a smooth non-rotating force to the proximal ends of the anchors 200*a*, 200*b*, and 200*c* which are positioned in the respective deployment channels 1208 of the mounting unit 1202.

The force on the proximal ends of the anchors causes the anchors to move along an initial trajectory into the boney structures 850*a* and 850*b* as illustrated in FIG. 12E and as discussed above. As the user continues to turn the handle 1106, the smooth non-rotating force continues to be applied to the proximal ends of the anchors 200*a*, 200*b*, and 200*c* which causes the anchors to move along their initial trajectory. As the offset heads of the anchors reach their respective apertures defined in the implant 800, the offset heads interact with the apertures which cause a transverse shift of the anchor and the attached boney structures 850*a* and 850*b*. This transverse shift will cause the boney structures 850*a* and 850*b* to compress against the implant 800 as discussed above until the anchors are fully deployed into the boney structures 850*a* and 850*b* as indicated by FIG. 12F and FIG. 8D (above).

Once the anchors are fully deployed, the turnable handle 1106 may be rotated in a direction opposite to the insertion rotation direction with respect to the fixed collar 1110 (e.g., counter-clockwise). This opposite rotation will cause the translation element 1112 to move longitudinally backwards towards a proximal end of the implant insertion tool 1102. As the translation element 1112 moves towards the translation block 1130, the side arms 1114*a* and 1114*b* of the implant inserter tool will rotate outwards in a direction transverse to the longitudinal axis 1101 as indicated in FIG. 11B.

Because the retention arms 1216*a* and 1216*b* of the implant cassette 1200 are slidingly coupled to the side arms 1114*a* and 1114*b* of the inserter tool 1102, the retention arms 1216*a* and 1216*b* will also rotate away from the implant 800 which will cause the retention arms 1216*a* and 1216*b* to release the deployed implant 800. Once the implant 800 has been released from the retention arms 1216*a* and 1216*b*, the inserter tool 1102 may be then be removed from the surgical site. The surgical site can then be closed in a traditional manner.

The various components of certain embodiments of the inserter systems described herein may be produced from readily available materials suitable for short term tissue contact in surgery. Such materials include stainless steel alloys, titanium and its alloys, and rigid polymers including fiber reinforced polymers.

Alternative Inserter Embodiments

Figure 13A:
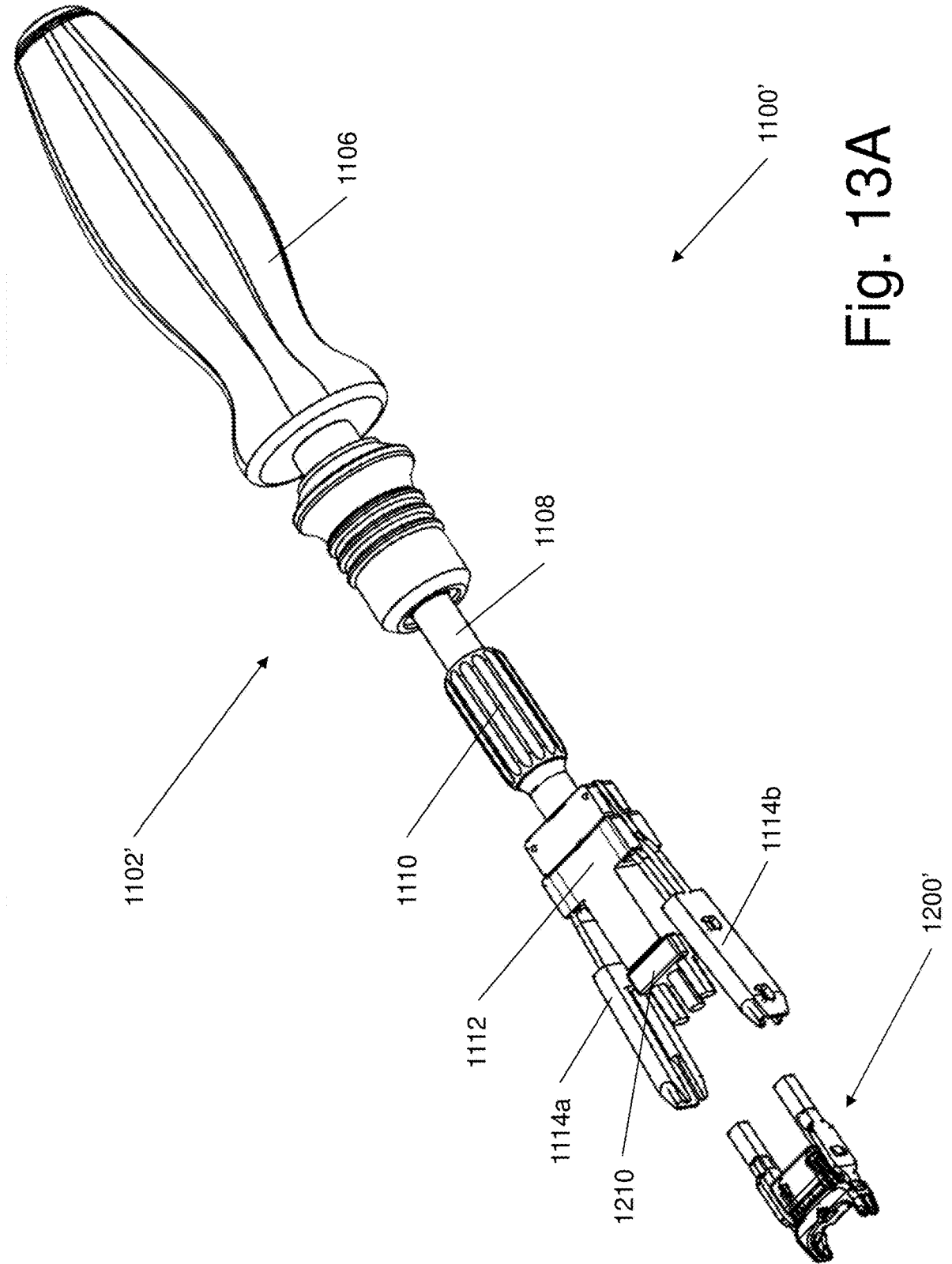
FIG. 13A is an exploded perspective view of an alternative implant insertion system.
Figure 13B:
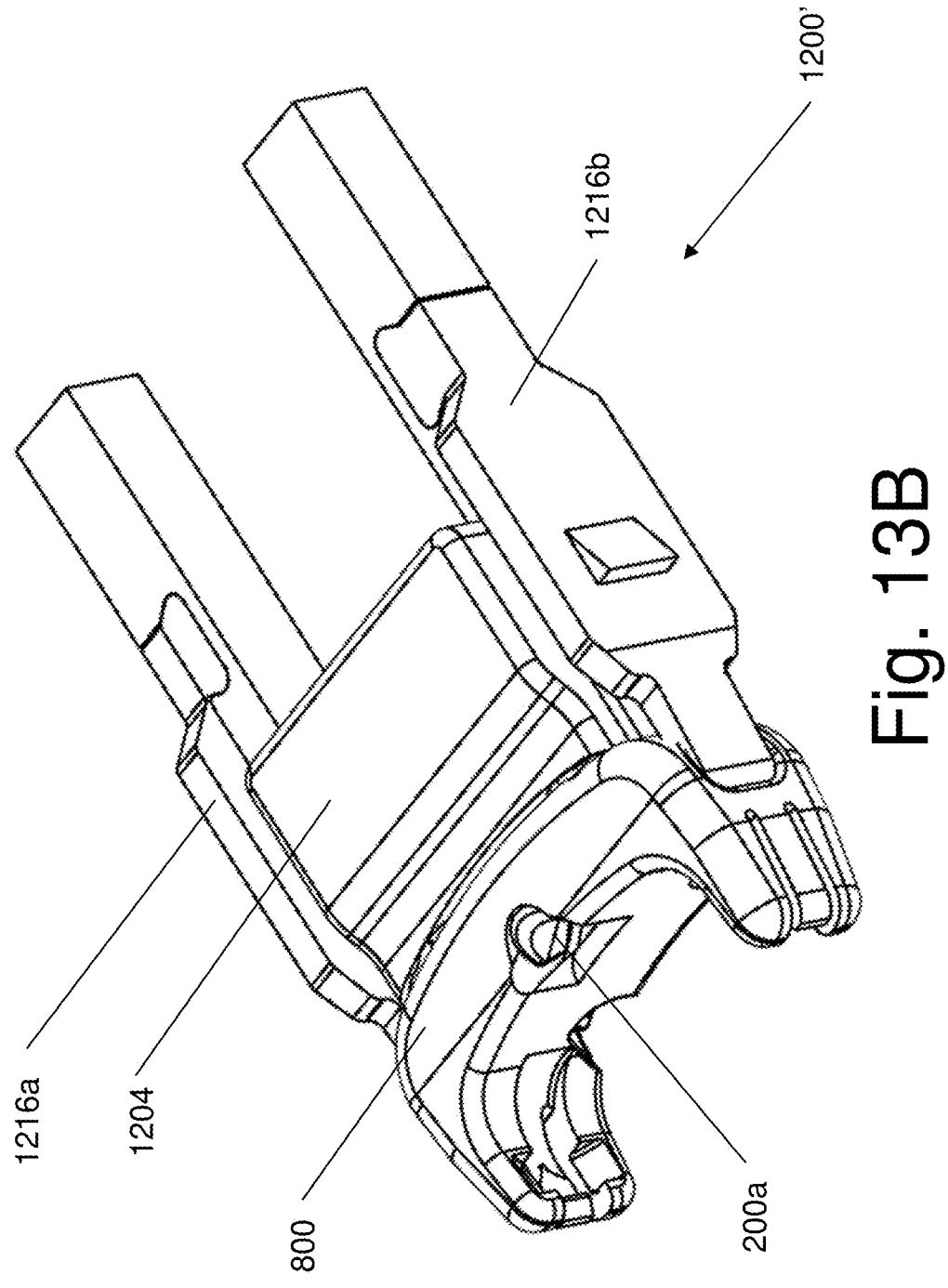
FIG. 13B is a perspective view of an alternative implant cassette which may be used with alternative embodiment illustrated in FIG. 13A.

FIG. 13A is an exploded perspective view of an alternative implant insertion system 1100′. FIG. 13B is a perspective view of an alternative implant cassette 1200′ which can be used with the implant insertion system 1100′ of FIG. 13A. The implant insertion system 1100′ is similar to the implant insertion system 1100 except that the force transmission sub-assembly 1202 is coupled to the translating element 1112 and, consequently, is not part of the implant cassette 1200. For brevity and clarity, a description of those components which are identical or similar to those described in connection with the implant insertion system 1100 in FIGS. 11A and 11B will not be repeated here. Reference should be made to the discussion of the implant insertion system 1100 to arrive at a complete understanding of the implant insertion system 1100′.

In certain embodiments, the implant cassettes 1200 and 1200′ are designed for a single use packed in a sterile container. In this manner, the surgical staff will not need to manipulate the plate or anchors. All that is required is coupling the cassette 1200 or 1200′ to the implant insertion tool 1102 or 1102′, implanting the implant, and then deploying the anchors. In such a situation, minimizing the sterile packaging may be desirable, in which case, the implant cassette 1200′ may have advantages over the implant cassette 1200. Furthermore, because the components of the implant cassettes 1200 and 1200′ are designed to be discarded after use (except for the implant and anchors), minimizing the components (as in the embodiment of implant cassette 1200′) may have economic benefits for the distributing company.

Figure 14A:
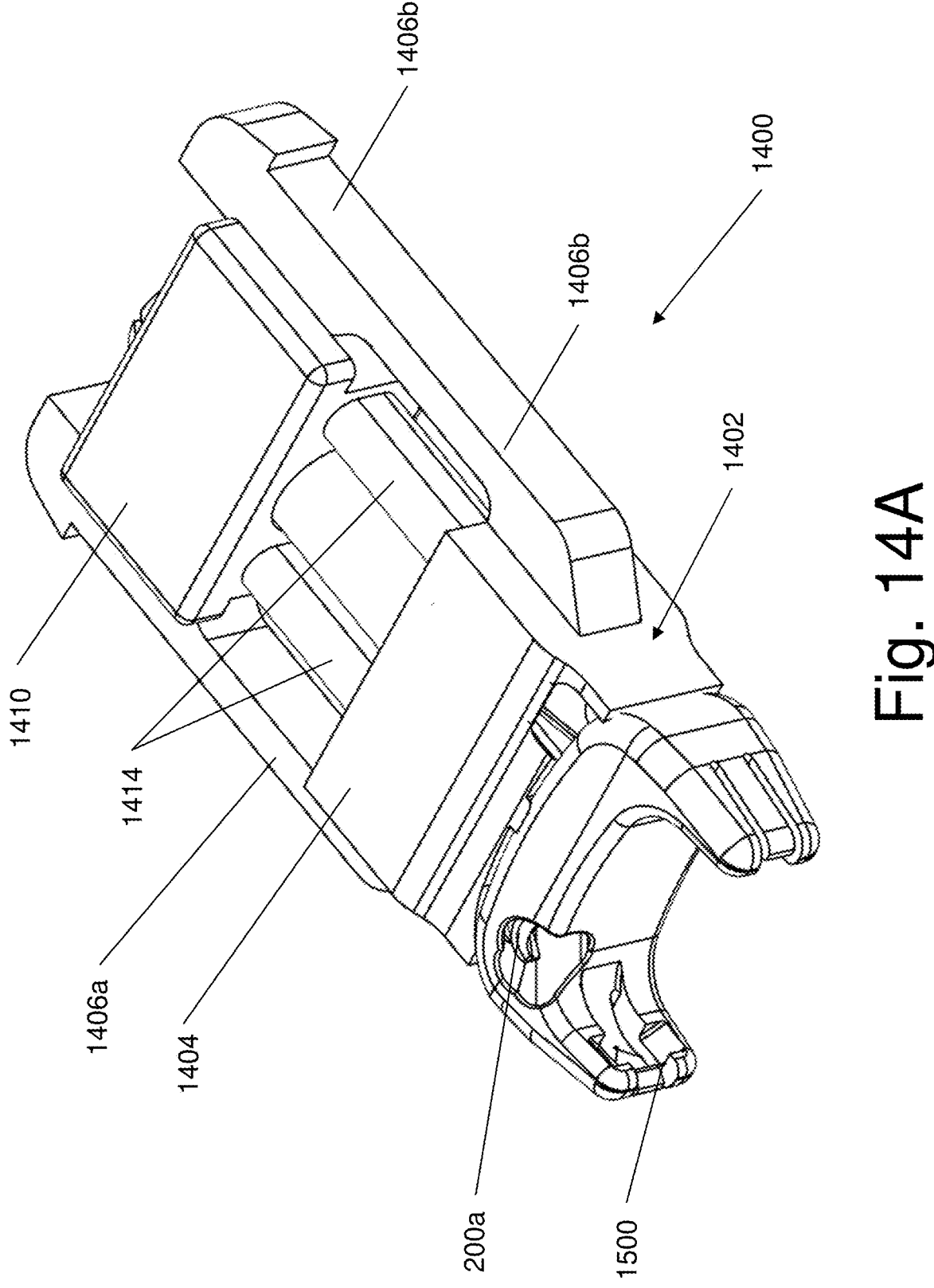
FIG. 14A is a perspective view of an alternative implant cassette which may be used with one or more aspects of the present invention.
Figure 14B:
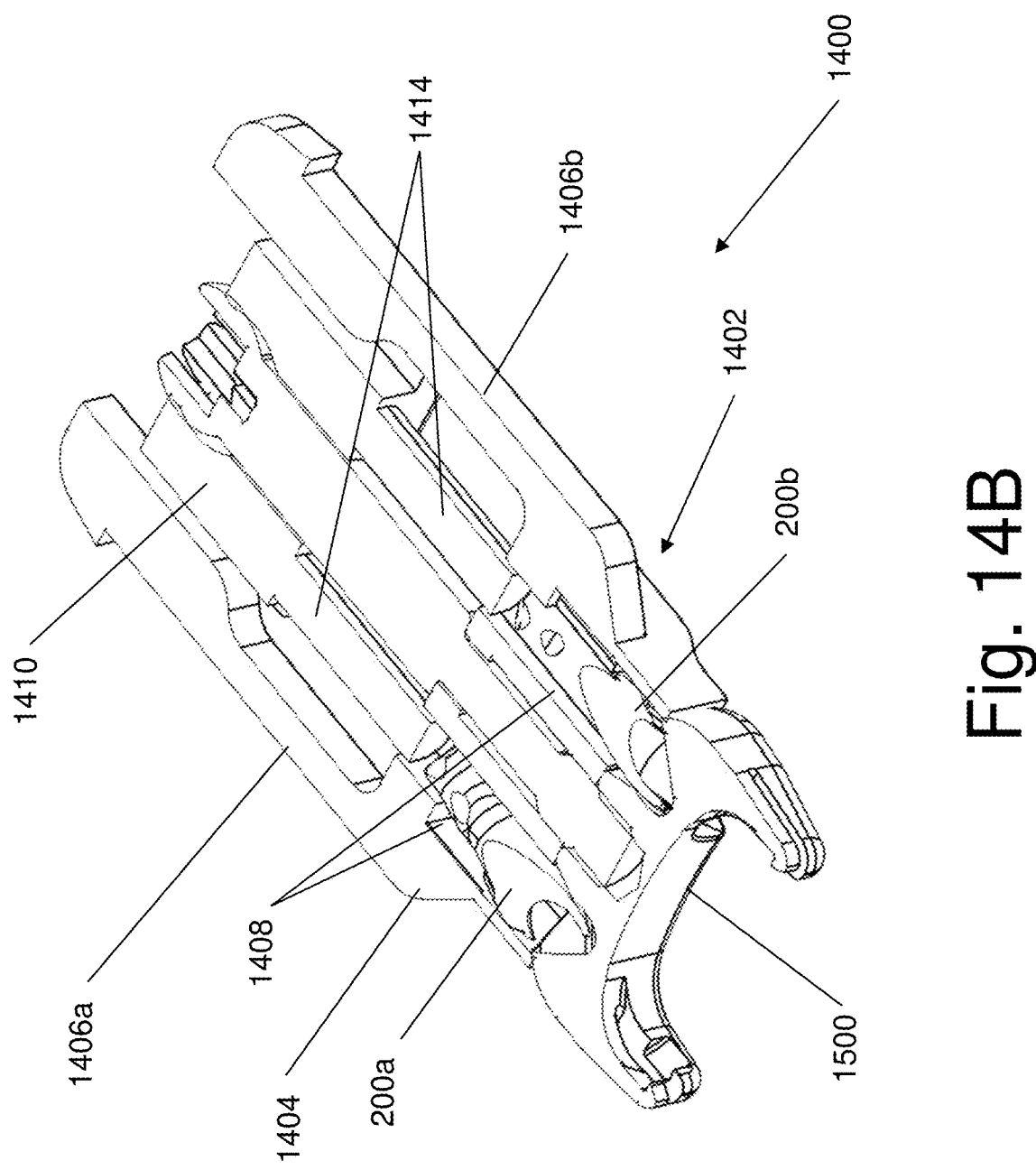
FIG. 14B is a horizontal sectional perspective view of the implant cassette of FIG. 14A.

FIG. 14A is a perspective view of another alternative embodiment of an implant cassette 1400 in a pre-loaded condition which can be used with the implant inserter tool 1102 described above. FIG. 14B is horizontal section cut of the implant cassette 1400 and FIG. 14C is an exploded view of the implant cassette.

Figure 14C:
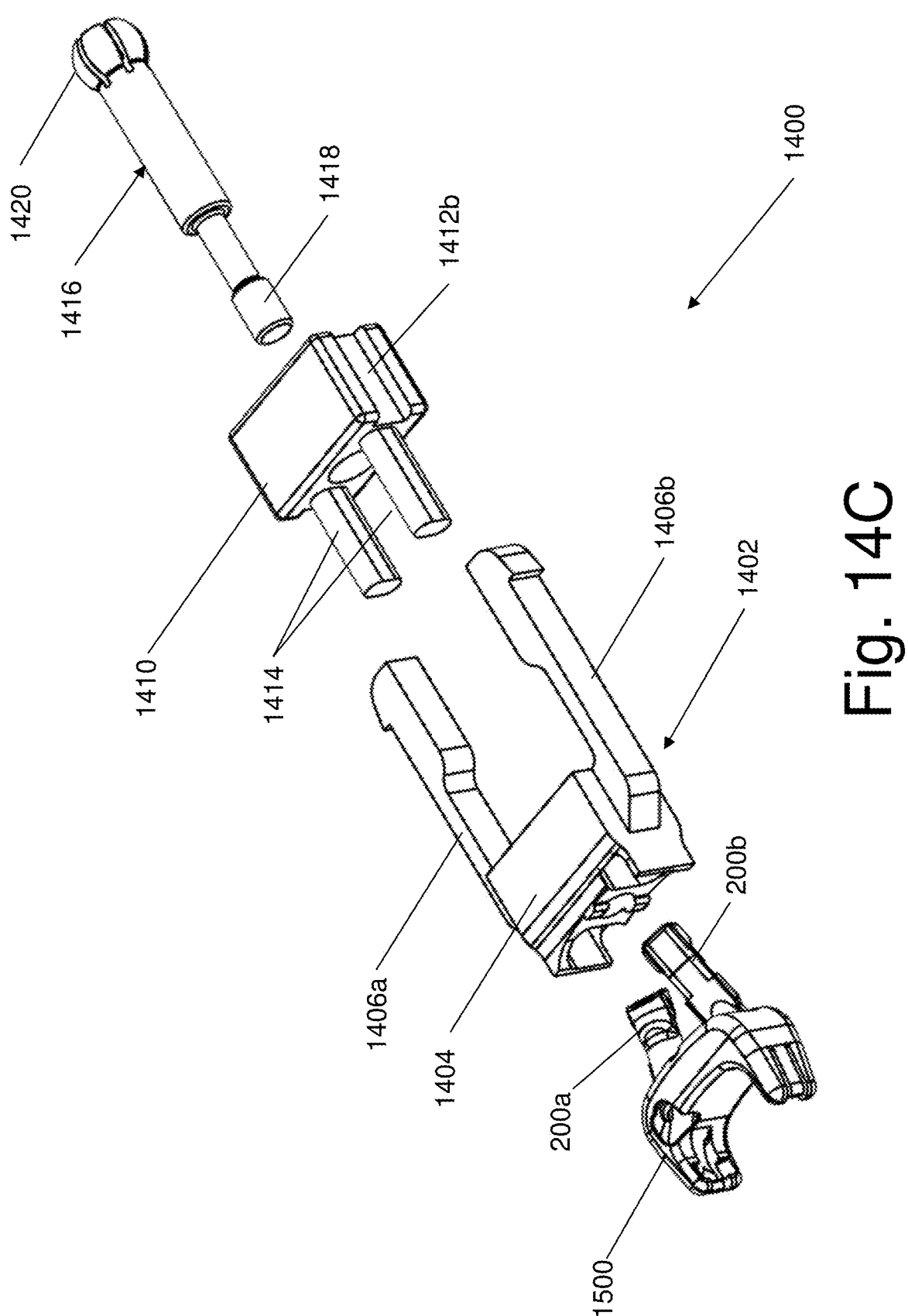
FIG. 14C is an exploded perspective view of the implant cassette of FIG. 12A.

Turning now to FIGS. 14A to 14C, there is a mounting unit 1402 comprising a main body 1404 and guide arms 1406*a* and 1406*b* extending on each side of the main body 1404 in a longitudinal direction towards a proximal end of the implant cassette 1400. In this embodiment, the main body 1404 defines two deployment channels 1408 corresponding to two anchors 200*a* and 200*b* of the implant 1500. As best illustrated by FIG. 14B, when the implant cassette 1400 is in a pre-deployed configuration, the anchors 200*a*-200*b* are partially positioned within the implant 1500 and partially positioned within the deployment channels 1408 where each anchor 200*a*-200*b* is at least partially within its own corresponding deployment channel. In other embodiments, the anchors 200*a*-200*b* may be entirely positioned within their respective deployment channels.

A force transmission unit 1410 is positioned on the proximal side of the main body 1404 and primarily fits between the guide arms 1406*a*-1406*b* of the mounting unit 1402. Each side of the force transmission unit 1410 defines a channel 1412*a*-1412*b* (only channel 1412*b* is visible in FIG. 14C) sized to interact with the guide arms 1406*a*-1406*b* such that the force transmission unit 1410 can slide along the guide arms in the longitudinal direction. The proximal face of the force transmission unit 1410 is designed to interact with and receive a longitudinal linear force from the translation element 1112 of the implant inserter tool 1102 (see FIGS. 11A and 11B). A plurality of push rods 1414 projects from a distal face of the force transmission unit 1410. The number and location of push rods 1414 corresponds to the number and location of the plurality of deployment channels 1408 defined within the main body 1404 of the mounting unit 1402. The push rods 1414 are sized and shaped to be received by the deployment channels 1408 defined within the mounting unit 1402.

In certain embodiments, a retention post 1416 having a distal threaded head 1418 and a proximal bulbous slotted end 1420. The retention post 1416 passes through center bores in the force transmission unit 1410 and the mounting unit 1402 so that the retention post extends from the implant 1500 to the proximal face of the force transmission unit 1410. In a pre-deployed configuration, the threaded head 1418 couples to a threaded aperture (not shown) defined with a proximal face of the implant 1500. Thus, the implant 1500 is coupled to the implant cassette 1400 by the retention post 1416.

The cassette 1400 is designed to be used in conjunction with the implant inserter tool 1102 (described above). The implant 1500 is deployed by the cassette 1400 and the inserter tool 1102 in a manner described above. Consequently, a description of the deployment of the anchors will not be repeated here. Reference should be made to FIGS. 12D through 12f and the referenced descriptions.

Once the anchors 200a and 200b are fully deployed, the turnable handle 1106 of the implant inserter tool 1102 may be rotated in a direction opposite to the insertion rotation direction with respect to the fixed collar 1110 (e.g., counterclockwise). This opposite rotation will cause the translation element 1112 to move longitudinally backwards towards a proximal end of the implant insertion tool 1102. As the translation element 1112 moves towards the translation block 1130, the side arms 1114a and 1114b of the implant inserter tool will rotate outwards in a direction transverse to the longitudinal axis 1101 as indicated in FIG. 11B.

Because the guide arms 1406a and 1406b of the implant are slidingly coupled to the side arms 1114a and 1114b of the inserter tool 1102, when the side arms 1114a and 1114b rotate outwards, the guide arms 1406a and 1406b will be decoupled from the side arms 1114a and 1114b. The inserter tool 1102 can now be removed from the surgical site leaving the implant cassette 1400 coupled to the deployed implant 1500.

A screwdriver or similar tool (not shown) can then be coupled to the bulbous slotted end 1420 of the retention post 1416. The user may then turn the screwdriver to back out the threaded head 1418 of the retention post 1416 out of the aperture defined within the implant 1500. Once the threaded head 1418 has been decoupled from the implant, the retention post 1416 may be removed from the surgical site. Because the bulbous slotted end 1420 is retained by the force transmission unit 1410 of the implant cassette 1400, the implant cassette will also be removed when the retention post 1416 is removed from the surgical site. The surgical site can then be closed in a traditional manner.

The abstract of the disclosure is provided for the sole reason of complying with the rules requiring an abstract, which will allow a searcher to quickly ascertain the subject matter of the technical disclosure of any patent issued from this disclosure. It is submitted with the understanding that it will not be used to interpret or limit the scope or meaning of the claims.

Any advantages and benefits described may not apply to all embodiments of the invention. When the word "means" is recited in a claim element, Applicant intends for the claim element to fall under 35 USC 112(f). Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word "means" are not intended to fall under 35 USC 112(f).

The foregoing description of the embodiments of the invention has been presented for the purposes of illustration and description. It is not intended to be exhaustive or to limit the invention to the precise form disclosed. Many combinations, modifications and variations are possible in light of the above teaching. For instance, in certain embodiments, each of the above described components and features may be individually or sequentially combined with other components or features and still be within the scope of the present invention. Undescribed embodiments which have interchanged components are still within the scope of the present invention. It is intended that the scope of the invention be limited not by this detailed description, but rather by the claims.

Additional Embodiments

Inserter Embodiments

For instance, in certain embodiments there may be a system for inserting an implant into a surgical site, the system comprising: an inserter, including, a rotatable handle having a proximal and distal end; an actuating rod having a proximal and a distal end, wherein the proximal end of the actuating rod is coupled to the distal end of the rotatable handle such that the rotatable handle can impart a torque onto the actuating rod; wherein the actuating rod has an exterior male helical screw thread defined over a predetermined length of the actuating rod; a non-rotating collar positioned around a portion of the actuating rod, the non-rotating collar defining an interior female helical screw thread surface sized to rotatably mate with the exterior male helical screw thread; a translator unit rotatably coupled to the distal end of the actuating rod such that as the actuating rod is turned with respect to the non-rotating collar, the translator unit moves longitudinally with respect to the non-rotating collar; at least one actuating projection; a cassette, including, an inserter block having at least one deployment channel, the at least one deployment channel sized to sliding accommodate the at least one actuating projection; the implant including at least one aperture, a first surface feature defined on one side of the implant and a second surface feature defined on an opposing side of the implant; and at least one anchor at least partially disposed in the at least one deployment channel.

Other embodiments of the inserter system described above may also include: a first lateral side arm having a proximal and a distal end wherein the distal end of the first lateral side arm includes a first rib for engaging the first surface feature of the implant and the proximal end of the first lateral side arm is detachably coupled to a first side of the inserter block; and a second lateral side arm having a proximal and a distal end wherein the distal end of the second lateral side arm includes a second rib for engaging the first surface feature of the implant and the proximal end of the second lateral side arm is detachably coupled to a second side of the inserter block.

Other embodiments of the inserter system described above may also include a force transmission unit and the at least one projection is coupled to the force transmission unit.

Additionally, in certain embodiments of the inserter system described above, the at least one projection may be coupled to the translator unit of the inserter.

Additionally, in certain embodiments of the inserter system described above, the at least one projection may be a push rod.

Certain embodiments of the inserter system described above may also include: a back block element fixedly coupled to the non-rotating collar, wherein the back block element includes the aperture having the interior female helical screw thread; a first arm having a proximal and a distal end, wherein the proximal end of the first arm is rotatably coupled to the back block element; and a second arm having a proximal and a distal end, wherein the proximal end of the second arm is rotatably coupled to the back block element.

In yet other embodiments, there may be a method for joining a first boney structure to a second boney structure using an implant inserter system, the method comprising: removably coupling an implant to an implant cassette; positioning at least a portion of a first non-threaded anchor into a first deployment channel defined within the implant cassette, the first anchor including a first non-threaded proximal head and a first non-threaded elongated body; positioning at least a portion of a second non-threaded anchor into a second deployment channel defined within the implant cassette, the second anchor including a second proximal head and a second elongated body; positioning an implant adjacent to the first boney structure and to the second boney structure; applying a torque to an actuating rod; converting the torque applied to the actuating rod into a forward linear motion to advance a first projection into the first deployment channel of the implant cassette and to advance a second projection into the second deployment channel of the implant cassette; pushing the first proximal head of the first non-threaded anchor with the first projection through the first deployment channel such that the first projection advances a first anchor in a first aperture defined within the implant and the first elongated body is driven, through the first aperture, and into the first boney structure along a first trajectory, and pushing the second proximal head of the second non-threaded anchor with the second projection through the second deployment channel such that the second projection advances the second anchor in a second aperture defined within the implant and the second elongated body is driven, through the second aperture, and into the second boney structure along a second trajectory; and continuing to push the first head such that as the first head reaches the first aperture and the first head interacts with the first aperture, that the first head moves transversely with respect to the first trajectory which causes the first boney structure to also move transversely with respect to the first trajectory.

Certain embodiments of the method described may also include continuing to push the second head such that as the second head reaches the second aperture and the second head interacts with the second aperture, the second head moves transversely with respect to the second trajectory which causes the second boney structure to also move transversely with respect to the second trajectory.

In yet other embodiments of the method described above the converting the torque applied to the actuating rod into a forward linear motion comprises: moving an exterior male thread defined on the actuating rod with respect to an interior female thread defined within a surface coupled to a stationary collar such that a distal end of the actuating rod moves linearly with respect to the stationary collar.

Other embodiments of the method described above could include coupling the distal end of the actuating rod to a translator unit which moves longitudinally with respect to the stationary collar.

Certain embodiments of the method described above wherein the causing the first head to interact with the first aperture comprises applying a force to an offset portion of the first head with a first force applying feature of the first aperture to move the first head transversely with respect to the first trajectory.

Certain embodiments of the method described above wherein the causing the second head to interact with the second aperture comprises applying a force to an offset portion of the second head with a second force applying feature of the second aperture to move the second head transversely with respect to the second trajectory.

Implant and Anchor Embodiments

In yet other embodiments, there may be an implant system for joining boney structures comprising: a first non-threaded anchor including, a first non-threaded elongated body having a center axis, a first non-threaded head coupled to a distal end of the first elongated body, the first head including a first portion of the first head that is substantially concentric to the center axis and a second portion of the first head that is offset from the center axis; an implant including, a first bone engaging surface; a first aperture defined within the implant, the first aperture having a first proximal portion and a first distal portion exiting through the first bone engaging surface, the first distal portion sized and to allow passage of the first elongated body along a first trajectory, the first proximal portion sized and shaped to accept the first head only upon an occurrence of transverse movement of the first head with respect to the first trajectory.

Other embodiments may include the above implant system, further comprising: a second non-threaded anchor including, a second non-threaded elongated body having a center axis, a second non-threaded head coupled to a distal end of the second elongated body, the second head including a second portion of the second head that is substantially concentric to the center axis and a second portion of the second head that is offset from the center axis; wherein the implant also includes: a second bone engaging surface, and a second aperture defined within the implant, the second aperture having a second proximal portion and a second distal portion exiting through the second bone engaging surface, the second distal portion sized and to allow passage of the second elongated body along a second trajectory, and the second proximal portion sized and shaped to accept the second head only upon an occurrence of transverse movement of the second head with respect to the second trajectory.

Other embodiments may include the above implant system, further comprising: a third non-threaded anchor including, a third non-threaded elongated body having a center axis, a third non-threaded head coupled to a distal end of the third elongated body, the third head including a third portion of the third head that is substantially concentric to the center axis and a third portion of the third head that is offset from the center axis; wherein the implant also includes, a third aperture defined within the implant, the third aperture having a third distal portion and a third proximal portion, the third distal portion sized and to allow passage of the third elongated body along a third trajectory, and the third proximal portion sized and shaped to accept the third head only upon an occurrence of transverse movement of the third head with respect to the third trajectory.

Other embodiments may include the above implant system, wherein the first aperture includes a first force applying feature sized and shaped to assert a transverse force on the second portion of the first head as the second portion of the first head slidingly engages the first force applying feature.

Other embodiments may include the above implant system, wherein the first aperture is curved in a first direction with respect to a center axis of the implant and the second aperture is curved in a second direction with respect to the center axis of the implant.

Other embodiments may include the above implant system, further comprising: a first side rail protruding from the first elongated body of the first non-threaded anchor; and a first side recess defined within the first aperture sized and positioned within the aperture to allow the first side rail to pass therethrough when the first elongated body follows the initial or first trajectory.

Other embodiments may include the above implant system, further comprising: a second side rail protruding from the first elongated body of the first non-threaded anchor; and a second side recess defined within the first aperture sized and positioned within the first aperture to allow the second side rail to pass therethrough when the first elongated body follows the initial or first trajectory.

Other embodiments may include the above implant system, further comprising: a first longitudinal step protruding from one side and substantially along a majority of a length of the first elongated body, a surface defined within the first aperture sized and shaped to slidingly engage the first longitudinal step.

Other embodiments may include the above implant system, further comprising: a fourth non-threaded anchor including, a fourth non-threaded elongated body having a center axis, a fourth non-threaded head coupled to a distal end of the fourth elongated body, the fourth head including a fourth portion of the fourth head that is substantially concentric to the center axis and a fourth portion of the fourth head that is offset from the center axis; wherein the implant also includes, a fourth aperture defined within the implant, the fourth aperture having a fourth distal portion and a fourth proximal portion, the fourth distal portion sized and to allow passage of the fourth elongated body along a fourth trajectory, and the fourth proximal portion sized and shaped to accept the fourth head only upon an occurrence of transverse movement of the fourth head with respect to the fourth trajectory.

Method Embodiments

In other embodiments, there may be a method for joining a first boney structure to an implant, the method comprising: positioning an implant adjacent to the first boney structure; introducing a first non-threaded anchor into a first non-threaded aperture defined within the implant, the first anchor including a first non-threaded proximal head and a first non-threaded elongated body; applying a non-torsional force onto a proximal end of the first head to drive the first elongated body through the first aperture, and into the first boney structure along a first trajectory; continuing to apply the non-torsional force onto the proximal end of the first head as the first head reaches the first aperture; and causing the first head to interact with the first aperture such that the first head moves transversely with respect to the first trajectory which causes the first boney structure to also move transversely towards the implant.

Other embodiments may include the above method, wherein the causing the first head to interact with the first aperture comprises applying a force to an offset portion of the first head with a first force applying feature of the first aperture to move the head transversely with respect to the first trajectory.

Other embodiments may include the above method, wherein the applying a non-torsional force comprises applying a smooth non-impact force.

In yet other embodiments, there may be a method for joining a first boney structure to a second boney structure, the method comprising: positioning an implant between the first boney structure and to the second boney structure; introducing a first non-threaded anchor into a first non-threaded aperture defined in the implant, the first anchor including a first non-threaded proximal head and a first non-threaded elongated body; introducing a second anchor into the second aperture defined in the implant, the second anchor including a second proximal head and a second elongated body, applying a non-torsional force onto a proximal end of the first head to drive the first elongated body, through the first aperture, and into the first boney structure along a first trajectory; applying a non-torsional force onto a proximal end of the second head to drive the second elongated body through the second aperture, and into the second boney structure along a second trajectory; continuing to apply the non-torsional force onto the proximal end of the first head as the first head reaches the first aperture and causing the first head to interact with the first aperture such that the first head moves transversely with respect to the first trajectory which causes the first boney structure to also move transversely with respect to the first trajectory; and continuing to apply the non-torsional force onto the proximal end of the second head as the second head reaches the second aperture and causing the second head to interact with the second aperture such that the second head moves transversely with respect to the second trajectory which causes the second boney structure to also move transversely with respect to the second trajectory.

Other embodiments may include the above methods, wherein the transverse movement of the first elongated body relative to the first trajectory and the transverse movement of the second elongated body relative to the second trajectory causes compression between the first boney structure and the second boney structure.

Other embodiments may include the above methods, wherein the transverse movement of the first elongated body relative to the first trajectory and the transverse movement of the second elongated body relative to the second trajectory causes distraction of the first boney structure relative to the second boney structure.

Other embodiments may include the above methods, further comprising: introducing a third non-threaded anchor into a third non-threaded aperture defined in the implant, the third anchor including a third non-threaded proximal head and a third non-threaded elongated body; applying a smooth non-torsional force onto a proximal end of the third head to drive the third elongated body, through the third aperture, and into the second boney structure along a third trajectory; and continuing to apply the smooth non-torsional force onto the proximal end of the third head as the third head reaches the third aperture and causing the third head to interact with the third aperture such that the third head moves transversely with respect to the third trajectory which causes the second boney structure to also move transversely with respect to the third trajectory.

Other embodiments may include the above methods, wherein the causing the first head to interact with the first aperture comprises applying a force to an offset portion of the first head with a first force applying feature of the first aperture to move the head transversely with respect to the first trajectory.

Other embodiments may include the above methods, further comprising: slidingly engaging a first side rail of the first elongated body with a first side recess defined within the first aperture of the implant; and disengaging the first side rail of the first elongated body with the first side recess to cause a transverse shift of the first elongated body with respect to the first trajectory.

Other embodiments may include the above methods, further comprising: slidingly engaging a second side rail of the first elongated body with a second side recess defined within the first aperture of the implant; and disengaging the second side rail of the first elongated body with the second side recess to cause the transverse shift of the first elongated body with respect to the first trajectory.

Other embodiments may include the above methods, further comprising: slidingly engaging a first stepped surface of the first elongated body with a first engaging surface of the first aperture; and disengaging the first stepped surface of the first elongated body with the first engaging surface of the first aperture to cause a transverse shift of the elongated body with respect to the first trajectory.

The above method, further comprising: engaging a first step of the elongated body with a first step engaging surface of the aperture; and disengaging the step of the elongated body with the first step engaging surface of the aperture to cause a transverse shift of the elongated body with respect to the first trajectory.

The above method, further comprising: engaging a first side rail of the elongated body with a first side recess defined within the implant and a first side surface of the first aperture; disengaging the side rail of the elongated body with the first side recess to cause a transverse shift of the elongated body with respect to the first trajectory; engaging a second side rail of the elongated body with a second side recess defined within the implant and a second side surface of the first aperture; and disengaging the second side rail of the elongated body with the second side recess to cause the transverse shift of the elongated body with respect to the first trajectory.

What is claimed is:

1. An implant system for joining boney structures comprising:
a first non-threaded anchor including,
  a first non-threaded elongated body having a center axis,
  a first non-threaded head coupled to a distal end of the first elongated body, the first head including a first portion of the first head that is substantially concentric to the center axis and a second portion of the first head that is offset from the center axis;
an implant including,
  a first bone engaging surface;
  a first aperture defined within the implant, the first aperture having:
    a first proximal portion and a first distal portion exiting through the first bone engaging surface, and
    a first force applying feature sized and shaped to assert a transverse force on the second portion of the first head as the second portion of the first head slidingly engages the first force applying feature;
    wherein the first distal portion is sized and to allow passage of the first elongated body along a first trajectory,
    wherein the first proximal portion is sized and shaped to accept the first head only upon an occurrence of transverse movement of the first head with respect to the first trajectory wherein the transverse movement is only caused by the interaction of the second portion of the first head with the first force applying feature.

2. The system of claim 1, further comprising:
a second non-threaded anchor including,
a second non-threaded elongated body having a center axis,
a second non-threaded head coupled to a distal end of the second elongated body, the second head including a second portion of the second head that is substantially concentric to the center axis and a second portion of the second head that is offset from the center axis;
  wherein the implant also includes:
  a second bone engaging surface, and
  a second aperture defined within the implant, the second aperture having a second proximal portion and a second distal portion exiting through the second bone engaging surface,
    the second distal portion sized and to allow passage of the second elongated body along a second trajectory, and
    the second proximal portion sized and shaped to accept the second head only upon an occurrence of transverse movement of the second head with respect to the second trajectory.

3. The system of claim 2, further comprising:
a third non-threaded anchor including,
  a third non-threaded elongated body having a center axis,
  a third non-threaded head coupled to a distal end of the third elongated body, the third head including a third portion of the third head that is substantially concentric to the center axis and a third portion of the third head that is offset from the center axis;
wherein the implant also includes,
  a third aperture defined within the implant, the third aperture having a third distal portion and a third proximal portion,
    the third distal portion sized and to allow passage of the third elongated body along a third trajectory, and
    the third proximal portion sized and shaped to accept the third head only upon an occurrence of transverse movement of the third head with respect to the third trajectory.

4. The system of claim 3, further comprising:
a fourth non-threaded anchor including,
  a fourth non-threaded elongated body having a center axis,
  a fourth non-threaded head coupled to a distal end of the fourth elongated body, the fourth head including a fourth portion of the fourth head that is substantially concentric to the center axis and a fourth portion of the fourth head that is offset from the center axis;
wherein the implant also includes,
  a fourth aperture defined within the implant, the fourth aperture having a fourth distal portion and a fourth proximal portion,
    the fourth distal portion sized and to allow passage of the fourth elongated body along a fourth trajectory, and
    the fourth proximal portion sized and shaped to accept the fourth head only upon an occurrence of transverse movement of the fourth head with respect to the fourth trajectory.

5. The system of claim 2, wherein the first aperture is curved in a first direction with respect to a center axis of the implant and the second aperture is curved in a second direction with respect to the center axis of the implant.

6. The system of claim 1, further comprising:

a first side rail protruding from the first elongated body of the first non-threaded anchor; and a first side recess defined within the first aperture sized and positioned within the aperture to allow the first side rail to pass therethrough when the first elongated body follows the first trajectory.

7. The system of claim 6, further comprising:

a second side rail protruding from the first elongated body of the first non-threaded anchor; and a second side recess defined within the first aperture sized and positioned within the first aperture to allow the second side rail to pass therethrough when the first elongated body follows the second trajectory.

8. The system of claim 1, further comprising:

a first longitudinal step protruding from one side and substantially along a majority of a length of the first elongated body, a surface defined within the first aperture sized and shaped to slidingly engage the first longitudinal step.

\* \* \* \* \*